(12) United States Patent
Yu et al.

(10) Patent No.: US 9,724,363 B2
(45) Date of Patent: *Aug. 8, 2017

(54) SKIN COMPOSITIONS AND METHODS OF USE THEREOF

(71) Applicant: Olivo Laboratories, LLC, Cambridge, MA (US)

(72) Inventors: Betty Yu, Cambridge, MA (US); Joseph Lomakin, Cambridge, MA (US); Soo-Young Kang, Newton, MA (US); Benjamin W. Adams, Seattle, WA (US)

(73) Assignee: OLIVO LABORATORIES, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/833,565

(22) Filed: Aug. 24, 2015

(65) Prior Publication Data

US 2016/0143840 A1    May 26, 2016

Related U.S. Application Data

(63) Continuation of application No. 13/430,563, filed on Mar. 26, 2012, now Pat. No. 9,114,096, which is a
(Continued)

(51) Int. Cl.
*A61K 8/895* (2006.01)
*A61K 8/25* (2006.01)
(Continued)

(52) U.S. Cl.
CPC .......... *A61K 31/765* (2013.01); *A61K 8/0204* (2013.01); *A61K 8/19* (2013.01);
(Continued)

(58) Field of Classification Search
CPC ........ A61K 8/345; A61K 8/891; A61K 8/895; A61K 8/0204; A61K 8/19; A61K 8/29;
(Continued)

(56) References Cited

U.S. PATENT DOCUMENTS 3,261,802 A * 7/1966 Bobera ................. C08G 77/16
523/351
3,884,866 A    5/1975 Jeram et al.
(Continued)

FOREIGN PATENT DOCUMENTS

EP    0445982 A2    9/1991
EP    0851000 A2    7/1998
(Continued)

OTHER PUBLICATIONS

Quartz Powder: retrieved from internet: http://www.cosmeticanalysis.com/cosmetic-ingredients/quartz-powder.html. Retrieved on Sep. 3, 2016.*
(Continued)

*Primary Examiner* — Hong Yu
(74) *Attorney, Agent, or Firm* — Morrison & Foerster LLP

(57) ABSTRACT

Provided are body corrective cosmetic formulations and methods of use thereof.

73 Claims, 7 Drawing Sheets

Related U.S. Application Data continuation of application No. PCT/US2011/050003, filed on Aug. 31, 2011.

(60) Provisional application No. 61/500,455, filed on Jun. 23, 2011, provisional application No. 61/499,002, filed on Jun. 20, 2011, provisional application No. 61/496,420, filed on Jun. 13, 2011, provisional application No. 61/493,020, filed on Jun. 3, 2011, provisional application No. 61/489,119, filed on May 23, 2011, provisional application No. 61/486,643, filed on May 16, 2011, provisional application No. 61/472,995, filed on Apr. 7, 2011, provisional application No. 61/446,377, filed on Feb. 24, 2011, provisional application No. 61/432,458, filed on Jan. 13, 2011, provisional application No. 61/412,531, filed on Nov. 11, 2010, provisional application No. 61/378,504, filed on Aug. 31, 2010.

(51) Int. Cl.

| | | |
|---|---|---|
| *A61K 8/58* | (2006.01) | |
| *A61K 8/894* | (2006.01) | |
| *A61K 8/02* | (2006.01) | |
| *A61Q 19/08* | (2006.01) | |
| *A61Q 1/02* | (2006.01) | |
| *A61K 8/29* | (2006.01) | |
| *A61K 8/891* | (2006.01) | |
| *A61K 8/19* | (2006.01) | |
| *A61K 31/765* | (2006.01) | |
| *A61K 8/34* | (2006.01) | |
| *A61Q 1/14* | (2006.01) | |
| *A61L 26/00* | (2006.01) | |
| *A61Q 19/00* | (2006.01) | |
| *A61Q 19/06* | (2006.01) | |

(52) U.S. Cl.
CPC ............ *A61K 8/25* (2013.01); *A61K 8/29* (2013.01); *A61K 8/345* (2013.01); *A61K 8/585* (2013.01); *A61K 8/891* (2013.01); *A61K 8/894* (2013.01); *A61K 8/895* (2013.01); *A61L 26/0019* (2013.01); *A61L 26/0095* (2013.01); *A61Q 1/02* (2013.01); *A61Q 1/14* (2013.01); *A61Q 19/00* (2013.01); *A61Q 19/06* (2013.01); *A61Q 19/08* (2013.01); *A61K 2800/412* (2013.01); *A61K 2800/43* (2013.01); *A61K 2800/58* (2013.01); *A61K 2800/5922* (2013.01); *A61K 2800/884* (2013.01); *A61K 2800/95* (2013.01)

(58) Field of Classification Search
CPC .......... A61K 8/585; A61K 8/894; A61K 8/25; A61K 31/765; A61K 2800/884; A61K 2800/95; A61K 2800/412; A61K 2800/43; A61K 2800/58; A61K 2800/5922; A61Q 1/02; A61Q 1/14; A61Q 19/08; A61Q 19/00; A61Q 19/06; A61L 26/0019; A61L 26/0095

See application file for complete search history.

(56) References Cited

U.S. PATENT DOCUMENTS

| | | | |
|---|---|---|---|
| 4,025,485 A | 5/1977 | Kodama et al. | |
| 4,683,278 A * | 7/1987 | Suzuki | C08L 83/04 525/277 |
| 4,908,140 A | 3/1990 | Bausch et al. | |
| 5,173,291 A * | 12/1992 | Brink | A01N 25/24 424/443 |
| 5,219,560 A | 6/1993 | Suzuki et al. | |
| 5,525,344 A | 6/1996 | Wivell | |
| 5,534,609 A | 7/1996 | Lewis et al. | |
| 5,616,632 A | 4/1997 | Fujiki et al. | |
| 5,800,816 A | 9/1998 | Brieva et al. | |
| 5,919,437 A | 7/1999 | Lee et al. | |
| 5,919,468 A | 7/1999 | Bara | |
| 5,922,470 A | 7/1999 | Bracken et al. | |
| 6,066,326 A | 5/2000 | Afriat et al. | |
| 6,313,190 B1 | 11/2001 | Bublewitz et al. | |
| 6,342,237 B1 | 1/2002 | Bara | |
| 6,355,724 B1 | 3/2002 | LeGrow et al. | |
| 6,391,944 B2 | 5/2002 | Canpont et al. | |
| 6,423,322 B1 | 7/2002 | Fry | |
| 6,471,985 B2 | 10/2002 | Guyuron et al. | |
| 6,512,072 B1 | 1/2003 | Gantner et al. | |
| 6,544,532 B1 | 4/2003 | Jager-Lezer et al. | |
| 6,573,299 B1 | 6/2003 | Petrus | |
| 6,613,185 B1 | 9/2003 | Valade et al. | |
| 6,682,749 B1 | 1/2004 | Potechin et al. | |
| 6,762,242 B1 | 7/2004 | Torto et al. | |
| 6,998,427 B2 | 2/2006 | Del Torto et al. | |
| 7,078,026 B2 | 7/2006 | Ferrari et al. | |
| 7,083,800 B1 | 8/2006 | Terren et al. | |
| 7,148,306 B2 * | 12/2006 | Achenbach | C08L 83/04 528/15 |
| 7,270,828 B2 | 9/2007 | Masuda et al. | |
| 7,273,658 B2 | 9/2007 | Benayoun et al. | |
| 7,335,708 B2 | 2/2008 | Bublewitz et al. | |
| 7,452,957 B2 * | 11/2008 | Sayre | B82Y 10/00 528/26 |
| 7,482,419 B2 | 1/2009 | Caprasse et al. | |
| 7,572,514 B2 | 8/2009 | Howe et al. | |
| 7,750,106 B2 | 7/2010 | Zheng et al. | |
| 8,133,478 B2 | 3/2012 | Maitra et al. | |
| 8,263,055 B2 | 9/2012 | Do | |
| 8,569,792 B2 | 10/2013 | Mitani et al. | |
| 8,611,746 B2 | 12/2013 | Pincemin et al. | |
| 8,658,755 B2 | 2/2014 | Saito | |
| 8,691,202 B2 * | 4/2014 | Yu | A61K 8/895 424/401 |
| 8,920,783 B2 | 12/2014 | Lin | |
| 9,044,288 B2 | 6/2015 | Angeletakis | |
| 9,096,721 B2 | 8/2015 | Garaud et al. | |
| 9,114,096 B2 * | 8/2015 | Yu | A61K 8/345 |
| 9,308,221 B2 | 4/2016 | Yu et al. | |
| 9,333,223 B2 * | 5/2016 | Yu | A61K 31/80 |
| 2002/0022040 A1 | 2/2002 | Robinson et al. | |
| 2002/0122771 A1 | 9/2002 | Holland et al. | |
| 2003/0180281 A1 | 9/2003 | Bott et al. | |
| 2004/0258628 A1 | 12/2004 | Riedel et al. | |
| 2005/0148727 A1 | 7/2005 | Ajbani et al. | |
| 2005/0158260 A1 | 7/2005 | Ferrari et al. | |
| 2005/0175562 A1 | 8/2005 | Hadasch et al. | |
| 2006/0029623 A1 | 2/2006 | Astruc et al. | |
| 2007/0142575 A1 | 6/2007 | Zheng et al. | |
| 2007/0142599 A1 | 6/2007 | Zheng et al. | |
| 2007/0212314 A1 | 9/2007 | Murphy et al. | |
| 2007/0244230 A1 | 10/2007 | Sixt et al. | |
| 2008/0102050 A1 | 5/2008 | Li et al. | |
| 2008/0159970 A1 | 7/2008 | Willemin | |
| 2008/0279797 A1 | 11/2008 | Maitra et al. | |
| 2009/0035246 A1 | 2/2009 | Do | |
| 2009/0214455 A1 | 8/2009 | Blin et al. | |
| 2010/0112019 A1 | 5/2010 | Thevenet | |
| 2010/0152135 A1 | 6/2010 | Blin | |
| 2010/0178266 A1 | 7/2010 | Huggins et al. | |
| 2010/0179105 A1 | 7/2010 | Blin et al. | |
| 2011/0040242 A1 | 2/2011 | Fallon et al. | |
| 2011/0166275 A1 * | 7/2011 | Zhang | C08K 3/22 524/397 |
| 2012/0237461 A1 | 9/2012 | Yu et al. | |
| 2012/0251600 A1 | 10/2012 | Yu et al. | |
| 2013/0052356 A1 | 2/2013 | Li | |
| 2013/0078209 A1 | 3/2013 | Yu et al. | |
| 2013/0178571 A1 | 7/2013 | Ogawa et al. | |
| 2014/0004065 A1 | 1/2014 | Souda et al. | |
| 2014/0004073 A1 | 1/2014 | Yu et al. | |
| 2014/0010769 A1 | 1/2014 | Lomakin et al. | |

(56) References Cited

U.S. PATENT DOCUMENTS

| | | |
|---|---|---|
| 2014/0044670 A1 | 2/2014 | Yu et al. |
| 2014/0322519 A1 | 10/2014 | Ahn et al. |
| 2015/0190516 A1 | 7/2015 | Cauvin et al. |
| 2015/0274971 A1 | 10/2015 | Endo et al. |
| 2015/0284590 A1 | 10/2015 | Endo et al. |
| 2016/0250250 A1 | 9/2016 | Yu et al. |
| 2016/0317574 A1 | 11/2016 | Yu et al. |

FOREIGN PATENT DOCUMENTS

| | | |
|---|---|---|
| EP | 0865787 A1 | 9/1998 |
| EP | 2090294 A1 | 8/2009 |
| FR | 2894817 A1 | 6/2007 |
| FR | 2910291 A1 | 6/2008 |
| FR | 2954143 A1 | 6/2011 |
| FR | 2956319 B1 | 8/2011 |
| JP | 2009520002 A1 | 5/2009 |
| JP | 2009530480 A1 | 8/2009 |
| WO | WO-00/74738 A1 | 12/2000 |
| WO | WO0074738 A1 | 12/2000 |
| WO | WO2007071886 A2 | 6/2007 |
| WO | 2007071886 A1 | 7/2007 |
| WO | WO-2007/102859 A2 | 9/2007 |
| WO | WO2007102859 A2 | 9/2007 |
| WO | WO2007117284 A2 | 10/2007 |
| WO | 2008075282 A1 | 6/2008 |
| WO | WO2008075282 A2 | 6/2008 |
| WO | WO-2009/042732 A1 | 4/2009 |
| WO | WO2009042732 A1 | 4/2009 |
| WO | WO2009090074 A1 | 7/2009 |
| WO | WO2009090242 A1 | 7/2009 |
| WO | WO2011001217 A1 | 1/2011 |
| WO | WO2012030984 A1 | 3/2012 |
| WO | WO2012030993 A2 | 3/2012 |
| WO | WO2013044098 A1 | 3/2013 |
| WO | 2013076450 A1 | 5/2013 |
| WO | WO2013070302 A1 | 5/2013 |
| WO | WO2013076450 A1 | 5/2013 |
| WO | WO2013158844 A2 | 10/2013 |
| WO | WO2015068859 A1 | 5/2015 |

OTHER PUBLICATIONS

Fumed Silica: retrieved form internet: http://www.powerchemcorp.com/library/public/fumed_silica/SiSiB_Fumed_Silica.pdf. Retrieved on Sep. 4, 2016.*

Brook et al.: Pretreatment of Liquid Silicone Rubbers to Remove Volatile Siloxanes, Ind. Eng. Chem. Res. 2007, 46, p. 8796-8805.*

Liquid Silicone Rubber: Global Product Selection Guide: retrieved from internet: https://www.dowcorning.com/content/publishedlit/95-1226-lsr-selection-guide.pdf. Retrived on Sep. 4, 2016.*

TraumaSkin FX™ Platinum Silicone Sculpting/Casting Medium: retrieved from internet: http://web.archive.org/web/20100407000529/http://www.paintandpowderstore.com/products.php?cat=47. Retrieved on Sep. 4, 2016.*

TraumaSkin FX™ Platinum Silicone Sculpting/Casting Medium: retrieved from internet: http://web.archive.org/web/20101008110519/http://paintandpowderstore.com/proddetail.php?prod=MM-1002&cat=47. Retrieved on Sep. 4, 2016.*

Silc Pig: retrieved from internet: https://www.smooth-on.com/product-line/silc-pig/. Retrieved on Sep. 4, 2016.*

European Search Report, Application No. EP11822576, date of mailing Mar. 16, 2015.

Japanese Office Action, Application No. JP 2013-527273, date of mailing Jun. 23, 2015.

Betty Yu et al., "An Elastic Second Skin", Nature Materials, pp. 1-10. May 9, 2016.

International Search Report for related PCT Application No. PCT/US2012/56667.

International Search Report for related PCT Application No. PCT/US2013/37116.

Ostergaard, Dow corning SA, Next Generation Rheology Control rings New Formulation Options for Personal Care, pp. 1-6:2008.

Correct Combo, [retrieved on Dec. 10, 2014 from on-line website http://www.drugs.com/otc/122754/correct-combo.html].

Silicones Plus product list, [retrieved on Dec. 10, 2014 from on-line website http://siliconesplus.com/storage/Silicones%20Pius%20Brochure_1.pdf].

Leow, Y-H, et al., Effect of Occlusion on Skin, Journal of Dermatological Treatment 8:139-142, 1997.

Hwang, Sang Min, et al., Basis of Occlusive Therapy in Psoriasis: Correcting Defects in Permeability Barrier and Calcium Gradient, International Journal of Dermatology, 40:223-231, 2001.

Klykken, Paal, et al., "Silicone Film-Forming Technologies for Health Care Applications", Dow Corning, 2004; 8pp.

International Search Report for related PCT Application No. PCT/US2011/050016, Apr. 30, 2012; 4 pp.

International Search Report for related PCT Application No. PCT/US2011/050003, Apr. 19, 2012; 6pp.

Leow, Y-H et al. (1997, e-pub. Jul. 12, 2009). "Effect of Occlusion on Skin," *Journal of Dermatological Treatment* 8(2):139-142.

Zhai, H. et al. (2001). "Effects of Skin Occlusion on Percutaneous Absorption: An Overview," *Skin Pharmacol Appl Skin Physiol* 14(1):1-10.

Zhai, H. et al. (2002). "Occlusion vs. Skin Barrier Function," *Skin Research and Tecnology* 8:1-6.

International Preliminary Report on Patentability mailed on Mar. 25, 2014 for PCT Application No. PCT/US2012/056667 filed on Sep. 21, 2012, 8 pages.

Written Opinion mailed on Dec. 3, 2012 for PCT Application No. PCT/US2012/056667 filed on Sep. 21, 2012, 7 pages.

* cited by examiner

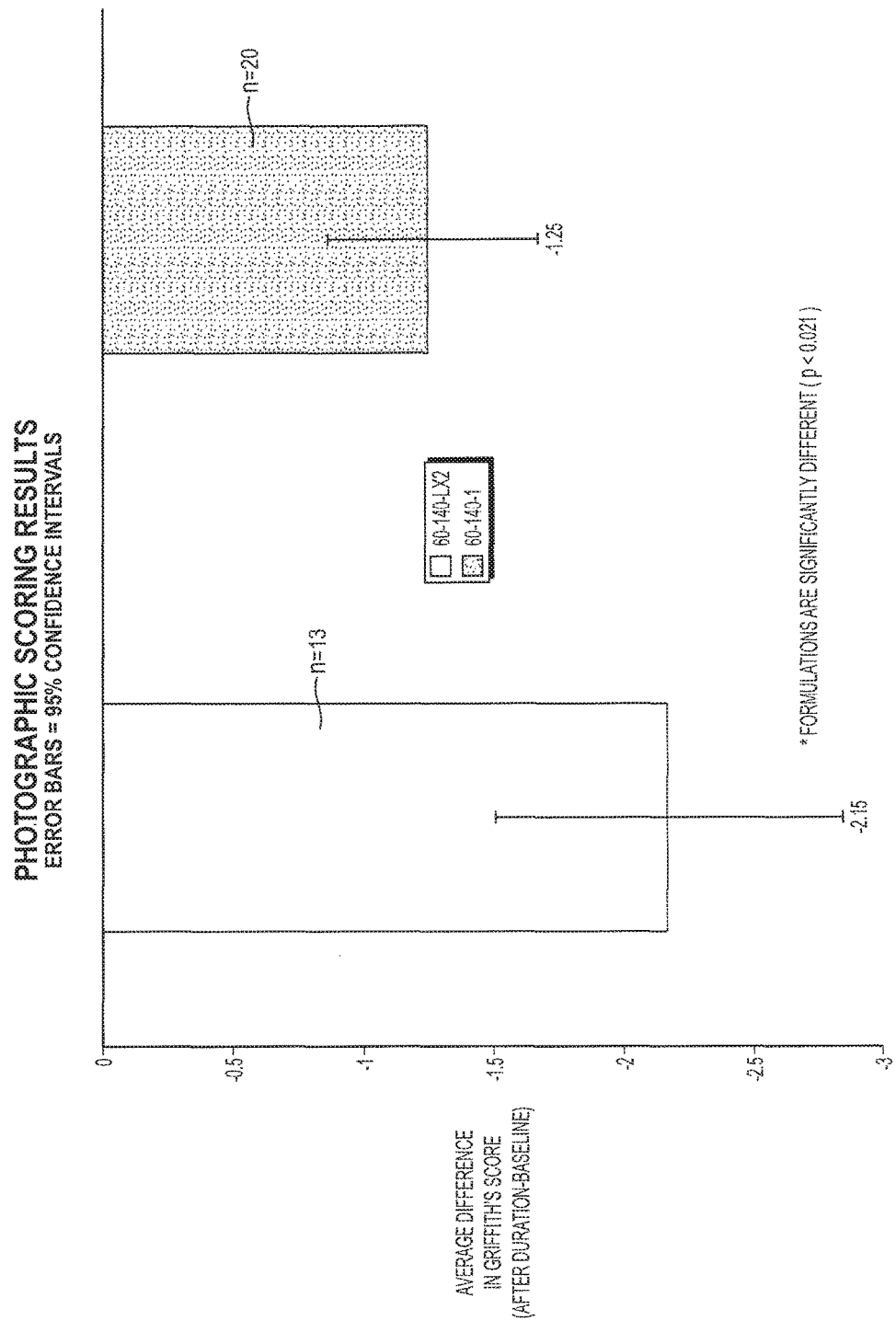

SKIN COMPOSITIONS AND METHODS OF USE THEREOF

RELATED APPLICATIONS

This application is continuation of U.S. application Ser. No. 13/430,563, filed Mar. 26, 2012, now U.S. Pat. No. 9,114,096, which is a continuation of International Application PCT/US2011/050003, filed Aug. 31, 2011, which claims the benefit of U.S. Provisional Patent Application No. 61/500,455, filed Jun. 23, 2011; U.S. Provisional Patent Application No. 61/499,002, filed Jun. 20, 2011; U.S. Provisional Patent Application 61/496,420, filed Jun. 13, 2011; U.S. Provisional Patent Application No. 61/493,020, filed Jun. 3, 2011; U.S. Provisional Patent Application No. 61/489,119, filed May 23, 2011; U.S. Provisional Patent Application No. 61/486,643, filed May 16, 2011; U.S. Provisional Patent Application No. 61/472,995, filed Apr. 7, 2011; U.S. Provisional Patent Application No. 61/446,377, filed Feb. 24, 2011; U.S. Provisional Patent Application No. 61/432,458, filed Jan. 13, 2011; U.S. Provisional Patent Application No. 61/412,531, filed on Nov. 11, 2010 and U.S. Provisional Patent Application No. 61/378,504, filed on Aug. 31, 2010. The entire contents of the foregoing applications are hereby incorporated by reference.

BACKGROUND OF THE INVENTION

Current methods for reducing the appearance of skin imperfections, for example wrinkles, fine lines, age spots, enlarged pores or scars, include invasive and non-invasive methods and formulations. Invasive techniques, such as surgery, fillers (e.g., Restylane, Juvederm), laser resurfacing or Botox®, may provide longer-lasting effects and can treat prominent imperfections. However, many consumers either cannot afford or do not wish undergo such drastic cosmetic treatments.

Examples of non-invasive methods include hiding imperfections by applying a foundation-type make-up to the skin or applying a cosmetic formulation that includes an ingredient that may reduce the appearance of the imperfections over time (e.g., an anti-wrinkle cream). Unfortunately, foundation make-up is not durable and cannot reduce the appearance of pronounced skin imperfections, such as deep wrinkles or scars, while cosmetic formulations containing ingredients that may reduce the appearance of an imperfection take time to produce an effect, and also may not reduce the appearance of a pronounced imperfection. In particular, many current cosmetic formulations do not have the required mechanical properties to reduce the appearance of pronounced imperfections.

High molecular weight polymers, including proteins and polysaccharides, have been used in attempts to develop anti-aging skin care cosmetic formulations (Jachowicz et al., *Skin Res. and Tech.*, 2008, 14:312-319). While these polymers change the physical properties (e.g., elasticity and stiffness) of the skin upon application to the skin, they did not provide the durability to enable natural, repeated facial motion for extended wear. The commercially available polymer materials used in skincare products today do not necessarily provide the elasticity, environmental resistance and skin adhesion for long lasting product performance nor do they provide the aesthetic feel and appearance required by the consumer of cosmetic products.

SUMMARY OF THE INVENTION

The present invention provides durable, natural looking, non-invasive compositions that exhibit desired aesthetic qualities and reduce appearance of skin and body imperfections, while providing cosmetic effects that typically are achieved through more invasive, dermatologist administered procedures, if at all.

In one embodiment, the invention provides non-invasive body corrective formulations that form a body corrective film upon application to the subject, thereby ameliorating body imperfections. The invention also provides methods of using such body corrective formulations. In another embodiment, the invention provides cleansers to remove the film.

Accordingly, in one embodiment, the invention pertains, at least in part, to body corrective formulations for application to a subject's skin that comprise a) a reactive reinforcing component; and b) a cross-linking component; in which the cross-linking component catalyzes an in situ cross-linking of the reactive reinforcing component, such that a body corrective film is formed on the subject's skin and the film has an appearance of natural skin.

In one embodiment, the invention pertains, at least in part, to two part body corrective formulation for application to a subject's skin that comprise a) a reactive reinforcing component; and b) a cross-linking component; in which the reactive reinforcing component and the cross-linking component are prevented from coming into contact prior to use; and in which the cross-linking component catalyzes an in situ cross-linking of the reactive reinforcing component, such that a body corrective film is formed on the subject's skin.

In one embodiment, the invention provides, at least in part, to body corrective formulations for application to a subject's skin that comprise a) a reactive reinforcing component; and b) a cross-linking component; in which the reactive reinforcing component has a viscosity of between about 5,000 and about 1,000,000 cSt or cP at 25° C.; and in which the cross-linking component catalyzes an in situ cross-linking of the reactive reinforcing component, such that a body corrective film is formed on the subject's skin.

In one embodiment, the invention pertains, at least in part, to body corrective formulations for application to a subject's skin that comprise a) a reactive reinforcing component; and b) a cross-linking component in which the reactive reinforcing component has a vinyl to functional hydride ratio of between about 1:10 and about 1:100; and in which the cross-linking component catalyzes an in situ cross-linking of the reactive reinforcing component, such that a body corrective film is formed on the subject's skin.

In one embodiment, the invention pertains, at least in part, to body corrective films prepared by a process comprising the steps of: a) applying a reactive reinforcing component to a subject's skin; and b) applying a cross-linking component to the reactive reinforcing component, in which the cross-linking component catalyzes an in situ cross-linking of the reactive reinforcing component, such that a body corrective film is formed on the subject's skin.

In one embodiment, the invention pertains, at least in part, to body shaping films prepared by a process comprising the steps of a) applying a reactive reinforcing component to a subject's skin; and b) applying a cross-linking component to the reactive reinforcing component, in which the cross-linking component catalyzes an in situ cross-linking of the reactive reinforcing component, such that a body shaping film is formed on the subject's skin.

In one embodiment, the invention pertains, at least in part, to methods for correcting body imperfections in a subject comprising applying to the subject's skin a formulation comprising a) a first reactive reinforcing component; and b) a second cross-linking component; in which the crosslinking component catalyzes an in situ cross-linking of the reactive reinforcing component, such that a film is formed on the skin, thereby correcting the body imperfections.

In one embodiment, the invention pertains, at least in part, to methods for protecting a subject's skin comprising applying to the subject's skin a formulation comprising a) a first reactive reinforcing component; and b) a second cross-linking component; in which the cross-linking component catalyzes an in situ cross-linking of the reactive reinforcing component such that a film is formed on the skin, thereby protecting the skin.

In one embodiment, the invention pertains, at least in part, to methods for shaping a subject's body, comprising applying to the subject's body a formulation comprising a) a first reactive reinforcing component; and b) a second cross-linking component; in which the cross-linking component catalyzes an in situ cross-linking of the reactive reinforcing component such that a film is formed on the body, thereby shaping the body.

In one embodiment, the invention pertains, at least in part, to methods for delivering an agent to a subject, comprising applying to the subject's skin a formulation comprising a) a first reactive reinforcing component optionally comprising one or more agents; and b) a second cross-linking component optionally comprising one or more agents; in which the cross-linking component catalyzes an in situ cross-linking of the reactive reinforcing component such that a film is formed on the skin, thereby delivering the agent to the subject.

In one embodiment, the invention pertains, at least in part, to body corrective formulations for application to a subject's body, comprising at least one preselected function modulating component, in which the composition forms a body corrective film upon application to the subject's body.

In one embodiment, the invention pertains, at least in part, to body corrective formulations for application to a subject's skin that target a treatment area on a subject's body, comprising at least one preselected treatment specific component, wherein the composition forms a body corrective film upon application to the target treatment area on the subject's body.

In one embodiment, the invention pertains, at least in part, to a film removing cleanser for use in removing a body corrective film, wherein the film is prepared by a process comprising the steps of applying a reactive reinforcing component to skin; and applying a cross-linking component to said reactive reinforcing component, and wherein said cross-linking component catalyzes an in situ cross-linking of the reactive reinforcing component.

In another embodiment, the invention pertains, at least in part, to a film removing cleanser comprising a film wetting component, a penetration component, a film swelling component and a film release component.

In some embodiments, the invention pertains to a formulation for repairing a body corrective film applied to skin, wherein said formulation comprises a) a first reactive reinforcing component and b) a second cross-linking component, wherein the cross-linking component catalyzes an in situ cross-linking of the reactive reinforcing component such that a film is formed on the skin.

In some embodiments, the invention pertains, at least in part, to a method for repairing a body corrective film applied to skin comprising the steps of a) identifying an area of the film in need of repair, b) optionally smoothing the edges of the film; and c) applying a formulation for repairing the film, wherein the formulation comprises a first reactive reinforcing component and a second cross-linking component, wherein the cross-linking component catalyzes an in situ cross-linking of the reactive reinforcing component such that a film is formed on the skin, thereby repairing the body corrective film.

In some embodiments, the invention pertains, at least in part, to a kit for repairing a body corrective film, the kit comprising a formulation comprising a) a first reactive reinforcing component and b) a second cross-linking component, wherein the cross-linking component catalyzes an in situ cross-linking of the reactive reinforcing component such that a film is formed on the skin.

BRIEF DESCRIPTION OF THE DRAWINGS

FIG. 7 is a chart illustrating the average Griffith's score result from the blinded evaluation of the panelist's photographs. The Griffith's score is a standardized quantitative measure of the extent of photodamage, where a score of 0 corresponds to no photodamage, and a score of 9 represents severe photodamage. For the two examples, the Griffith's score was reduced by 2.15 and by 1.25 points, following application of formula 60-140-LX2 and 60-140-1, respectively. This result is consistent with FIGS. 4 and 5, where panelists appeared younger following formulation application.

DETAILED DESCRIPTION OF THE INVENTION

Figure 1:
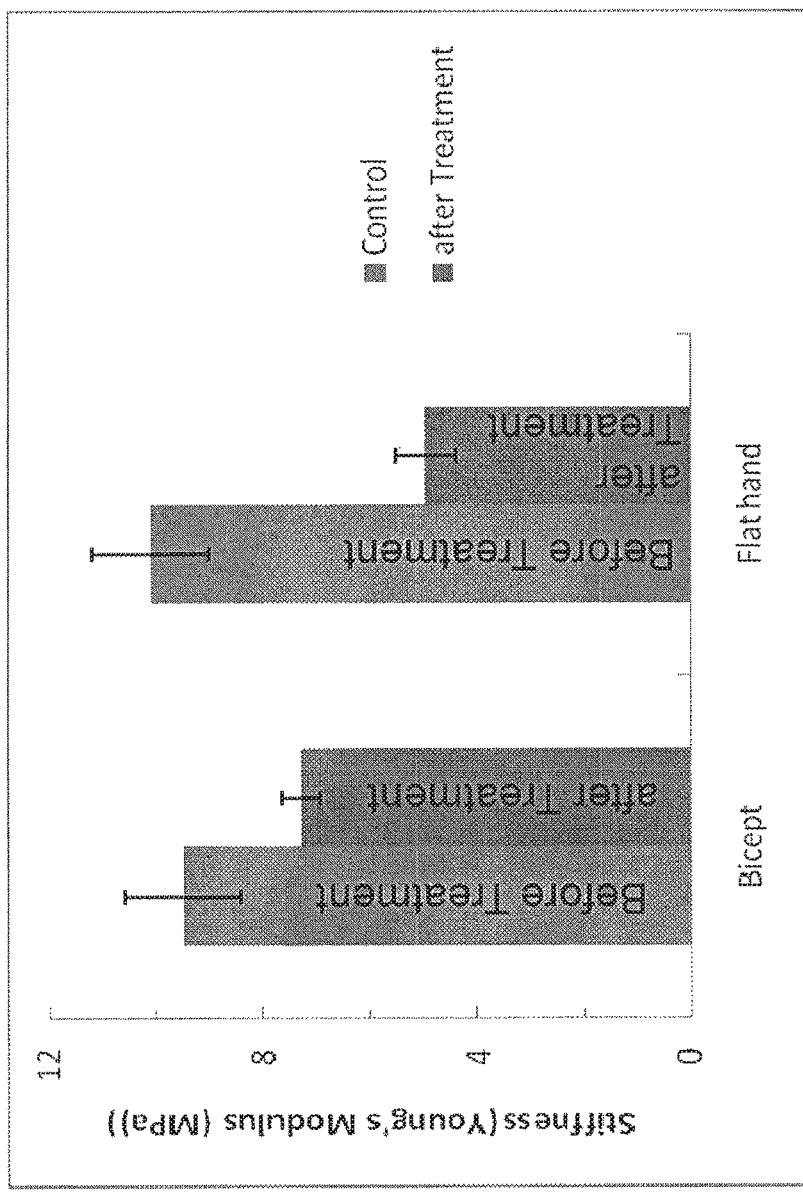
FIG. 1 is a chart illustrating the the change in the Young's Modulus of the skin after the application of a formulation of the invention. The change in Young's Modulus indicates that there is a reduction in the stiffness of skin upon application of the formulation.

In some embodiments, the invention pertains, at least in part, to body corrective formulations for application to the skin that comprise a) a reactive reinforcing component; and b) a cross-linking component; in which the cross-linking component catalyzes an in situ cross-linking of the reactive reinforcing component, such that a body corrective film is formed on the skin.

The language "body corrective formulation" or "formulation" includes cosmetic compositions that, when applied to the body, form a film on the body that ameliorate body imperfections. The language "body imperfections" includes those parts of a subject's body that the subject perceives as blemished or a flawed, or in which a skilled artisan, for example a dermatologist, an aesthetician or a plastic surgeon, would consider as blemished or flawed. The language "body imperfections" include skin imperfections, as well as sagging of soft body tissues (e.g., loose or sagging skin, sagging breasts, buttocks, abdomen, jowls, neck and the like). The language "skin imperfections" include those items on a subject's skin that the subject perceives as a blemish or a flaw. Examples of skin imperfections include port wine stain or nevus flammeus (e.g., nevus flammeus nuchae or midline nevus flammeus) melasma, wrinkles, blemishes, acne, moles, scars, tattoos, bruises, skin disfigurements, birth marks, sun damage, age damage, uneven skin tone, sagging skin, skin roughness, hyperpigmentation, enlarged pores, telangiectasia, redness, shine, cellulite, stretch marks or loss of skin elasticity.

In one embodiment of the invention, the compositions, formulations or films of the invention result in visual and or tactile improvement in skin properties. In certain embodiments, the compositions, formulations or films of the invention mask, conceal, or cover, but do not treat the skin or body imperfection of the subject.

In at least one embodiment, a skin or body imperfection does not include wounds or dermatological disorders.

The language "wounds" includes injuries to the skin wherein the skin is torn, cut or punctured. A wound is a break in the skin. In one embodiment, the wound is caused by skin contact with a foreign object. The break in the skin may cause external bleeding. Wounds include open wounds, for example, abrasions, lacerations, incisions, punctures, avulsions, or amputations. Wounds also include burn wounds. A burn is a type of injury to flesh caused by heat, electricity, chemicals, light, radiation or friction.

The language "dermatological disorder" includes disorders that cause at least one symptom on the skin of a subject requiring medical treatment. In one embodiment, dermatological disorders are caused by autoimmune disorders. In another embodiment, a dermatological disorder is caused by environmental factors, such a allergens or chemicals. Examples of symptoms of dermatological disorders requiring treatment is dermatitis, itchy skin, dry skin, crusting, blistering, or cracking skin, skin edema, or skin lesion formation. Dermatological disorders include, but are not limited to, lichen simplex chronicus, cutaneous lupus (e.g., acute cutaneous lupus, subacute cutaneous lupus, chronic cutaneous lupus, chilblain lupus erythematosus, discoid lupus erythematosus, lupus erythematosus-lichen planus overlap syndrome, lupus erythematosus panniculitis, tumid lupus erythematosus and verrucous lupus erythematosus), psoriasis (e.g., psoriasis vulgaris, psoriatic erythroderma, pustular psoriasis, drug-induced psoriasis, inverse psoriasis, seborrheic-like psoriasis and guttate psoriasis), eczema (e.g., atopic eczema, atopic dermatitis, contact dermatitis, xerotic eczema, seborrhoeic dermatitis, dyshidrosis, discoid eczema, venous eczema, dermatitis herpetiformis, neurodermatitis and autoeczematization), or chronic dry skin.

In some embodiments, the body corrective formulation is a skin corrective formulation. The language "skin corrective formulation," includes cosmetic compositions that, when applied to the skin, form a film on the skin that ameliorate skin imperfections. In some embodiments, the amelioration is a complete amelioration or a partial amelioration. One of skill in the art would be able to determine the extent of amelioration of one or more of the body imperfections by using the methods described in Example 6.

In some embodiments, the body corrective formulation is a body shaping formulation. A body shaping formulation includes cosmetic compositions that when applied to the skin, form a body shaping film on the subject's skin.

In some embodiments, the body corrective formulation is a skin protective formulation. A skin protective formulation includes cosmetic compositions that when applied to the skin, form a protective film on the subject's skin.

In some embodiments, the body corrective formulation can deliver cosmetic or therapeutic agents to a subject in need thereof.

In some embodiments, the body corrective formulation is used to repair a body corrective film.

In one embodiment, the body corrective formulations include a reactive reinforcing component and a cross-linking component. The language "reactive reinforcing component" includes a component that, when applied to the skin as a first component, is the basis of the body corrective film that is formed upon application of the cross-linking component to the reactive reinforcing component. In one embodiment, the reactive reinforcing component includes at least one reactive constituent and at least one reinforcing constituent.

The language "reactive constituent" includes one or more constituents of the reactive reinforcing component that provide the reactive film-forming elements of the formulation. In some embodiments, the reactive constituent includes at least one polysiloxane, polyethylene oxide, polypropylene oxide, polyurea, polyurethane, polyester (including polylactic-co-glycolic acid, polycaprolactone, polylactic acid, polyglycolic acid, and polyhydroxybutyrate, polyamide, or polysulfone. In another embodiment, the reactive constituent is a compound of formula I:

(I)

wherein
W is $R^1R^2R^3SiO—$, $—OR^4$, $—NR^5R^6$, $—CR^7R^8R^9$ or $C_{5-10}$ aryl;
X is $—R^{11}R^{12}Si—O—$, $—OCONR^{13}—$, $—NR^{14}CONR^{15}—$, $—CO—$, $—NR^{16}CO—$, $—SO_2—$, $—O—$, $—S—$ or $—NR^{17}—$;
V is absent, $C_{1-20}$ alkyl, $C_{2-20}$ alkenyl, $C_{5-10}$ aryl, $—O—$, $—NR^{10}—$ or $—S—$;
Y is $—R^{18}R^{19}Si—O—$, $—OCONR^{20}—$, $—NR^{21}CONR^{22}—$, $—CO—$, $—NR^{23}CO—$, $—SO_2—$, $—O—$, $—S—$ or $—NR^{24}$;
Z is $—SiR^{25}R^{26}R^{27}$, $—OR^{28}$, $—NR^{29}R^{30}$, $—CR^{31}R^{32}R^{33}$ or $C_{5-10}$ aryl;
$R^1$, $R^2$, $R^3$, $R^7$, $R^8$, $R^9$, $R^{11}$, $R^{12}$, $R^{18}$ $R^{19}$, $R^{25}$, $R^{26}$, $R^{27}$, $R^{31}$, $R^{32}$ and $R^{33}$ are each independently hydrogen, $C_{1-20}$ alkyl, $C_{2-20}$ alkenyl, $C_{5-10}$ aryl, hydroxyl or $C_{1-20}$ alkoxyl;
$R^4$, $R^5$, $R^6$, $R^{13}$, $R^{14}$, $R^{15}$, $R^{16}$, $R^{17}$, $R^{20}$, $R^{21}$, $R^{22}$, $R^{23}$, $R^{24}$, $R^{28}$, $R^{29}$ and $R^{30}$ are each independently hydrogen, $C_{1-20}$ alkyl, $C_{2-20}$ alkenyl, $C_{5-10}$ aryl; and s and t are each independently an integer from about 0 to about 6000.

X and Y of formula I represent an independent "monomer unit." The number of X and Y monomer units present in formula I is provided by the value of s and t, respectively. Representative monomer units include:

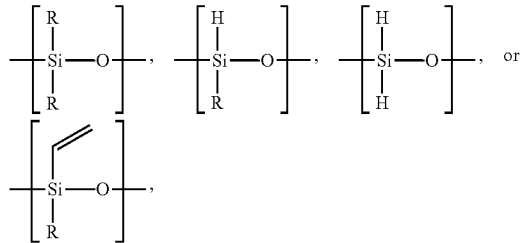

where R is as for defined for $R^1$, $R^2$, $R^3$, etc., above.

It is understood that when more than one X (or Y) monomer unit is present (e.g. s (or t) is more than one), the values for $R^{11}$, $R^{12}$, $R^{13}$, $R^{14}$, $R^{15}$, $R^{16}$, $R^{17}$, $R^{18}$ $R^{19}$, $R^{20}$, $R^{21}$, $R^{22}$, $R^{23}$, and $R^{24}$ are selected independently for each individual monomer unit described by $-[X]_s-$ (or $-[Y]_t-$). For example, if the value of the monomer unit X is $-R^{11}R^{12}Si-O-$ and the value of s is 3, then $-[X]_s-$ is

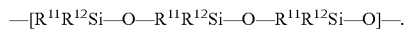

In this example, it is understood that the three $R^{11}$ groups present in may be the same or different from each other, for example, one $R^{11}$ may be hydrogen, and the two other $R^{11}$ groups may be methyl.

W and Z of formula I represent independent terminal caps, one on each end of the. For example, terminal caps include:

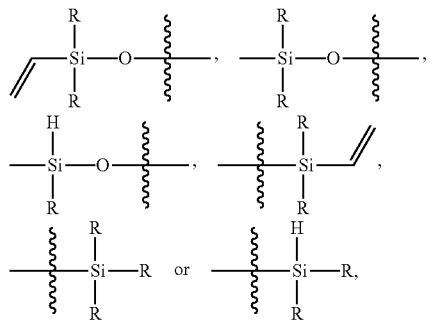

wherein ⌇ denotes attachment to a monomer unit and wherein R is as for defined for $R^1$, $R^2$, $R^3$, etc., above. In one embodiment, W is $R^1R^2R^3SiO-$, $-OR^4$, $-NR^5R^6$, $-CR^7R^8R^9$ or $C_{5-10}$ aryl;

X is $-R^{11}R^{12}Si-O-$, or $-NR^{14}CONR^{15}-$;

V is absent, $C_{1-20}$ alkyl, $C_{2-20}$ alkenyl, $C_{5-10}$ aryl, $-O-$, $-NR^{10}-$ or $-S-$;

Y is $-R^{18}R^{19}Si-O-$, or $-NR^{21}CONR^{22}-$;

Z is $-SiR^{25}R^{26}R^{27}$, $-OR^{28}$, $-NR^{29}R^{30}$, $-CR^{31}R^{32}R^{33}$ or $C_{5-10}$ aryl;

$R^1$, $R^2$, $R^3$, $R^7$, $R^8$, $R^9$, $R^{11}$, $R^{12}$, $R^{18}$, $R^{19}$, $R^{25}$, $R^{26}$, $R^{27}$, $R^{31}$, $R^{32}$ and $R^{33}$ are each independently hydrogen, $C_{1-20}$ alkyl, $C_{2-20}$, alkenyl, $C_{5-10}$ aryl, hydroxyl or $C_{1-20}$alkoxyl;

$R^4$, $R^5$, $R^6$, $R^{14}$, $R^{15}$, $R^{21}$, $R^{22}$, $R^{28}$, $R^{29}$ and $R^{30}$ are each independently hydrogen, $C_{1-20}$ alkyl, $C_{2-20}$ alkenyl, $C_{5-10}$ aryl; and s and t are each independently an integer from about 0 to about 6000, wherein the sum of s and t is not 0.

In one embodiment,

W is $R^1R^2R^3SiO-$, $-CR^7R^8R^9$ or $C_{5-10}$ aryl;

X is $-R^{11}R^{12}Si-O-$, or $-NR^{14}CONR^{15}-$;

V is absent, $C_{1-20}$ alkyl, $C_{2-20}$alkenyl, or $C_{5-10}$ aryl;

Y is $-R^{18}R^{19}Si-O-$, or $-NR^{21}CONR^{22}-$;

Z is $-SiR^{25}R^{26}R^{27}$, $-CR^{31}R^{32}R^{33}$ or $C_{5-10}$ aryl;

$R^1$, $R^2$, $R^3$, $R^7$, $R^8$, $R^9$, $R^{11}$, $R^{12}$, $R^{18}$, $R^{19}$, $R^{25}$, $R^{26}$, $R^{27}$, $R^{31}$, $R^{32}$ and $R^{33}$ are each independently hydrogen, $C_{1-20}$ alkyl, $C_{2-20}$ alkenyl, $C_{5-10}$ aryl, hydroxyl or $C_{1-20}$ alkoxyl;

$R^{14}$, $R^{15}$, $R^{21}$, and $R^{22}$ are each independently hydrogen, $C_{1-20}$ alkyl, $C_{2-20}$ alkenyl, $C_{5-10}$ aryl; and s and t are each independently an integer from about 0 to about 6000, wherein the sum of s and t is not 0.

In one embodiment, V is absent, W is $R^1R^2R^3SiO-$; X is $-R^{11}R^{12}Si-O-$; Y is $-R^{18}R^{19}Si-O-$; Z is $-SiR^{25}R^{26}R^{27}$; and $R^1$, $R^2$, $R^3$, $R^{11}$, $R^{12}$, $R^{18}$, $R^{19}$, $R^{25}$, $R^{26}$ and $R^{27}$ are each independently selected from $C_{1-20}$ alkyl (e.g., $C_1$ alkyl, such as methyl) or $C_{2-20}$ alkenyl (e.g., $C_2$ alkenyl, such as vinyl). In one embodiment, at least one of $R^1$, $R^2$, $R^3$, $R^{11}$, $R^{12}$, $R^{18}$, $R^{19}$, $R^{25}$, $R^{26}$ and $R^{27}$ is $C_{2-20}$ alkenyl, for example, $C_2$ alkenyl (e.g., vinyl). In another embodiment, at least two of $R^1$, $R^2$, $R^3$, $R^{11}$, $R^{12}$, $R^{18}$, $R^{19}$, $R^{25}$, $R^{26}$ and $R^{27}$ are $C_{2-20}$ alkenyl, for example, $C_2$ alkenyl (e.g., vinyl). In some embodiments, at least one of $R^1$, $R^2$, $R^3$, $R^{25}$, $R^{26}$ and $R^{27}$ are each $C_{2-20}$ alkenyl, for example, $C_2$ alkenyl (e.g., vinyl).

In one embodiment, V is absent, W is $R^1R^2R^3SiO-$; X is $-R^{11}R^{12}Si-O-$; Y is $-R^{18}R^{19}Si-O-$; Z is $-SiR^{25}R^{26}R^{27}$; and $R^1$, $R^2$, $R^3$, $R^{25}$, $R^{26}$, and $R^{27}$ are each independently selected from $C_{1-20}$ alkyl (e.g., $C_1$ alkyl, such as methyl) or $C_{2-20}$ alkenyl (e.g., $C_2$ alkenyl, such as vinyl); and $R^{11}$, $R^{12}$, $R^{18}$, and $R^{19}$ are each independently selected from $C_{1-20}$ alkyl (e.g., $C_1$ alkyl, such as methyl). In one embodiment, at least one of $R^1$, $R^2$, $R^3$, and at least one of $R^{25}$, $R^{26}$ and $R^{27}$ is $C_{2-20}$ alkenyl, for example, $C_2$ alkenyl (e.g., vinyl). In one embodiment, one of $R^1$, $R^2$, $R^3$ is $C_2$ alkenyl (e.g., vinyl) and the others are $C_{1-20}$ alkyl (e.g., $C_1$ alkyl, such as methyl), and at least one of $R^{25}$, $R^{26}$ and $R^{27}$ is $C_{2-20}$ alkenyl, for example, $C_2$ alkenyl (e.g., vinyl) and the others are $C_{1-20}$ alkyl (e.g., $C_1$ alkyl, such as methyl). In one embodiment, at least one of $R^{11}$ or $R^{12}$ and at least one of $R^{18}$ or $R^{19}$ is $C_{2-20}$ alkenyl, for example, $C_2$ alkenyl (e.g., vinyl) for at least one monomer unit. In one embodiment, one of $R^{11}$ or $R^{12}$ is $C_2$ alkenyl (e.g., vinyl) and the others are $C_{1-20}$ alkyl (e.g., $C_1$ alkyl, such as methyl), and at least one of $R^{18}$ or $R^{19}$ is $C_{2-20}$ alkenyl, for example, $C_2$ alkenyl (e.g., vinyl) and the others are $C_{1-20}$ alkyl (e.g., $C_1$ alkyl, such as methyl) for at least one monomer unit.

In some embodiments, the organopolysiloxane includes vinyl moieties only at the terminal caps of the polymer. In some embodiments, the organopolysiloxane include vinyl moieties only in the monomer units, but not at the terminal cap of the polymer. In other embodiments, the organopolysiloxane includes vinyl moieties at both the terminal cap or in the monomer unit of the polymer. In one embodiment, the polymer includes two vinyl moieties located either at the terminal cap, or within the monomer unit, or a combination thereof.

In one embodiment, on average at least two vinyl moieties are present in the polymer. In a specific embodiment, at least two vinyl moieties are present in the polymer and at least two vinyl moieties are present on the two terminal caps of the polymer. In a specific embodiment, only two vinyl moieties are present in the polymer. In a specific embodiment, only two vinyl moieties are present in the polymer and are located on each of the terminal caps. In a specific embodiment, on average at least two vinyl moieties are present in the polymer and at least two vinyl moieties are present in one or more monomer units of the polymer. In a specific embodiment, on average at least two vinyl moieties are present anywhere in the polymer, but separated from another vinyl moiety by about 2000 monomer units, for example, 1500, 1600, 1700, 1800, 1900, 2000, 2100, 2200, 2300, 2400, or 2500 monomer units. In a specific embodiment, on average at least two vinyl moieties are present anywhere in the polymer, but separated from another vinyl moiety by about 850 monomer units, for example, 350, 450, 550, 650, 750, 850, 950, 1050, 1150, 1250, or 1350 monomer units. In a specific embodiment, on average greater two vinyl moieties are present anywhere in the polymer, but separated from another vinyl moiety by about 40 monomer units, for example, 5, 10, 15, 20, 25, 30, 35, 40, 45, 50, 55, 60, 65, 70, 75, or 80 monomer units. In a specific embodiment, one or more Si—H units are present in addition to the vinyl moiety. Alternatively, in one embodiment, if a vinyl moiety is present then a Si—H is not present.

In one embodiment, V is absent, W is $R^1R^2R^3SiO$—; X is —$R^{11}R^{12}Si$—O—; Y is —$R^{18}R^{19}Si$—O—; Z is —$SiR^{25}R^{26}R^{27}$; $R^1$, $R^2$, $R^3$, $R^{11}$, $R^{12}$, $R^{18}$, $R^{19}$, $R^{25}$, $R^{26}$ and $R^{27}$ are each independently are each independently selected from hydrogen or $C_{1-20}$ alkyl (e.g., $C_1$ alkyl, such as methyl). In one embodiment, $R^1$, $R^2$, $R^3$, $R^{25}$, $R^{26}$ and $R^{27}$ are each independently selected from $C_{1-20}$ alkyl (e.g., $C_1$ alkyl, such as methyl); and $R^{11}$, $R^{12}$, $R^{18}$, and $R^{19}$ are each independently selected from hydrogen or $C_{1-20}$ alkyl (e.g., $C_1$ alkyl, such as methyl), wherein at least one of and $R^{11}$, $R^{12}$, $R^{18}$, and $R^{19}$ are hydrogen for at least one monomer unit. In one embodiment, on average greater than two Si—H units (e.g. one or more of $R^{11}$, $R^{12}$, $R^{18}$, and $R^{19}$ is hydrogen) are present in the polymer, for example 3-15 Si—H units may be present. In a specific embodiment, 8 Si—H units are present. In one embodiment, one or more Si—HI units (e.g. one or more of $R^{11}$, $R^{12}$, $R^{18}$, and $R^{19}$ is hydrogen) are present in the polymer. In one embodiment, at least two monomer units include a —Si—H unit (e.g. one or more of $R^{11}$, $R^{12}$, $R^{18}$, and $R^{19}$ is hydrogen). In one embodiment, at least three monomer units include a —Si—H unit (e.g. one or more of $R^{11}$, $R^{12}$, $R^{18}$, and $R^{19}$ is hydrogen). In one embodiment, at least four monomer units include a —Si—H unit (e.g. one or more of $R^{11}$, $R^{12}$, $R^{18}$, and $R^{19}$ is hydrogen). In one embodiment, at least five monomer units include a —Si—H unit (e.g. one or more of $R^{11}$, $R^{12}$, $R^{18}$, and $R^{19}$ is hydrogen). In one embodiment, at least six monomer units include a —Si—H unit (e.g. one or more of $R^{11}$, $R^{12}$, $R^{18}$, and $R^{19}$ is hydrogen). In one embodiment, at least seven monomer units include a —Si—H unit (e.g. one or more of $R^{11}$, $R^{12}$, $R^{18}$, and $R^{19}$ is hydrogen). In one embodiment, at least eight monomer units include a —Si—H unit (e.g. one or more of $R^{11}$, $R^{12}$, $R^{18}$, and $R^{19}$ is hydrogen). In one embodiment, a Si—H unit may be present in one or both the terminal caps in addition to being present in a monomer unit as described above. In a specific embodiment, Si-(alkyl) or Si-(vinyl) units may also be present in the polymer. In a specific embodiment, only Si—$CH_3$ and Si—H units are present. In a specific embodiment, monomer units or terminal caps include $C_1$-$C_{20}$alkyl, specifically methyl groups, for the non-Si—H positions of the polymer.

In a specific embodiment, on average at least two Si—H units are present in the polymer. In a specific embodiment, on average at least two Si—H moieties are present anywhere in the polymer, but separated from another Si—H moiety by about 2000 monomer units, for example, 1500, 1600, 1700, 1800, 1900, 2000, 2100, 2200, 2300, 2400, or 2500 monomer units. In a specific embodiment, on average at least two Si—H units are present anywhere in the polymer, but separated from another Si—H moiety by about 850 monomer units, for example, 350, 450, 550, 650, 750, 800, 850, 950, 1050, 1150, 1250, or 1350 monomer units. In a specific embodiment, on average greater than two Si—H units are present anywhere in the polymer, but separated from another Si—H moiety by about 40 monomer units, for example, 5, 10, 15, 20, 25, 30, 35, 40, 45, 50, 55, 60, 65, 70, 75, or 80 monomer units.

In one aspect of any one of the above embodiments, the sum of s and t is an integer from about 1000 to about 8000; from about 1300 to about 2700; from about 1500 to about 2700; from about 1600 to about 2600; from about 1600 to about 2500; from about 1700 to about 2500; from about 1800 to about 2400; from about 1800 to about 2300; from about 1900 to about 2300; from about 2000 to about 2200; from about 2050 to about 2150; from about 2100.

In one aspect of any one of the above embodiments, the sum of s and t is an integer from about 200 to about 1100; from about 600 to about 1100; from about 700 to about 1000; from about 800 to about 900; from about 825 to about 875; from about 850; from about 200 to about 800; from about 225 to about 700; from about 250 to about 600; from about 275 to about 500; from about 300 to about 400; from about 350 to about 400; from about 375. In a specific embodiment, the sum of s and t is an integer from about 850.

In one aspect of any one of the above embodiments, the sum of s and t is an integer from about 5 to about 1300; from about 10 to about 1100; from about 10 to about 600; from about 15 to about 500; from about 15 to about 400; from about 20 to about 300; from about 20 to about 200; from about 25 to about 100; from about 25 to about 75; from about 30 to about 50; from about 40.

In some embodiments, the reactive constituent comprises at least one organopolysiloxane. The term "organopolysiloxane" includes compounds of formula II:

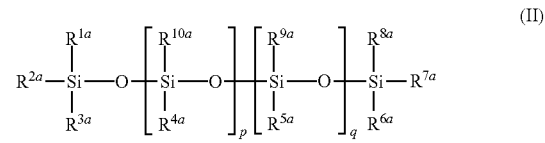

wherein $R^{1a}$, $R^{2a}$, $R^{3a}$, $R^{4a}$, $R^{5a}$, $R^{6a}$, $R^{7a}$, $R^{8a}$, $R^{9a}$ and $R^{10a}$ are each independently selected from hydrogen, $C_{1-20}$ alkyl, $C_{2-20}$ alkenyl, $C_{5-10}$ aryl, hydroxyl or $C_{1-20}$ alkoxyl and p and q are each independently an integer from between 10 and about 6000.

In some embodiments, the organopolysiloxane is a compound of formula IIa:

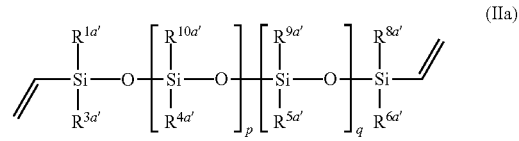

wherein $R^{1a'}$, $R^{3a'}$, $R^{4a'}$, $R^{5a'}$, $R^{6a'}$, $R^{8a'}$, $R^{9a'}$ and $R^{10a'}$ are each independently selected from hydrogen, $C_{1-20}$ alkyl. $C_{2-20}$alkenyl, $C_{5-10}$ aryl, hydroxyl or $C_{1-20}$ alkoxyl and p and q are each independently an integer from between 10 and about 6000. In one embodiment, $R^{1a'}$, $R^{3a'}$, $R^{4a'}$, $R^{5a'}$, $R^{6a'}$, $R^{8a'}$, $R^{9a'}$ and $R^{10a'}$ are alkyl (e.g., $C_1$ alkyl, such as methyl).

The term "alkyl" includes both branched and straight-chain saturated aliphatic hydrocarbon groups having the specified number of carbon atoms. The term "$C_{1-20}$ alkyl" includes branched and straight chain aliphatic groups having between 1 and 20 carbons. Examples of alkyl moieties include methyl, ethyl, n-propyl, i-propyl, n-butyl, s-butyl, t-butyl, n-pentyl, n-hexyl, isopropyl, isobutyl, sec-butyl, tert-butyl, isopentyl, and s-pentyl. Moreover, the term alkyl includes both "unsubstituted alkyls" and "substituted alkyls," the latter of which refers to alkyl moieties having substituents (e.g., F, Cl, Br, I, $NO_2$, CN, alkyl, aryl, hydroxyl, alkoxy, $COCH_3$ and the like) replacing a hydrogen on one or more carbons of the hydrocarbon backbone.

The term "alkenyl" includes the specified number of hydrocarbon atoms in either straight or branched configuration with one or more unsaturated carbon-carbon bonds that may occur in any stable point along the chain, such as ethenyl and propenyl. The language "$C_{2-20}$ alkenyl" includes branched and straight chain hydrocarbon groups with between 1 and 20 carbons and with one or more unsaturated carbon-carbon bonds. Moreover, the term "alkenyl" includes both "unsubstituted alkenyls" and "substituted alkenyls," the latter of which refers to alkenyl moieties having substituents (e.g., F, Cl, Br, I, $NO_2$, CN, alkyl, aryl, hydroxyl, alkoxy, $COCH_3$ and the like) replacing a hydrogen on one or more carbons of the hydrocarbon backbone.

The term "aryl" includes 5-10 membered monocyclic, bicyclic, or tricyclic rings, wherein at least one ring, if more than one is present, is aromatic. The term "aryl" also includes "heteraryl" moieties in which one heteroatom (e.g., N, O or S) replaces one or more carbons in the monocyclic, bicyclic, or tricyclic ring. The term "aryl" also includes both "unsubstituted aryls" and "substituted aryls," the latter of which refers to aryl moieties having substituents (e.g., F, Cl, Br, I, $NO_2$, CN, alkyl, hydroxyl, alkoxy, $COCH_3$ and the like) replacing a hydrogen on one or more carbons aromatic ring.

The term "hydroxyl" includes —OH.

The term "alkoxy" includes moieties in which an O is covalently bonded to a $C_{1-20}$ alkyl group, as defined above.

In some embodiments, the organopolysiloxane is vinyl terminated. The language "vinyl terminated organopolysiloxane" includes organopolysiloxanes of formula II in which one or both of $R^{2a}$ and $R^{7a}$ are substituted with a $C_2$ alkyl moiety, for example, a vinyl moiety (e.g., —CH=$CH_2$). In a specific embodiment, a "vinyl terminated organopolysiloxane" includes organopolysiloxanes of formula II in which one or both of $R^{2a}$ and $R^{7a}$ are substituted with a $C_2$ alkyl moiety, for example, a vinyl moiety (e.g., —CH=$CH_2$), and $R^{1a}$, $R^{3a}$, $R^{4a}$, $R^{5a}$, $R^{6a}$, $R^{8a}$, $R^{9a}$ and $R^{10a}$ are independently selected from $C_{1-20}$ alkyl, for example, methyl.

In other embodiments, the organopolysiloxane is selected from: vinyl terminated polydimethylsiloxane; vinyl terminated diphenylsiloxane-dimethylsiloxane copolymers; vinyl terminated polyphenylmethylsiloxane, vinylphenylmethyl terminated vinylphenylsiloxane-phenylmethylsiloxane copolymer; vinyl terminated trifluoropropylmethylsiloxane-dimethylsiloxane copolymer; vinyl terminated diethylsiloxane-dimethylsiloxane copolymer; vinylmethylsiloxane-dimethylsiloxane copolymer, trimethylsiloxy terminated; vinyl methylsiloxane-dimethylsiloxane copolymers, silanol terminated; vinylmethylsiloxane-dimethylsiloxane copolymers, vinyl terminated; vinyl gums; vinylmethylsiloxane homopolymers; vinyl T-structure polymers; monovinyl terminated polydimethylsiloxanes; vinylmethylsiloxane terpolymers; vinylmethoxysilane homopolymers and combinations thereof.

In some embodiments, the organopolysiloxane is a high viscosity organopolysiloxane, a low viscosity organopolysiloxane or a combination thereof.

When the organopolysiloxane is a combination of high and low viscosity organopolysiloxanes, the combination of a high viscosity and a low viscosity vinyl organosiloxane provides a bimodal distribution of organosiloxane molecular weights. In at least one embodiment, the organopolysiloxane is a combination of high and low viscosity vinyl-terminal organopolysiloxanes providing a bimodal distribution of the vinyl-terminated organopolysiloxane. In one embodiment, the organopolysiloxane is a combination of formulas I, II, IIa, IIb, and IIc, specifically, of formula IIa, IIb and/or IIc, or more specifically, of formula IIb and IIc, providing a bimodal distribution of the vinyl-terminated organopolysiloxane. In one embodiment, the bimodal distribution of polymer molecular weight is represented by a ratio of the molecular weights (for example, the sum of s and t) of the high viscosity organopolysiloxanes to the low viscosity organopolysiloxane. In one embodiment, this ratio is from 2 to 3. In a specific embodiment, this ratio is 2.5.

The term "viscosity" refers to the measure of the resistance of a fluid which is being deformed by either shear stress or tensile stress. One of skill in the art without undue experimentation would be able to determine how to measure the viscosity of a fluid, for example, using a viscometer or a rheometer. Representative methods include use of a capillary viscometer, rotational viscometer or rheometer to measure viscosity at an instrument specific strain. Specific methods for determining the viscosity of a fluid are shown in Example 8.

The language "high viscosity organopolysiloxane" includes organopolysiloxanes with a viscosity of between about 100,000 and about 500,000 cSt or cP at 25° C., for example, between about 110,000 and about 450,000 cSt or cP at 25° C., between about 120,000 and about 400,000 cSt or cP at 25° C., between about 125,000 and about 350,000 cSt or cP at 25° C., between about 130,000 and about 300,000 cSt or cP at 25° C., between about 135,000 and about 250.000 cSt or cP at 25° C., between about 140,000 and about 200,000 cSt or cP at 25° C., between about 145,000 and about 190,000 cSt or cP at 25° C., between about 150,000 and about 185,000 cSt or cP at 25° C., between about 155,000 and about 175,000 cSt or cP at 25° C., or between about 160,000 and about 170,000 cSt or cP at 25° C. In some embodiments, the viscosity of the high viscosity organopolysiloxane is between about 140,000 and about 200,000 cSt or cP at 25° C. In one embodiment, the high viscosity organopolysiloxane has a viscosity of about 165,000 cSt or cP at 25° C.

In one embodiment, the average molecular weight of the high viscosity organopolysiloxane is between about 100,000 and about 200,000 Da, for example, between about 115,000 and about 195,000 Da, between about 120,000 and about 190,000 Da, between about 125,000 and about 185,000 Da, between about 130,000 and about 180,000 Da, between about 135,000 and about 175,000 Da, between about 140,000 and about 170,000 Da, between about 145,000 and about 165,000 Da or between about 150,000 and about 160,000 Da. In one embodiment, the average molecular weight of the high viscosity organopolysiloxane is about 155,000 Da.

In some embodiments, the high viscosity organopolysiloxane is of formula II, in which $R^{2a}$ and $R^{7a}$ are $C_{2-20}$alkenyl, for example, $C_2$ alkenyl (e.g., vinyl) and $R^{1a}$, $R^{3a}$, $R^{4a}$, $R^{5a}$, $R^{6a}$, $R^{8a}$, $R^{9a}$ and $R^{10a}$ are each $C_{1-20}$ alkyl, for example, $C_1$ alkyl (e.g., methyl). In some embodiments, the high viscosity organopolysiloxane is vinyl terminated. In other embodiments, the high viscosity organopolysiloxane is vinyl terminated polydimethyl siloxane.

In some embodiments, the vinyl terminated high viscosity organopolysiloxane has a weight percent of vinyl of between about 0.010 and about 0.100, for example, between about 0.015 and about 0.080, between about 0.020 and about 0.075, between about 0.025 and about 0.060, or between about 0.030 and about 0.050. In one embodiment, the high viscosity organopolysiloxane has a weight percent of vinyl of between about 0.030 and about 0.040.

In other embodiments, the high viscosity organopolysiloxane has a vinyl equivalent per kilogram of between about 0.0100 and about 0.0200, for example, between about 0.0110 and about 0.0190, between about 0.0115 and about 0.0180, between about 0.0120 and about 0.0170, between about 0.0125 and about 0.0165 or between about 0.013 and about 0.016.

In one embodiment, the high viscosity organopolysiloxane has on average at least two vinyl units per high viscosity organopolysiloxane. In one embodiment, the monomer unit including a vinyl moiety are spaced throughout the polymer. In one embodiment, the vinyl-containing monomer unit is spaced about 2000 monomer units away from another vinyl-containing monomer unit or a vinyl-containing terminal cap. For example, the vinyl units in the high viscosity organopolysiloxanes are separated by 1500, 1600, 1700, 1800, 1900, 2000, 2100, 2200, 2300, 2400, or 2500 monomer units.

In some embodiments, the high viscosity organopolysiloxane is selected from: vinyl terminated polydimethylsiloxane; vinyl terminated diphenylsiloxane-dimethylsiloxane copolymers; vinyl terminated polyphenylmethylsiloxane, vinylphenylmethyl terminated vinylphenylsiloxane-phenylmethylsiloxane copolymer; vinyl terminated trifluoropropylmethylsiloxane-dimethylsiloxane copolymer; vinyl terminated diethylsiloxane-dimethylsiloxane copolymer; vinylmethylsiloxane-dimethylsiloxane copolymer, trimethylsiloxy terminated; vinylmethylsiloxane-dimethylsiloxane copolymers, silanol terminated; vinylmethylsiloxane-dimethylsiloxane copolymers, vinyl terminated; vinyl gums; vinylmethylsiloxane homopolymers; vinyl T-structure polymers; monovinyl terminated polydimethylsiloxanes; vinylmethylsiloxane terpolymers; vinylmethoxysilane homopolymers and combinations thereof.

The language "low viscosity organopolysiloxane" includes organopolysiloxanes with a viscosity of between about 500 and about 50,000 cSt or cP at 25° C., for example, between about 1,000 and about 45,000 cSt or cP at 25° C., between about 1,500 and about 40,000 cSt or cP at 25° C., between about 2,000 and about 35,000 cSt or cP at 25° C., between about 2,500 and about 30,000 cSt or cP at 25° C., between about 3,000 and about 25,000 cSt or cP at 25° C., between about 3,500 and about 20,000 cSt or cP at 25° C., between about 4,000 and about 15,000 cSt or cP at 25° C., or between about 4,000 and about 12,000 cSt or cP at 25° C. In some embodiments, the low viscosity organopolysiloxane includes organopolysiloxanes with a viscosity of between about 100 and about 5,000 cSt or cP at 25° C., for example, between about 200 and about 4000 cSt or cP at 25° C., between about 300 and about 3000 cSt or cP at 25° C., between about 400 and about 2000 cSt or cP at 25° C. or between about 750 and about 1500 cSt or cP at 25° C. In one embodiment, the low viscosity organopolysiloxane has a viscosity of about 10,000 cSt or cP at 25° C. In some embodiments, the low viscosity organopolysiloxane has a viscosity of about 1000 cSt or cP at 25° C.

In some embodiments, the low viscosity organopolysiloxane has an average molecular weight of between about 20,000 and about 80,000 Da, for example, between about 50,000 and about 75,000 Da, between about 55,000 and about 70,000 Da, between about 60,000 and about 65,000 Da or between 62,000 and about 63,000 Da. In one embodiment, the low viscosity organopolysiloxane has an average molecular weight of about 62,700 Da. In one embodiment, the low viscosity organopolysiloxane has an average molecular weight of about 28,000 Da.

In some embodiments, the low viscosity organopolysiloxane is of formula II, in which $R^{2a}$ and $R^{7a}$ are $C_{2-20}$ alkenyl, for example, $C_2$ alkenyl (e.g., vinyl) and $R^{1a}$, $R^{3a}$, $R^{4a}$, $R^{5a}$, $R^{6a}$, $R^{8a}$, $R^{9a}$ and $R^{10a}$ are each $C_{1-20}$ alkyl, for example, $C_1$ alkyl (e.g., methyl). In some embodiments, the low viscosity organopolysiloxane is vinyl terminated. In other embodiments, the low viscosity organopolysiloxane is vinyl terminated polydimethylsiloxane.

In some embodiments, the low viscosity organopolysiloxane has a weight percent of vinyl of between about 0.010 and about 0.30, for example, between about 0.020 and about 0.29, between about 0.030 and about 0.28, between about 0.040 and about 0.27, between about 0.050 and about 0.26, between about 0.060 between about 0.25, between about 0.070 and about 0.24, between about 0.080 and about 0.23, or between about 0.090 and about 0.22. In some embodiments, the low viscosity organopolysiloxane has a weight percent of vinyl of between about 0.18 and about 0.26.

In other embodiments, the low viscosity organopolysiloxane has a vinyl equivalent per kilogram of between about 0.010 and about 0.100, for example, between about 0.015 and about 0.090, between about 0.020 and about 0.080, between about 0.025 and about 0.070, between about 0.030 and about 0.060 or between about 0.040 and about 0.050. In some embodiments, the low viscosity organopolysiloxane has a vinyl equivalent per kilogram of between about 0.030 and about 0.040.

In other embodiments, the low viscosity organopolysiloxane has on average at least two vinyl units per low viscosity organopolysiloxane. In one embodiment, the monomer unit including a vinyl moiety are spaced throughout the polymer. In one embodiment, the vinyl-containing monomer unit is spaced about 800 monomer units away from another vinyl-containing monomer unit or a vinyl-containing terminal cap. For example, the vinyl units in the low viscosity organopolysiloxanes are separated by 450, 550, 650, 750, 800, 850, 950, 1050, 1150, 1250, or 1350 monomer units.

In some embodiments, the low viscosity organopolysiloxane is selected from: vinyl terminated polydimethylsiloxane; vinyl terminated diphenylsiloxane-dimethylsiloxane copolymers; vinyl terminated polyphenylmethylsiloxane, vinylphenylmethyl terminated vinylphenylsiloxane-phenylmethylsiloxane copolymer; vinyl terminated trifluoropropylmethylsiloxane-dimethylsiloxane copolymer; vinyl terminated diethylsiloxne-dimethylsiloxane copolymer; vinylmethylsiloxane-dimethylsiloxane copolymer, trimethylsiloxy terminated; vinylmethylsiloxane-dimethylsiloxane copolymers, silanol terminated; vinylmethylsiloxane-dimethylsiloxane copolymers, vinyl terminated; vinyl gums; vinylmethylsiloxane homopolymers; vinyl T-structure polymers; monovinyl terminated polydimethylsiloxanes; vinylmethylsiloxane terpolymers; vinylmethoxysilane homopolymers and combinations thereof.

In some embodiments, the organopolysiloxane is a compound of formula IIb:

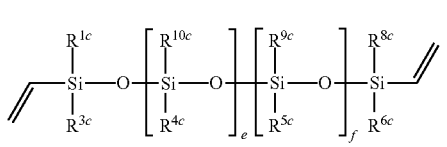
(IIb)

wherein $R^{1c}$, $R^{3c}$, $R^{4c}$, $R^{5c}$, $R^{6c}$, $R^{8c}$, $R^{9c}$, and $R^{10c}$ are each independently selected from hydrogen, $C_{1-20}$ alkyl, $C_{2-20}$ alkenyl, $C_{5-10}$ aryl, hydroxyl or $C_{1-20}$ alkoxyl and e and f are each independently an integer from between 10 and about 6000. In one embodiment, $R^{1c}$, $R^{3c}$, $R^{4c}$, $R^{5c}$, $R^{6c}$, $R^{8c}$, $R^{9c}$ and $R^{10c}$ are alkyl (e.g., $C_1$ alkyl, such as methyl). In some embodiments, the sum of e and f is an integer from about 1000 to about 8000; from about 1300 to about 2700; from about 1500 to about 2700; from about 1600 to about 2600; from about 1600 to about 2500; from about 1700 to about 2500; from about 1800 to about 2400; from about 1800 to about 2300; from about 1900 to about 2300; from about 2000 to about 2200; from about 2050 to about 2150; from about 2100.

In some embodiments, the organopolysiloxane is a compound of formula IIc:

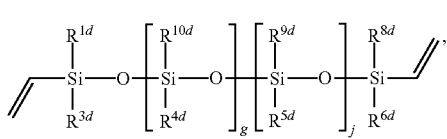
(IIc)

wherein $R^{1d}$, $R^{3d}$, $R^{4d}$, $R^{5d}$, $R^{6d}$, $R^{8d}$, $R^{9d}$ and $R^{10d}$ are each independently selected from hydrogen, $C_{1-20}$ alkyl, $C_{2-20}$ alkenyl, $C_{2-20}$ aryl, hydroxyl or $C_{1-20}$ alkoxyl and g and j are each independently an integer from between 10 and about 6000. In one embodiment, $R^{1d}$, $R^{3d}$, $R^{4d}$, $R^{5d}$, $R^{6d}$, $R^{8d}$, $R^{9d}$ and $R^{10d}$ are alkyl (e.g., $C_1$ alkyl, such as methyl). In some embodiments, the sum of g and j is an integer from about 200 to about 1100; from about 600 to about 1100; from about 700 to about 1000; from about 800 to about 900; from about 825 to about 875; from about 850; from about 200 to about 800; from about 225 to about 700; from about 250 to about 600; from about 275 to about 500; from about 300 to about 400; from about 350 to about 400; from about 375. In some embodiments, the sum of g and j is an integer from about 850.

In some embodiments, the reactive constituent comprises at least one hydride functionalized polysiloxane. The language "hydride functionalized polysiloxane" includes compounds of formula III:

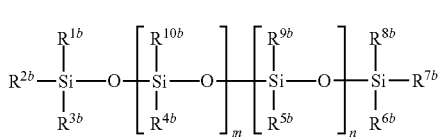
(III)

wherein $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ are each independently selected from hydrogen, $C_{1-20}$ alkyl, $C_{2-20}$ alkenyl, $C_{5-10}$ aryl, hydroxyl or $C_{1-20}$ alkoxy and m and n are each independently an integer from between 10 and about 6000, provided that at least one of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ is hydrogen. In some embodiments, at least one of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ is hydrogen and the remainder are $C_{1-20}$ alkyl. In some embodiments, at least two of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ are hydrogen (e.g., two Si—H units per functionalized hydride polysiloxane molecule). In other embodiments, at least three of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ are hydrogen (e.g., three Si—H units per functionalized hydride polysiloxane molecule). In some embodiments, at least two of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ are hydrogen (e.g., two Si—H units per functionalized hydride polysiloxane molecule) and the remainder are $C_{1-20}$ alkyl. In other embodiments, at least three of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ are hydrogen (e.g., three Si—H units per functionalized hydride polysiloxane molecule) and the remainder are $C_{1-20}$ alkyl. In some embodiments, at least two of $R^{4b}$, $R^{5b}$, $R^{9b}$ and $R^{10b}$ are hydrogen (e.g., two Si—H units per functionalized hydride polysiloxane molecule) and the remainder are $C_{1-20}$ alkyl. In other embodiments, at least three of $R^{4b}$, $R^{5b}$, $R^{9b}$ and $R^{10b}$ are hydrogen (e.g., three Si—H units per functionalized hydride polysiloxane molecule) and the remainder are $C_{1-20}$ alkyl.

In one embodiment, at least greater than two monomer units of formula III include a —Si—H unit (e.g. one or more of $R^{11}$, $R^{12}$, $R^{18}$, and $R^{19}$ is hydrogen). For example, on average 2 to 15 monomer units of formula III include a Si—H unit. In one embodiment, at least two monomer units of formula III include a —Si—H unit (e.g. one or more of $R^{11}$, $R^{12}$, $R^{18}$, and $R^{19}$ is hydrogen). In one embodiment, at least three monomer units of formula III include a —Si—H unit (e.g. one or more of $R^{11}$, $R^{12}$, $R^{18}$, and $R^{19}$ is hydrogen). In one embodiment, at least four monomer units of formula III include a —Si—H unit (e.g. one or more of $R^{11}$, $R^{12}$, $R^{18}$, and $R^{19}$ is hydrogen). In one embodiment, at least five monomer units of formula III include a —Si—H unit (e.g. one or more of $R^{11}$, $R^{12}$, $R^{18}$, and $R^{19}$ is hydrogen). In one embodiment, at least six monomer units of formula II include a —Si—H unit (e.g. one or more of $R^{11}$, $R^{12}$, $R^{18}$, and $R^{19}$ is hydrogen). In one embodiment, at least seven monomer units of formula III include a —Si—H unit (e.g. one or more of $R^{11}$, $R^{12}$, $R^{18}$, and $R^{19}$ is hydrogen). In one embodiment, at least eight monomer units of formula III include a —Si—H unit (e.g. one or more of $R^{11}$, $R^{12}$, $R^{18}$, and $R^{19}$ is hydrogen). In a specific embodiment, the non Si—H positions may include a Si-(alkyl) or Si-(vinyl) unit. In a specific embodiment, the non-Si—H positions are Si—$CH_3$. In one embodiment, the Si—H units in the hydride-functionalized organopolysiloxanes are separated by 5, 10, 15, 20, 25, 30, 35, 40, 45, 50, 60, 65, 70, 75, 80, 85, 90, 100, 125, 150, or 200 monomer units.

In one aspect of any one of the above embodiments, the sum of m and n is an integer from about 10 to about 1300; from about 10 to about 1100; from about 10 to about 600; from about 15 to about 500; from about 15 to about 400; from about 20 to about 300; from about 20 to about 200; from about 25 to about 100; from about 25 to about 75; from about 30 to about 50; from about 40.

In some embodiments, the hydride functionalized polysiloxane includes Si—H units only at the terminal caps of the polymer. In some embodiments, the polysiloxane include Si—H units only in the monomer units, but not at the terminal cap of the polymer. In other embodiments, the polysiloxane includes Si—H units at both the terminal cap or in the monomer unit of the polymer. In one embodiment, the polysiloxane includes two to twelve Si—H units located either at the terminal cap, or within the monomer unit, or a combination thereof. In one embodiment, the polysiloxane includes four to fifteen Si—H units located either at the terminal cap, or within the monomer unit, or a combination thereof. In one embodiment, the polysiloxane includes eight Si—H units located either at the terminal cap, or within the monomer unit, or a combination thereof.

In some embodiments, the hydride functionalized polysiloxane has a viscosity of between about 5 and about 11,000 cSt or cP at 25° C., for example, between about 10 and about 10,000 cSt or cP at 25° C., between about 15 and about 5,000 cSt or cP at 25° C., between about 20 and about 1,000 cSt or cP at 25° C., between about 25 and about 500 cSt or cP at 25° C., between about 30 and about 100 cSt or cP at 25° C., and between about 40 and about 50 cSt or cP at 25° C. In one embodiment, the hydride functionalized polysiloxane has a viscosity of about 45 cSt or cP at 25° C.

In some embodiments, the hydride functionalized polysiloxane has an average molecular weight of between about 900 and about 60,000 Da, for example, between about 1000 and about 50,000 Da, between about 1200 and about 25,000 Da, between about 1400 and about 20,000 Da, between about 1600 and about 15,000 Da, between about 1800 and about 10,000 Da, between about 2000 and about 5000 Da, between about 2200 and about 4000 Da, and between 2300 and about 2500 Da. In one embodiment, the average molecular weight of the hydride functionalized polysiloxane is about 2400 Da.

In some embodiments, the hydride functionalized polysiloxane has a percent SiH content of between about 3 and about 45%, for example, between about 5 and about 40%, between about 10 and about 35%, between about 20 and about 30%, or between about 26 and about 27%. In some embodiments, the hydride functionalized polysiloxane has a percent SiH content of about 26%.

In some embodiments, the hydride functionalized polysiloxane has an SiH content of between about 0.500 mmol/g and about 10.00 mmol/g, for example, between about 1.00 mmol/g and about 9.00 mmol/g, between about 2.00 and about 8.00 mmol/g, between about 3.00 mmol/g and about 7.00 mmol/g, and about 4.00 mmol/g and about 6.00 mmol/g. In one embodiment, the hydride functionalized polysiloxane has an SiH content of between about 4.00 and about 5.00 mmol/g, for example, 4.35 mmol/g.

In other embodiments, the hydride functionalized polysiloxane is alkyl terminated. The language "alkyl terminated" includes hydride functionalized polysiloxanes of formula III in which one or both of $R^{2b}$ and $R^{7b}$ are $C_{1-20}$ alkyl. In some embodiments, "alkyl terminated" includes hydride functionalized polysiloxanes of formula III in which one, two, three, four, five or six of $R^{1b}$, $R^{2b}$, $R^{3b}$, $R^{6b}$, $R^{7b}$ and $R^{8b}$ are $C_{1-20}$ alkyl. In one embodiment, $R^{1b}$, $R^{2b}$, $R^{3b}$, $R^{4b}$, $R^{5b}$, $R^{6b}$, $R^{7b}$, $R^{8b}$ and $R^{10b}$ are each $C_{1-20}$ alkyl, for example, $C_1$ alkyl (e.g., methyl) and $R^{9b}$ is hydrogen. In one embodiment, $R^{1b}$, $R^{2b}$, $R^{3b}$, $R^{4b}$, $R^{5b}$, $R^{6b}$, $R^{7b}$, $R^{8b}$ and $R^{9b}$ are each $C_{1-20}$ alkyl, for example, $C_1$ alkyl (e.g., methyl) and $R^{10b}$ is hydrogen.

In some embodiments, the hydride functionalized polysiloxane is selected from the group consisting of hydride terminated polydimethylsiloxane; polyphenyl-(dimethylhydrosiloxy)siloxane, hydride terminated; methylhydrosiloxane-phenylmethylsiloxane copolymer, hydride terminated; methylhydrosiloxane-dimethylsiloxane copolymers, trimethylsiloxy terminated; polymethylhydrosiloxanes, trimethylsiloxy terminated; polyethylhydrosiloxane, triethylsiloxane, methylhydrosiloxane-phenyloctylmethylsiloxane copolymer; methylhydrosiloxane-phenyloctylmethylsiloxane terpolymer and combinations thereof.

In some embodiments, the reactive constituent comprises combinations of polymers of formulas I, II, IIa, IIb, IIc, IId, and/or III. In a specific embodiment, the reactive constituent comprises a combination of polymers of formulas IIa, IIb, IIc and/or III. In a specific embodiment, the reactive constituent comprises a combination of polymers of formulas IIb, IIc and III.

In some embodiments, the reactive constituent comprises combinations of high molecular weight vinyl organopolysiloxanes, low molecular weight vinyl organopolysiloxanes, and/or hydride-functionalized organopolysiloxanes. In one embodiment, each of the high and low molecular weight organopolysiloxanes includes on average at least two vinyl moieties per polymer. In a specific embodiment, each vinyl organopolysiloxane includes exactly two vinyl moieties. In one embodiment, the ratio of the high molecular organopolysiloxane to the low molecular weight organopolysiloxane is 2 to 3, for example 2, 2.5 or 3. The ratio may be selected in order to adjust the chemical and physical properties of the film in order to suit a specific method or part of the body. In one embodiment, the hydride-functionalized organopolymer includes on average greater than two Si—H units in the polymer. In a specific embodiment, there are 8 Si—H units per hydride-functionalized organopolysiloxane.

In some embodiments, the reactive constituent comprises combinations of high molecular weight hydride-functionalized organopolysiloxanes, low molecular weight hydride functionalized organopolysiloxanes, and/or vinyl organopolysiloxanes. In one embodiment, each of the high and low molecular weight organopolysiloxanes include on average at least two Si—H units per polymer. In a specific embodiment, each hydride-functionalized organopolysiloxane includes exactly two Si—H moieties. In one embodiment, the ratio of the high molecular organopolysiloxane to the low molecular weight organopolysiloxane is 2 to 3, for example 2, 2.5 or 3. The ratio may be selected in order to adjust the chemical and physical properties of the film in order to suit a specific method or part of the body. In one embodiment, the vinyl organopolymer includes on average greater than at least two vinyl units in the polymer. In a specific embodiment, there are 8 vinyl units per vinyl organopolysiloxane.

The language "reinforcing constituent" includes one or more constituents of the reactive reinforcing component that provide the required physical properties of the film that results from the in situ reaction between the reactive reinforcing component and the cross-linking component. Such physical properties include, for example, mechanical elements (e.g., elasticity, durability, fracture strain, tensile strength, etc. . . . ), biocompatibility (e.g., selective breathability, adhesion, etc. . . . ), optical effects (e.g., reflectance, color, etc. . . . ) and surface modulation (e.g., texture, chemistry, etc. . . . ). Examples of reinforcing constituents include clays, (e.g., $Al_2O_3$, $SiO_2$), chalk, talc, calcite (e.g., $CaCO_3$), mica, barium sulfate, zirconium dioxide, zinc sulfide, zinc oxide, titanium dioxide, aluminum oxide, silica aluminates, calcium silicates, or optionally surface treated silica (e.g., fumed silica, hydrated silica or anhydrous silica). In some embodiments, reinforcing constituent is silica, for example, surface treated silica, such as silica treated with hexamethyldisilazane.

In some embodiments, the reinforcing constituent has a surface area of between about 100 and about 300 m²/g, for example, between about 110 and about 250 m²/g, between about 120 and about 225 m²/g, between about 130 and about 200 m²/g, between about 135 and about 185 m²/g, between about 160 and about 170 m²/g, and between about 164 and about 166 m²/g. In one embodiment, the reinforcing constituent has a surface area of about 160±25 m²/g.

In some embodiments, the reinforcing constituent has an average particle size of between about 1 and about 20 μm.

In some embodiments, the reinforcing constituent is compounded with the low viscosity and/or the high viscosity organopolysiloxane.

In some embodiments, reactive constituent and reinforcing constituent comprise between about 20 and about 90% of the reactive reinforcing component, for example, between about 40% and about 60% of the reactive reinforcing component. In some embodiments, the reactive constituent and reinforcing constituent comprise between about 45.0 and about 61.0% of the reactive reinforcing component, for example, about 45.0%, about 45.5%, about 46.0%, about 46.5%, about 47.0%, about 47.5%, about 48.5%, about 49.0%, about 49.5%, about 50.0%, about 50.5%, about 51.0%, about 51.5%, about 52.0%, about 52.5%, about 53.0%, about 53.5%, about 54.0%, about 54.5%, about 55.0%, about 55.5%, about 56.0%, about 56.5%, about 57.0%, about 58.0%, about 58.5%, about 59.0%, about 59.5%, about 60.0%, or about 60.5%. In some embodiments, the reactive constituent and the reinforcing constituent comprise about 45% of the reactive reinforcing component. In one embodiment, the reactive constituent and reinforcing constituent comprise about 48.0% of the reactive reinforcing component. In some embodiments, the reactive constituent and the reinforcing constituent comprise about 50.0% of the reactive reinforcing component. In another embodiment, the reactive constituent and reinforcing constituent comprise about 51.0% of the reactive reinforcing component. In some embodiments, the reactive constituent and the reinforcing constituent comprise about 51.5% of the reactive reinforcing component. In another embodiment, the reactive constituent and reinforcing constituent comprise about 54.5% of the reactive reinforcing component. In another embodiment, the reactive constituent and reinforcing constituent comprise about 55.0% of the reactive reinforcing component. In some embodiments, the reactive constituent and the reinforcing constituent comprise about 59.5% of the reactive reinforcing component. In another embodiment, the reactive constituent and reinforcing constituent comprise about 60.5% of the reactive reinforcing component. In some embodiments, the reactive constituent and reinforcing constituent comprise between about 30.0 and about 40.0% of the reactive reinforcing component, for example, about 30.0%, about 30.5%, about 31.0%, about 31.5%, about 32.0%, about 32.5%, about 33.0, about 33.5%, about 34.0%, about 34.5%, about 35.0%, about 35.5%, about 36.0%, about 36.5%, about 37.0%, about 37.5%, about 38.0%, about 38.5%, about 39.0%, about 39.5%, about 40.0%. In some embodiments, the reactive constituent and reinforcing constituent comprise between about 33.0 and about 40.0% of the reactive reinforcing component In one embodiment, the reinforcing constituent comprises between about 8.0 and about 13.0% of the reactive reinforcing component, for example, about 8.5%, about 9.0%, about 9.5%, about 10.0%, about 10.5%, about 11.0%, about 11.5%, about 12.0% or about 12.5%. In some embodiments, the reinforcing constituent comprises about 8.5% of the reactive reinforcing component. In one embodiment, the reinforcing constituent comprises about 9.0% of the reactive reinforcing component. In another embodiment, the reinforcing constituent comprises about 9.5% of the reactive reinforcing component. In some embodiments, the reinforcing constituent comprises about 10.0% of the reactive reinforcing component. In some embodiments, the reinforcing constituent comprises about 10.5% of the reactive reinforcing component. In another embodiment, the reinforcing constituent comprises about 11.0% of the reactive reinforcing component. In another embodiment, the reinforcing constituent comprises about 12.0% of the reactive reinforcing component. In another embodiment, the reinforcing constituent comprises about 13.0% of the reactive reinforcing component.

In another embodiment, the reactive constituent comprises between about 30.0 and about 60.0% of the reactive reinforcing component, for example, about 30.5%, about 31.0%, about 32.0%, about 33.0%, about 34%, about 35.0%, about 36.0%, about 37.0%, about 38.0%, about 39.0%, about 40.0%, about 41.0%, about 42.0%, about 43.0%, about 44.0%, about 45.0%, about 46.0%, about 47.0%, about 48.0%, about 49.0%, about 50.0%, about 51.0%, about 52.0%, about 53.0%, about 54.0%, about 55.0%, about 56.0%, about 57.0%, about 58.0% or about 59.0%.

In some embodiments, the reactive reinforcing component has a viscosity of between about 5,000 and 1,000,000 cSt or cP at 25° C. In some embodiments, the reactive reinforcing component has a viscosity of between about 10,000 and 10,000,000 cSt or cP at 25° C., for example, about 10,000,000, about 9,000,000, about 8,000,000, about 7,000,000, about 6,000,000, about 5,000,000, about 4,000,000, about 3,000,000 or about 2,000,000, about 1,000,000, about 900,000, about 800,000, about 700,000, about 600,000, about 500,000, about 400,000, about 300,000, about 200,000, about 100,000, about 90,000, about 80,000, about 70,000, about 60,000, about 50,000, about 40,000, about 30,000, about 20,000, about 10,000 cSt. In one embodiment, the reactive reinforcing component has a viscosity of about 1,000,000 cSt.

In some embodiments, the reactive reinforcing component has a vinyl to functional hydride (e.g., —CH═CH$_2$ of the one or more organopolysiloxanes to Si—H of the hydride functionalized polysiloxane) ratio of between about 1:10 and about 1:100, for example, between about 1:15 and about 1:90, between about 1:20 and about 1:80, between about 1:25 and about 1:70, between about 1:30 and about 1:60, between about 1:35 and about 1:50. In one embodiment, the reactive reinforcing component has a vinyl to functional hydride ratio of about 1:40. In another embodiment, the reactive reinforcing component has a vinyl to functional hydride ratio of about 1:20. In some embodiments, the reactive reinforcing component has a vinyl to functional hydride ratio of about 1:15.

The language "cross-linking component" includes a component that, when applied to the reactive reinforcing component, catalyzes the in situ formation of the body corrective film.

The term "catalyzes the in situ formation of the body corrective film" includes causing a reaction to occur between the reactive constituents of the reactive reinforcing component, such that a body corrective film is formed on the skin. Without being bound by theory, the cross-linking component induces a reaction between the one or more organopolysiloxanes and the hydride functionalized polysiloxane of the reactive reinforcing component causing the condensation of these constituents, such that a film is formed upon the skin.

In some embodiments, the cross-linking component comprises a metal catalyst, for example, a platinum catalyst, a rhodium catalyst or a tin catalyst. Examples of platinum catalysts include, for example, platinum carbonyl cyclovinylmethylsiloxane complexes, platinum divinyltetramethyldisiloxane complexes, platinum cyclovinylmethylsiloxane complexes, platinum octanaldehyde/octanol complexes and combinations thereof. An example of a rhodium catalyst includes Tris (dibutylsulfide) Rhodium utichloride. Examples of tin catalysts include tin II octoate, Tin II neodecanoate, dibutyltin diisooctylmaleate, Di-n-butylbis (2,4 pentanedionate)tin, di-n-butylbutoxychlorotin, dibutyltin dilaurate, dimethyltin dineodecanoate, dimethylhydroxy (oleate)tin and tin II oleate.

In some embodiments, the cross-linking component further comprises a vinyl terminated organopolysiloxane (e.g., a compound of Formula I, II IIa, IIb or IIc). In some embodiments, the amount of vinyl-terminated polysiloxane is a stabilizing amount of vinyl-terminated polysiloxane. The language "stabilizing amount" includes an amount that prevents the degradation of the catalyst and/or the cross-linking component and/or the body corrective film. In some embodiments, the stabilizing amount of vinyl-terminated polysiloxane is less than about 50%, less than about 40%, less than about 30%, less than about 20%, less than about 10%, less than about 5% or less than about 2%. In some embodiments, the stabilizing amount of vinyl-terminated polysiloxane is about 1%.

In some embodiments, the cross-linking component has a viscosity of between about 1,000 and about 50,000 cSt or cP at 25° C.

In some embodiments, the catalyst is added as a solution and the solution comprises between about 1.0 and about 5.0% of the cross-linking component, for example, about 1.5%, about 2.0%, about 2.5%, about 3.0%, about 3.5%, about 4.0% or about 4.5%. In one embodiment, the catalyst is about 2.0% of the cross-linking component.

In some embodiments, the catalyst comprises between about 0.005 and about 0.04% of the cross-linking component, for example, about 0.005%, about 0.010%, about 0.015%, about 0.020%, about 0.025%, about 0.030% or about 0.035% or about 0.040%. In one embodiment, the catalyst is about 0.02% of the cross-linking component.

In some embodiments, the catalyst is present in the cross-linking component in an amount of between about 100 ppm and about 500 ppm.

In some embodiments, the reactive reinforcing component and the cross-linking component are prevented from coming into contact prior to use. The reactive reinforcing component and the cross-linking component can be kept from coming into contact prior to use by usual means known to one of skill in the art. In one embodiment, the skin corrective formulation is a two part formulation in which the reactive reinforcing component and said cross-linking component are packaged in separate containers and mixed prior to use. In another embodiment, the reactive reinforcing component is applied to the skin first, and the cross-linking component is applied on top of the reactive reinforcing component. In yet another embodiment, the cross-linking component is applied to the skin first and the reactive reinforcing component is applied on top of the cross-linking component. In a further embodiment, the reactive reinforcing component and the cross-linking component are packaged together in the same container with a barrier between the two components, and are mixed when the components are extracted from the container.

The term "body" includes any part of the subject's body that can benefit from the formulations disclosed herein. Examples of the subject's body include the skin, the neck, the brow, the jowls, the eyes, the hands, the feet, the face, the cheeks, the breasts, the abdomen, the buttocks, the thighs, the back, the legs, the ankles, cellulite, fat deposits, and the like.

The term "skin" includes the epidermis of the subject's skin, which is the outer layer of the skin and includes the stratified squamous epithelium composed of proliferating basal and differentiated suprabasal keratinocytes.

The term "subject" includes subjects in which the formulations disclosed herein would be appropriate for use. In one example, the subject is a mammal, for example, a human. In another embodiment, the subject is suffering from skin imperfections, body imperfections, or has recently undergone a cosmetic procedure. In another embodiment, the subject desires to look younger or wishes to enhance his/her body.

In one embodiment, the body corrective formulation further comprises one or more of feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, pigments, cosmetic agents or therapeutic agents. In other embodiments, the reactive reinforcing component and/or the cross-linking component further comprise one or more of feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, pigments, cosmetic agents or therapeutic agents. One of skill in the art could readily determine further appropriate additives based on the INCI dictionary, which is incorporated herein by reference in its entirety.

Examples of cosmetic or therapeutic agents include sunscreens (for example, UV protecting agents) anti-aging agents, anti-acne agents, anti-wrinkle agents, spot reducers, moisturizers, anti-oxidants, vitamins.

In some embodiments, the emulsifier is SIMULGEL™ 400.

In some embodiments, the composition or film is administered first, followed by administration of the one or more additional cosmetic or therapeutic agents. In some embodiments, the composition or film is administered after the one or more additional cosmetic or therapeutic agents. In some embodiments, the film and the one or more additional cosmetic or therapeutic agents are administered substantially at the same time. In some embodiments, the composition or film is used to deliver the one or more additional cosmetic or therapeutic agents.

In some embodiments, a finishing formulation may be applied to the body corrective formulation during or after formation of the film on the body. The term "finishing formulation" includes a composition comprising components that provide a desired tactile sensation or a desired aesthetic look to the film after formation. For example, the finishing formulation may provide a silky, soft and/or smooth tactile sensation or a dewy, fresh, matte, shiny or luminescent aesthetic look after application to the film.

In some embodiments, the finishing formulation comprises one or more of oils, esters or ethers, for example, triglycerides, PPG-3 benzyl ether myristate, Schercemol DISD ester, or particles, for example, nylon, silica and silicone elastomer beads. In some embodiments, the one or more of these components comprise from about 0.5% to about 100% of the finishing formulation.

In some embodiments, the finishing formulation is a cream, spray, foam, ointment, serum, gel or powder.

In some embodiments, the finishing formulation further comprises one or more f feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, pigments, dyes (e.g., fluorescent dyes), cosmetic agents or therapeutic agents.

In some embodiments, the films and formulations described herein comprise one or more pigments. The include natural or non-natural coloring agents or dyes. In one embodiment, the pigments are fluorescent dyes.

In some embodiments, the films and formulation further comprise a pigment dispersion formulation. The language "pigment dispersion formulation" includes a formulations that are capable of providing one or more pigments to the films or formulations as a separate component of the formulation or film. In some embodiments, the pigment dispersion formulation allows for an even distribution of the pigment in the films and formulations. In some embodiments, the pigment dispersion formulation comprises at least one reactive constituent. In some embodiments, the pigment dispersion formulation comprises at least one reinforcing constituent. In some embodiments, the pigment dispersion formulation comprises one or more of feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, pigments, cosmetic agents or therapeutic agents. In other embodiments, the reactive reinforcing component and/or the cross-linking component further comprise one or more of feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, pigments, cosmetic agents or therapeutic agents.

In some embodiments, the pigment dispersion formulation is applied prior to or after the application of the reactive reinforcing component to the skin. In some embodiments, the pigment dispersion formulation is applied prior to or after the application of the cross-linking component to the skin. In some embodiments, the pigment dispersion formulation is applied in between the application of the reactive reinforcing component and the cross-linking component to the skin.

In some embodiments, the pigment dispersion formulation may be applied to skin that has not been subjected to the application of a body corrective formulation or film. For example, a subject may apply the pigment dispersion formulation to the skin in the area around the body corrective film or formulation, or the subject may apply the pigment formulation to the skin in lieu of applying the body corrective film or formulation.

The terms "apply," "applied" and "application" includes methods to administer the formulations disclosed herein to a subject's body, such as application by fingers, brush, cotton ball, pad, spray, sponge, cotton swab, roll-on and the like. One of skill in the art can readily determine appropriate methods to apply the formulations disclosed herein.

In some embodiments, the invention pertains, at least in part, to a kit comprising a body corrective formulation comprising a reactive reinforcing component and a cross-linking component. In some embodiments, the kit is a multi-compartment kit comprising at least two compartments in which one compartment comprises the reactive reinforcing component and the second compartment comprises the cross linking component. In some embodiments, the kit further comprises instructions for use of the kit, one or more brushes, one or more swabs, a film removing cleanser or a mirror. In some embodiments, the kit further comprises one or more finishing formulations.

In some embodiments, the invention pertains, at least in part, to a body corrective film prepared by a process comprising the steps of applying a reactive reinforcing component to the body; and applying a cross-linking component to the reactive reinforcing component, in which the cross-linking component catalyzes an in situ cross-linking of the reactive reinforcing component.

In some embodiments, the invention pertains, at least in part, to a body corrective film prepared by a process comprising the steps of applying a cross-linking component to the body; and applying a reactive reinforcing component to the cross-linking component, in which the cross-linking component catalyzes an in situ cross-linking of the reactive reinforcing component.

The language "body corrective film" includes films that are formed upon the reaction of the reactive reinforcing component and the cross-linking component and that, upon formation, ameliorate one or more body imperfections. In some embodiments, the body corrective film is a skin corrective film (e.g., a film that ameliorates one or more skin imperfections).

In some embodiments, the body corrective film has an appearance of natural skin upon application to the skin. The language "appearance of natural skin" includes the perception that the body corrective film, when applied to the skin, has the look, feel and texture of real skin and that the film treated skin has the physical properties (e.g., the elasticity and stiffness) of real (e.g., live) skin. A trained observer and/or a technician would be able to determine whether the film upon application to the body has the appearance of natural skin. For example, a trained observer would be able to determine whether the film, upon application to the body, appears excessively shiny, as described in Example 3, or whether the film appears not to move with the underlying musculature of the skin by, for example, breaking, buckling or deforming, in response to natural skin motion.

A technician would be able to determine whether the film has the appearance of natural skin upon application to the body. For example, the elasticity and stiffness of skin, with or without the body corrective film applied to it, can be assessed by a wide variety of methods (Agache et al., *Arch. Dermatol. Rev.*, 269 (1980) 221, the teachings of which are incorporated herein by reference). For example, the Derma-Lab suction cup instrument provides one common method to assess the mechanical properties of skin, and has previously shown younger skin to be less stiff and more elastic than aged skin (Grahame et al. *Clinical Science* 39 (1970) 223-238, the teachings of which are incorporated herein by reference). With this method, the stiffness of the skin is indicated by the Young's Modulus, a measure calculated by the instrument based on the pressure required to suck skin up a predetermined distance.

In some embodiments, the Young's Modulus of the skin treated with a body corrective formulation is reduced by between about 5% to about 70%, for example, between about 30% and about 60%, or between about 40% and about 50% compared to untreated skin. In some embodiments, the Young's Modulus of skin treated with a body corrective formulation is reduced by between about 5% and about 25% compared to untreated skin.

The elasticity of the skin is determined by the skin retraction time. The retraction time is obtained by measuring the time it takes for the skin to drop a predetermined distance towards its natural position, after the suction pressure is removed. In some embodiments, the retraction time of skin treated with a body corrective formulation is decreased by between about 5% and about 75%, for example, between about 30% and about 60%, or about 50% and about 65% when compared to untreated skin. In some embodiments, the retraction time of skin treated with a body corrective formulation is decreased by between about 5% and about 10% compared to untreated skin. In some embodiments, the retraction time of the skin treated with the film approaches the retraction time of the film alone.

Figure 2:
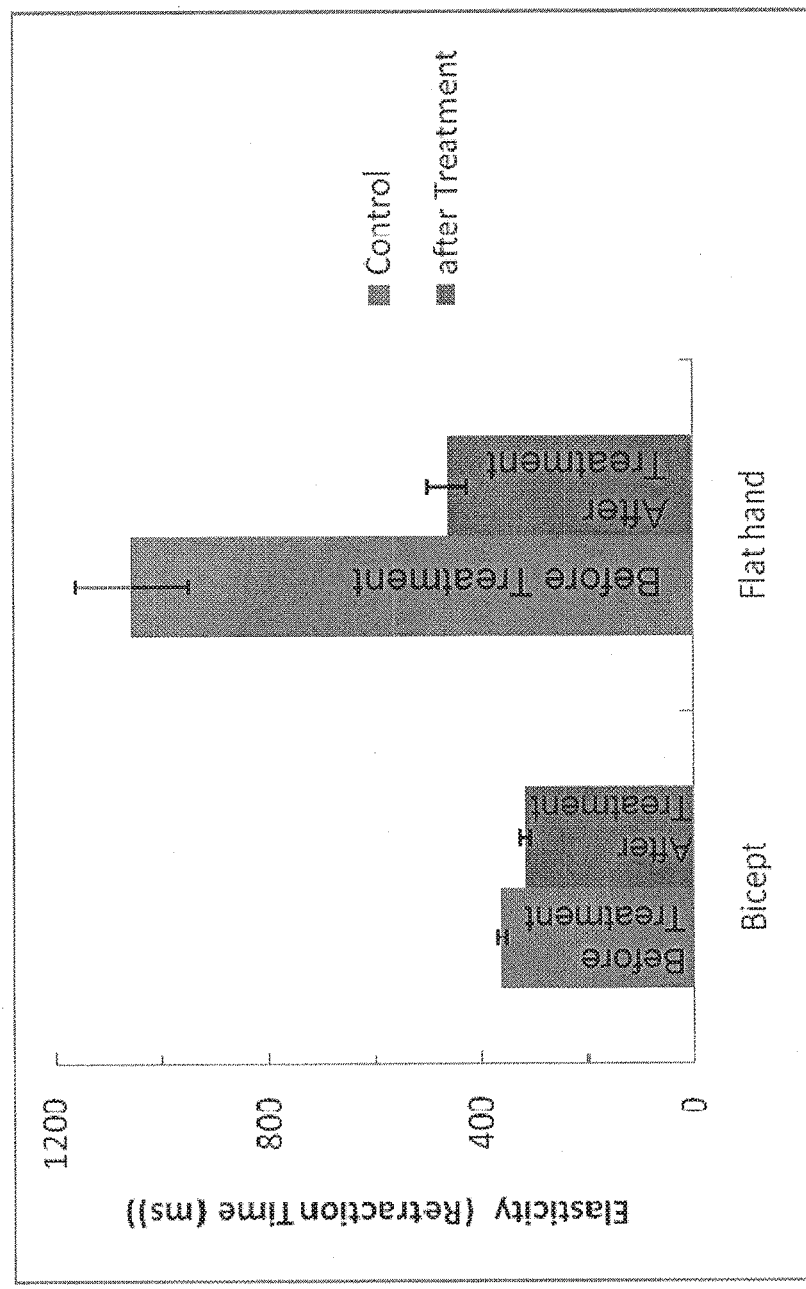
FIG. 2 is a chart illustrating the change in the retraction time after application of a formulation of the invention. The change in the retraction time indicates that the skin is more elastic upon application of the formulation.

The skin of the bicep and hand was evaluated before and after the body corrective treatment was applied, as shown in FIGS. 1 and 2. The DermaLab results confirmed that the skin was less stiff (FIG. 1) and more elastic (FIG. 2) after product application. The observed reduction in stiffness and the increase in skin elasticity are consistent with skin being more youthful.

In some embodiments, the body corrective film, upon application to the skin, has the appearance and physical properties of youthful, unblemished natural skin. The language "youthful skin" includes skin that has mild or no damage, as measured by the Griffith's score. The Griffith's score (GS), as shown below, is a quantitative measurement of the amount of skin damage subject has.

0-1: No damage
2-3: Mild damage
4-5: Moderate damage
6-7: Moderate to severe damage
8-9: Severe damage In some embodiments, youthful skin includes skin that has a Griffith's score of between about 0 and about 3.

In some embodiments, the subject has a negative change in Griffith's score ($\Delta$GS) of about 1, about 2, about 3, about 4, about 5, about 6, about 7 or about 8 after application of the body corrective formulation. In some embodiments, the subject has a $\Delta$GS of between about −0.5 and about −3.0 upon application of the body corrective formulation. In one embodiment, the subject has a $\Delta$GS between about −1 and about −1.5, between about −1.2 and about −1.3 (e.g., about −1.25) upon application of the body corrective formulation. In another embodiment, the subject has a $\Delta$GS of between about −2.0 and about −3.0, for example, between about −2.0 and about −2.5, or between about −2.1 and about −2.2 (e.g., about −2.15) upon application of the body corrective formulation.

One of skill in the art would be able to determine whether the film, upon application to the body, has the appearance of youthful, unblemished natural skin by the methods disclosed in Example 6.

In other embodiments, the film, upon application to the skin, provides stiffness and elasticity such that the skin treated with the film appear substantially more similar to youthful skin than untreated skin. The term "elasticity" includes the skin's tendency to return to its original shape once it's been deformed. The language "elasticity substantially similar to youthful skin" includes the ability of the skin to return to its original shape once it's been deformed in a manner similar to that of young skin. The term "stiffness" includes the skin's resistance to deformation. The language "stiffness substantially similar to youthful skin" includes the ability of the skin to resist deformation in a manner similar to that of young skin. A technician would also be able to determine whether the film, upon application to the body, has the aforementioned physical properties of youthful, unblemished, natural skin by the techniques described above (e.g., using the Dermalab suction cup instrument).

In some embodiments, the subject and/or observers of the subject perceive an age reduction upon application of the body correction formulation. In some embodiments, the perceived age reduction is about 1 year, about 2 years, about 3 years, about 4 years, about 5 years, about 6 years, about 7 years, about 8 years, about 9 years, about 10 years, about 11 years, about 12 years, about 13 years, about 14 years or about 15 years less than the subject's actual age. In some embodiments, the perceived age reduction is about 7.5 years less than the subject's actual age upon application of the body corrective formulation. In other embodiments, the perceived age reduction is about 8.5 years less than the subject's actual age upon application of the body corrective formulation.

The language "the film is formed" and "film formation" includes the results of the polymerization reaction that occurs upon the interaction of the reactive reinforcing component and the cross-linking component. Without being bound by theory, film formation is characterized by a phase transition from the viscous sol state of a mixture to that of a continuous interconnected polymer state of film.

A technician could determine when the film is formed on the body by using routine methods. For example, rheological measurements using small amplitude oscillatory shear can determine the continuous evolution of the viscoelastic properties, such as elastic modulus (G'), the viscous modulus (G") and the loss of tangent (tan $\delta$) of the reacting mixture continuously through the film formation process. In some embodiments, the rheometer can be used to determine the cross over time between G' and G" and the time when tan $\delta$ becomes frequency independent, which is a measure of film formation. In some embodiments, the film is formed within at least about five minutes, for example, within about one minute, about two minutes, about three minutes or about four minutes. In some embodiments, the film is formed within at least about 10 seconds and about 3 minutes.

In some embodiments, the skin or body corrective film has a Young's Modulus (e.g., tensile strength) of between about 0.01 and about 1 MPa, as illustrated in Example 1.

In some embodiments, the fracture strain of the skin or body corrective film has a fracture strain of at least about 150%, as measured by Example 1.

In some embodiments, the skin or body corrective film has a leather adhesive force of greater than about 20 N/mm, for example, greater than about 25 N/mm, greater than about 30 N/mm, greater than about 35 N/mm, greater than about 40 N/mm, greater than about 45 N/mm, greater than about 50 N/mm, greater than about 55 N/mm, greater than about 60 N/mm, greater than about 65 N/mm, greater than about 70 N/mm, greater than about 75 N/mm, or greater than about 80 N/mm, as determined by the leather adhesion test illustrated in Example 2. In one embodiment, the leather adhesive force is between about 50 and about 80 N/mm, as determined by the leather adhesion test illustrated in Example 2.

In some embodiments, the skin or body corrective film has a hysteresis of less than about 10% for example, least than about 9%, less than about 8%, less than about 7%, less than about 6%, less than about 5%, less than about 4%, less than about 3%, less than about 2%, less than 1% or about 0%.

In some embodiments, the skin or body corrective film is between about 10 µm and about 1500 µm thick, for example, between about 50 µm and about 500 µm thick. In some embodiments, the film is less than about 100 µm thick. The film thickness may be measured by methods known to one of skill in the art, for example, by the combination of calipers and a calibrated microscope. The thickness of the film may also be digitally measured from a micrograph of the film cross-section. The microscope calibration allows for the conversion of measured pixelar distance into metric distance units.

In some embodiments, the skin or body corrective film shrinks by less than between about 1 and 30%, for example, between about 1 to about 15%. The amount of shrinking may be determined by methods known to one of skill in the art, for example, by the Croll method (Croll, S. G. *J. Coatings Tech.* 52 (1980) 35, the teachings of which are incorporated herein by reference). In this method the film is used to coat one side of a thin flexible substrate. The amount of curve developed in the substrate due to the shrinking of the coating is used to calculate the magnitude of shrinking of the coating (Francis et al., *J Mater Sci* 2002, 37:4717-31, the teachings of which are incorporated herein by reference.)

In some embodiments, the body corrective films are physiologically stable. The language "physiologically stable" includes the durability of the film upon exposure to normal skin conditions, for example, humidity, tears, sweat or sebum. The physiological stability may be determined by methods typically used by one of ordinary skill in the art, such as an uptake test, which measures the change in weight of the film after exposure to a physiological factor. For example, the uptake test may employ a formulation of simulated sweat (e.g., 1× phosphate buffered saline solution) or simulated sebum (e.g., 25% wax monoesters, 41% triglycerides, 16% free fatty acids and 12% squalene). In some embodiments, the weight of the film increases by less than about 10%, for example, less than about 9%, less than about 8%, less than about 7%, less than about 6%, less than about 5%, less than 4%, less than 3%, less than 2%, less than 1% or exhibits no increase upon exposure to humidity, tears, sweat or sebum.

In some embodiments, the invention pertains, at least in part, to methods for correcting body imperfections in a subject comprising applying to the subject a formulation comprising a) a first reactive reinforcing component; and a second cross-linking component; in which the cross-linking component catalyzes an in situ cross-linking of the reactive reinforcing component, such that a film is formed on the skin, thereby correcting body imperfections. The language "correcting body imperfections" includes ameliorating (e.g., partially or completely) one or more body imperfections, either permanently or temporarily (e.g., for the duration that the film is left on the skin). One of skill in the art would be able to determine whether the body imperfections are corrected, either partially or completely, upon application of the body corrective formulation to the body by the techniques described in Example 6.

In some embodiments, the language "correcting body imperfections" includes reducing the appearance of body imperfections in a subject comprising applying to the subject a formulation comprising a) a first reactive reinforcing component; and b) a second cross-linking component; in which the cross-linking component catalyzes an in situ cross-linking of the reactive reinforcing component, such that a film is formed on the skin, thereby reducing the appearance of skin or body imperfections. The language "reducing the appearance of body imperfections" includes the diminishment of one or more outward aspects of one or more body imperfections. In some embodiments, the appearance of the body imperfections upon application of the body corrective formulation to the subject are reduced by about 100%, by about 95%, by about 90%, by about 85%, by about 80%, by about 75%, by about 70%, by about 65%, by about 60%, by about 55%, by about 50%, by about 45%, by about 40%, by about 35%, by about 30%, by about 25%, by about 20%, by about 10% or by about 5% compared to the untreated subject.

In some embodiments, the language "correcting body imperfections" includes masking body imperfections in a subject comprising applying to said subject a formulation comprising a) a first reactive reinforcing component; and b) a second cross-linking component; wherein said cross-linking component catalyzes an in situ cross-linking of the reactive reinforcing component, such that a film is formed on the skin, thereby masking the appearance of body imperfections. The language "masking body imperfections" includes concealing or obscuring from view, either partially or completely, one or more body imperfections. In some embodiments, the method provides for masking body imperfections on a subject following a cosmetic procedure, comprising applying to the skin where the cosmetic procedure was performed a formulation comprising a) a first reactive reinforcing component; and b) a second cross-linking component; wherein said cross-linking component catalyzes an in situ cross-linking of the reactive reinforcing component, such that a film is formed on the skin, thereby masking the appearance of body imperfections. Examples of cosmetic procedures include, for example, cosmetic surgery (e.g., eye lift, face lift, tummy tuck and the like) or Botox® injections. In some embodiments, skin imperfections are masked. In some embodiments, the body imperfections after application of the body correcting formulation are masked by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100% compared to the untreated body imperfections.

In some embodiments, the language "correcting body imperfections" includes improving the appearance of a subject's body, comprising applying to said subject a formulation comprising a) a first reactive reinforcing component; and b) a second cross-linking component; wherein said cross-linking component catalyzes an in situ cross-linking of the reactive reinforcing component, such that a film is formed on the skin, thereby improving the appearance of the body. The language "improving the appearance of a subject' body" includes enhancing the outward aspect of the body. Examples of improving the appearance of the body include reducing or masking the appearance of port wine stain or nevus flammeus (e.g., nevus flammeus nuchae or midline nevus flammeus) melasma, wrinkles, scars, moles, acne, skin disfigurements, birth marks, burn wounds, blemishes or pores, evening skin tone, reducing or masking shine, lifting sagging skin, or reducing or masking the appearance of cellulite or stretch marks. In some embodiments, the appearance of the subject's skin is improved.

In some embodiments, the language "correcting body imperfections" includes enhancing the body of a subject, comprising applying to the subject's body a formulation comprising a) a first reactive reinforcing compound; and b) a second cross-linking component, in which the cross-linking component catalyzes an in situ cross-linking of the reactive reinforcing component, such that a film is formed on the skin, thereby enhancing the subject's body. The language "enhancing the body" includes augmenting or heightening the features of a subject's body such that the subject's appearance is more attractive. For example, a subject's body may be enhanced by the addition of colorants, glitter and the like. In some embodiments, the appearance of the subject's skin is enhanced.

In some embodiments, the invention pertains, at least in part, to methods of reducing the appearance of a subject's age comprising applying to the subject a formulation comprising a) a first reactive reinforcing component; and b) a second cross-linking component; in which the cross-linking component catalyzes an in situ cross-linking of the reactive reinforcing component such that a film is formed on the skin, thereby reducing the appearance of a subject's age. The language "reducing the appearance of a subject's agent" includes the perception by the subject or those viewing the subject that the subject is younger upon application of the body corrective film to the subject. In some embodiments, the subject appears about 1 year, about 2 years, about 3 years, about 4 years, about 5 years, about 6 years, about 7 years, about 8 years, about 9 years, about 10 years, about 11 years, about 12 years, about 13 years, about 14 years, about 15 years, about 16 years, about 17 years, about 18 years, about 19 years or about 20 years younger upon application of the body corrective film.

In some embodiments, the invention pertains, at least in part, to methods for protecting a subject's body comprising applying to the subject a formulation comprising a) a first reactive reinforcing component; and b) a second cross-linking component; in which the cross-linking component catalyzes an in situ cross-linking of the reactive reinforcing component such that a film is formed on the skin, thereby protecting the body. The language "protecting a subject's body" includes preserving or shielding a subject's skin or body from damaging environmental elements, for example, damage by the sun, wind, rain or environmental toxins. In some embodiments, the subject's skin is protected.

In some embodiments, the invention pertains, at least in part, to methods for shaping a subject's body, comprising applying to the subject a formulation comprising: a) a first reactive reinforcing component; and b) a second cross-linking component; in which the cross-linking component catalyzes an in situ cross-linking of the reactive reinforcing component such that a film is formed on the skin, thereby shaping or the body. The language "shaping a subject' body" includes altering the body of a subject, for example, by providing support to soft body tissues and preventing sagging of soft body tissues. Examples of soft body tissues include the abdomen, the thighs, the buttocks, the neck, the brow, the jowls, the breasts, the skin under the arms, and the skin surrounding the eyes. In some embodiments, the subject' skin is shaped.

In some embodiments, the language "shaping a subject's body" includes structurally altering by, for example, redistributing a portion of the subject's body, comprising applying to the subject a formulation comprising a) a first reactive reinforcing component; and b) a second cross-linking component; in which the cross-linking component catalyzes an in situ cross-linking of the reactive reinforcing component such that a film is formed on the skin, thereby shaping the body. In some embodiments, a portion of the subject's body is lifted, for example, the breasts, the skin, the buttocks, and the like. The language "lifting a subject's body" includes raising the subject's body, for example, in a manner similar to a surgical cosmetic procedure (e.g., a face lift, an eye lift, a breast lift and the like). In some embodiments, the subject's skin is lifted. In some embodiments, the skin is facial skin (e.g., the skin around the eyes, the skin on the brow or the skin surrounding the lips) or neck skin. In some embodiments, upon application of the body corrective formulation, the body is lifted by about 5%, about 10%, about 15%, about 20%, about 25%, about 30%, about 35%, about 40% or by about 50% compared to the subject's untreated body. In some embodiments, the body is lifted by about 1 mm, about 2 mm, about 3 mm, about 4 mm, about 5 mm, about 6 mm, about 7 mm, about 8 mm, about 9 mm, about 1 cm, about 1.5 cm, about 2.0 cm, about 2.5 cm, about 3.0 cm, about 3.5 cm, about 4.0 cm, about 4.5 cm, about 5.0 cm, about 5.5 cm, about 6.0 cm, about 6.5 cm, about 7.0 cm, about 7.5 cm, about 8.0 cm, about 8.5 cm, about 9.0 cm, about 9.5 cm or about 10 cm upon application of the body corrective film.

In some embodiments, the invention pertains, at least in part, to a method for delivering an agent to a subject, comprising applying to the subject's skin a formulation comprising a) a first reactive reinforcing component optionally comprising one or more agents; and b) a second cross-linking component optionally comprising one or more agents; in which the cross-linking component catalyzes an in situ cross-linking of the reactive reinforcing component such that a film is formed on the skin, thereby delivering the agent to the subject. The language "delivering an agent" includes releasing an agent (e.g., a cosmetic or therapeutic agent) to the skin of subject upon formation of the film on the subject's skin. In some embodiments, the agent is delivered in one portion, or the agent is formulated to be delivered in a time-release manner. Examples of agents include cosmetic agents and therapeutic agents.

In some embodiments, the invention pertains, at least in part, to a body corrective formulation for application to a subject's body, comprising at least one preselected function modulating component, wherein said composition forms a body corrective film upon application to the subject's body.

The term "preselected" includes components that are chosen prior to the preparation of the formulation. For example, the components may be chosen during the manufacturing process to create a specific formulation. Alternatively, the components may be chosen by the subject prior to application of the formulation.

The language "function modulating component" includes components that allow the body corrective formulations to be selectively adjusted for a particular use of the film (e.g., reducing the appearance of wrinkles, minimizing shine, masking pores, etc.). The function modulating component or components may be selected based on the physical properties of the film that are necessary to be effectively applied for a particular use of the film. For example, if the formulation will be used to minimize shine, the modulus should be low relative to the values of the other physical properties of the resulting film.

In some embodiments, the invention pertains, at least in part, to a body corrective formulation that targets a treatment area on a subject's body, comprising at least one preselected treatment specific component, wherein said composition forms a body corrective film upon application to the target treatment area on the subject's body.

The language "target treatment area" includes an area of the body where the formulation is meant to be applied.

The language "treatment specific component" includes components that allow the body corrective formulations to be selectively adjusted for a target treatment area on the body (e.g., under the eye, forehead, lips, buttocks, neck, etc. . . . ). The treatment specific component or components may be selected based on the physical properties of the film that results from the formulations that are necessary to be effectively applied to a target treatment area, as shown in Table 1. For example, if the target treatment area is under the eye, the modulus should be low relative to the values of the other physical properties of the resulting film.

TABLE 1

| Target Treatment Area | Modulus | Elasticity | Elongation | Adhesion | Matte Finish | Texture |
|---|---|---|---|---|---|---|
| Under the eye | Low | High | Medium | High | High | High |
| Forehead | High | High | Medium | High | High | High |
| Lips | Medium | High | High | High | Low | Low |

Examples of function modulating components and treatment specific components include a stiffness component, an elasticity component, an elongation component, an adhesive component, a matte component and a textural component.

The language "stiffness component" includes components that modulate the flexibility of the resulting film, which is determined by measuring the Young's Modulus of the film (see Example 2). Examples of stiffness components include the reactive constituent (e.g., organopolysiloxane and/or hydride functionalized polysiloxane) and the reinforcing constituent.

The language "elasticity component" includes components that modulate the recoil of the resulting film, which is determined by measuring the hysteresis, and includes, for example, the reinforcing constituent.

The language "elongation component" includes components that modulate the stretch of the resulting film, which is determined by measuring the percent elongation to yield. Examples of elongation components include the reactive constituent (e.g., organopolysiloxane and/or hydride functionalized polysiloxane) and the reinforcing constituent.

The language "adhesion component" includes components that modulate the adherence of the resulting film to the skin, as measured by the leather adhesive test (see Example 2). Examples of adhesion components include the reactive constituent (e.g., organopolysiloxane and/or hydride functionalized polysiloxane) and the reinforcing constituent.

The language "matte component" includes components that modulate the gloss of the resulting film, as measured by determining the shine of the resulting film (see Example 3). Examples of matte components include the reinforcing constituent and light scattering particles.

The language "textural component" includes components that modulate the texture of the film so that the resulting film has the look and feel of natural skin, and is measured by determining the friction of the film. One of skill in the art can readily determine methods to measure the friction of the film, for example, by pressing in and dragging a cantilever across the surface and recording the resisting force. Higher friction corresponds to higher recorded force and rougher surfaces tend to have higher friction.

In some embodiments, the invention pertains, at least in part, to a film removing cleanser for use in removing a body corrective film, wherein said film is prepared by a process comprising the steps of a) applying a reactive reinforcing component to skin; and b) applying a cross-linking component to said reactive reinforcing component, wherein said cross-linking component catalyzes an in situ cross-linking of the reactive reinforcing component.

In other embodiments, the invention pertains, at least in part, to a film removing cleanser comprising a film wetting component, a penetration component, a film swelling component and a film release component.

The language "film removing cleanser" includes a cosmetic formulation that, when applied to a body corrective film, breaks down the components of the film such that the film may be removed from the body. In some embodiments, the film cleanser removes the film by wetting the film, penetrating the film, swelling the film and releasing the film from the skin.

The language "film wetting component" includes those components of the cleanser that allow the film to absorb liquid. In some embodiments, the film wetting component comprises caprylyl methicone, ethyl trisiloxane or a combination thereof.

The language "penetration component" includes those components of the cleanser that allow the cleanser to permeate the film. Examples of penetration components include siloxane emulsifiers, caprylyl methicone, ethyl trisiloxane or a combination thereof.

The language "film swelling component" includes components of the cleanser which cause the film to expand. Examples of film swelling components include caprylyl methicone, ethyl trisiloxane, isododecane or a combination thereof.

The language "film releasing component" includes components of the cleanser that cause the film to not adhere to the skin or body of the subject to which the film is applied. Examples of film releasing components include glycols, water or a combination thereof.

In some embodiments, the cleanser disrupts the film's mechanical integrity. The language "disrupt the film's mechanical integrity" includes the disturbance of the mechanical features that provide the film its unique properties (e.g., the stiffness, elasticity, elongation, adhesion and the like).

In some embodiments, the cleanser comprises a siloxane phase, an emulsifier phase and an aqueous phase. The language "siloxane phase" includes a component of the cleanser that comprises one or more siloxanes, for example, caprylyl methicone and ethyl trisiloxane. In some embodiments, the siloxane phase also includes isododecane and Aerogel VM2270 (Dow Corning). The language "emulsifier phase" includes a component of the cleanser that comprises one or more emulsifiers, for example, siloxane emulsifiers such as lauryl PEG-9 polydiethylsiloxyethyl dimethicone, PEG-35 Castor oil, or isododecane and lauryl dimethicone/polyglycerin 3 cross polymer. The language "aqueous phase" includes a component of the cleanser that is soluble in water, for example, water, propylene glycol, butylenes diglycol, glycerol or combinations thereof. In some embodiments, the aqueous phase includes MPdiol glycol, preservatives (e.g., neolone PE), optical particles (e.g., silica and DMPA/isophthalic acid/SMDI copolymer & Green 5) and structural particles (e.g., nylon-12).

In some embodiments, the siloxane phase is about 50% of the cleanser, the emulsifier phase is about 8% of the cleanser and the aqueous phase is about 42% of the cleanser.

In some embodiments, the invention pertains, at least in part, to a method of cleaning a body surface having a body corrective film, comprising applying an effective amount of a film dissolving cleanser to the film, such that said film dissolves. In some embodiments, the body surface is the skin.

In some embodiments, the invention pertains, at least in part, to a formulation for repairing a body corrective skin applied to the skin in which the formulation comprises a) a first reactive reinforcing component and b) a second cross-linking component; wherein the cross-linking component catalyzes an in situ cross-linking of the reactive reinforcing component such that a film is formed on the skin.

The terms "repair" and "repairing" includes ameliorating imperfections in the body corrective film after formation of the film on the skin. In some embodiments, the term "repair"

includes mending or patching tears, gaps or breaks in the film. In some embodiments, the term "repair" includes replacing a portion of the film that may have been removed from the skin. In some embodiments, the term "repair" includes re-adhering or re-attaching a portion of the film that may have come loose from the skin (e.g. de-laminated from the skin). In some embodiments, the term "repair" includes swelling the edges of the tear, gap or break in the film to make the film more malleable, such that the film may be able to be reshaped.

In some embodiment, the invention pertains, at least in part, to a method for repairing a body corrective film applied to skin by a) identifying an area of the film in need of repair; b) optionally smoothing the edges of the film; and c) applying a formulation for repairing the film, wherein the formulation comprises a first reactive reinforcing component and a second cross-linking component; wherein the cross-linking component catalyzes an in situ cross-linking of the reactive reinforcing component such that a film is formed on the skin, thereby repairing the body corrective film.

The language "smoothing the edges of the film" includes removing, swabbing, swelling, brushing or grinding the edges of the film in the area in need of repair to remove jagged or uneven portions of the film.

In some embodiments, the invention pertains to a kit comprising a first reactive reinforcing component, and a second cross-linking component, wherein the cross-linking component catalyzes an in situ cross-linking of the reactive reinforcing component such that a film is formed on the skin. In some embodiments, the invention pertains, at least in part, to a kit for repairing a body corrective film in which the kit comprises a formulation comprising a) a first reactive reinforcing component and b) a second cross-linking component wherein the cross-linking component catalyzes an in situ cross-linking of the reactive reinforcing component such that a film is formed on the skin.

In some embodiments, the kit is a multi-compartment kit comprising at least two compartments. In some embodiments, the reactive reinforcing component is in one compartment and the cross-linking component is in a second compartment. In some embodiments, the kit further comprises one or more brushes, one or more swabs, a film removing cleanser, instructions for use or a mirror. In some embodiments, the kit further comprises a pigment dispersion formulation.

EXAMPLES

Example 1. Cyclic and Extension Pull Test

Sample Preparation:

For the purpose of bulk mechanical property determination, target materials were cast inside dumbbell shaped molds. The dimensions of the neck of the mold were 20 mm in length, 5 mm in width and 1.5 mm in depth. The "handles" of the mold were 20 mm by 15 mm and provided adequate area to insure secure slip-free grip during testing. The mold dimensions are consistent with the ASTM D638 guidelines.

Once the poured specimens were fully cured and dried, the formed samples were extracted from their individual molds by means of a spatula and the geometry of the finished pieces was measured with digital calipers to determine precise dimensions.

Mechanical Testing:

Mechanical characterization of specimens was carried out on the Instron 3342 (Instron, Norwood Mass.) equipped with 100N load-cell (Instron #2519-103). Dumbbell shaped samples were mounted onto the instrument via modified Instron 2710-101 grips which insured sample didn't slip or fail inside the grips during testing. Two types of tests were performed sequentially on each sample, first the Cyclic Test followed by the Extension Pull Test. It is noted that the first test (e.g., the cyclic test) had negligible effects on the result of the second test (e.g., the extension pull test). Each test was preprogrammed into Bluehill Lite Software used to operate the instrument. The parameters and data analysis associated with each of the two tests is described below.

Cyclic Test:

In order to determine the elasticity of the materials, a cyclic test was designed. The cyclic test was used to determine the most elastic (e.g., spring-like) material and an Instant Residual Strain (I.R.S.) was obtained from this test, as described below. Generally, the more elastic the material, the faster it returns to its original shape after deformation. For perfectly elastic materials, the I.R.S. and cycle test area approach zero, and therefore, the lower the value the better.

Prior to starting the test, a sample was mounted onto the instrument such that the rectangular handle portions of the specimen and none of the specimen neck were fixed within the instrument grips. The instrument grip distance was adjusted such that the sample was at neutral extension as indicated by the instrument force being close to zero (±0.01N). Subsequently, cyclic extension was performed at 1 mm/s to a maximum extension of 15% of initial sample length. A total of 15 cycles are executed and recorded. The stress strain data recorded by instrument was exported into Excel where the reported mechanical properties were calculated.

An Excel template was used to automatically extract a number of parameters. The cyclic Young's Modulus as calculated as the straight line slope of the stress-strain curve of first cycle between 1% and 4%. The R squared value of the linear fit was above 0.99 or the Young's Modulus was discarded. The Instant Residual Strain (I.R.S.) was calculated for each cycle as the strain difference between the loading and unloading curves at half the maximum stress achieved during the 1st cycle. The I.R.S. for the first cycle as well as the average I.R.S. for the 4th through 14th cycles were recorded. The area bound by the loading and unloading curves of each cycle was also calculated. Good agreement was observed between the I.R.S. and the calculated cycle area.

The majority of the materials evaluated were sufficiently flexible and elastic such that the Cyclic Test could be repeated on the same sample without a significant change in calculated properties. This suggests this test does not result in long lasting changes to the tested material.

Extension Pull Test:

The Extension Pull test was used to determine the stiffness and stretchiness of a material by measuring the Young's Modulus and Ultimate Strain. The Young's Modulus was utilized as a measure of material stiffness, while the Ultimate Strain was used as a measure of material flexibility. In order to develop a film with the appearance of skin, the Young's Modulus should fall within a target range (e.g., 0.1-1.0 MPa), while the fracture strain (as measured by the Ultimate Strain) should be sufficiently high (e.g., greater than about 150%) so that the film will not break when being deformed by skin movement.

The sample was mounted onto the instrument such that the rectangular handle portions of the specimen and none of the specimen neck were fixed within the instrument grips. The instrument grip distance was adjusted such that the sample was at neutral extension as indicated by the instrument force being close to zero (±0.01N). Subsequently, extension until sample failure was performed at 10 mm/s. The stress strain data recorded by instrument during the extension was exported to Excel where the reported mechanical properties were calculated.

An Excel template was used to automatically extract a number of parameters from the instrument generated data. The extension Young's Modulus (YM) as calculated as the straight line slope of the stress-strain curve between 6% and 11%. The R squared value of the linear fit was above 0.99 or the Young's Modulus was calculated from a more linear 5% strain range on the stress strain curve. The Shear Modulus (G) was determined from the same strain range as the YM. G was calculated as the slope of the best line fit between recorded stress and $\alpha$-$\alpha$-2, where $\alpha$ is 1 plus the instantaneous strain. The Yield strain was determined as the strain at which the measured stress differed by more than 10% from the Neo-Hookean stress; the multiple of G and ($\alpha$-$\alpha$-2). Ultimate Stress was calculated as the maximum stress recorded during the experiment. The mechanical property calculations presented here are consistent with ASTM D412.

Example 2: Leather T-Peel Adhesion Test

To determine adhesiveness of the target materials, the materials were spread onto a piece of soft flexible leather 25.4 mm wide and 76.2 mm long. The leather used as test substrate was light weight upholstery leather (AD1100 from Leather Unlimited, Belgium Wis.). Immediately after spreading the material onto the first piece of leather, a second equivalent piece of leather was placed on top to sandwich a thin layer of material between the two pieces. The two pieces of leather were pressed together to leave a thin homogeneous layer of material at the interface of the two leather substrates. The edges were wiped to remove access materials and the material was allowed to cure and dry to form a test specimen.

The adhesion test sample was partially pealed at one end by hand to separate enough of the two leather substrates for effective grip by Instron 3342 mounts. Each leather substrate was secured in its own instrument grip and an extension test was performed at a rate of 10 mm/s to peel the two substrates from each other. The force vs. time data was recorded by instrument during the extension and exported to Excel where the reported adhesive force was calculated.

An Excel template was used to automatically extract adhesive parameters from the instrument generated data. The sample average adhesive force was calculated by averaging the instantaneous force measured by the instrument during the experiment normalized by the sample width (25.4 mm). This test method was developed in accordance with ASTM D1876. The minimum acceptable adhesion, which depends on the stiffness of the material and the area on which the film is placed, was approximately greater than 25 N/mm

Example 3. Image Analyses Measures

Shine:

In order to measure shine, either in vitro or in vivo, a light box with a light source placed at a 45° angle relative to the site being measured was used to create shine, and a camera, positioned such that the angle formed by a line drawn from the lens to the area being measured is 45°, was used to photograph the site. The white balance, F-stop and ISO of the camera were manually fixed at set values to give adequate exposure and good color temperature. One picture was taken without any diffusing element between the light source and the site to capture the shine. Then, a diffusing surface was placed between the light source and site and another photograph was taken (altering shutter speed such that the exposure is similar or equal to the first photograph). This photograph captured the surface without any shine present while the first photograph captured the maximum amount of shine as a result of specular reflectance. These photographs were overlaid and cropped to the relevant sample area and then the diffused photograph was subtracted from the maximum shine photograph to create a photograph with only the shine highlights present. The entire subtracted photograph was then summarized by finding the average grey value along with the standard deviation. This average grey value was denoted as the shine value and was used to compare the amount of specular reflectance present in each sample. For each sample, the camera settings for each situation (with and without the diffuser) were identical.

Photo Set Up Capture:

To ensure maximum repeatability in panelist placement for every photograph taken for product performance evaluation, a Head Positioning System (HPS) was created. This HPS had two configurations: forehead-only evaluations and a whole face evaluation. In both configurations, a model 819 series table clamped chin-rest from Applied Science Laboratories (ASL) was used as a base to mount the two different configurations to a table. Two cameras were used to capture the subject from two different angles. The first camera (normal shot) was positioned face-on such that line of the lens through the camera was positioned relative to the plane of the subject's face at an angle of approximately 90°. A second camera (45° shot) was positioned to the subject's left such that the line of the lens through the camera was positioned relative to the plane of the subject's face at an angle of approximately 45° capturing primarily the left side of the subject's face. The position of the cameras relative to the chin-rest was kept fixed.

In the first configuration, an ASL cheek-rest (819-2155) was mounted to the ASL chin-rest. In this setup, the panelist's head was positioned such that the line formed from the center of the camera lens to the area of evaluation is normal to the area of evaluation on the forehead. In the second configuration, an ASL forehead-rest (819-2150) was attached to the chin-rest. In this setup, the chin-rest cup was positioned such that the horizontal bar on the forehead-rest was situated at the panelist's horizontal hairline, maximizing the area of evaluation in every photograph.

Lighting for the photography consisted of two Calumet Quattro fluorescent lamps (CF0003) with four Calumet 35 Watt 5500K daylight color temperature fluorescent lights (OL2003) placed in front of and on either side of the panelist, angled to point directly at the panelist. A glare stop polarizing filter from Visual Pursuits, Inc. was also placed on the front of each lamp. The lights were allowed to warm up for at least 10 minutes prior to taking any photographs. In addition to the lighting, a circular polarizing filter was used on each of the camera lenses to control the type of light in each photograph.

For each evaluation, two sets of pictures were taken for the normal shot camera. In the first set, the camera's circular polarizing filter was configured such that its polarization was parallel to the polarization of the fluorescent lights, giving a picture that highlighted the shine as well as the fine wrinkles, pores and skin texture. In the second set, the circular polarizing filter was configured such that the polarization was perpendicular (or cross) to the polarization of the fluorescent lights yielding a result that eliminated all glare and shows the underlying skin tone, discoloration, and deep wrinkles. The 45° shot camera was configured for each evaluation such that the camera's circular polarizing filter was configured so that its polarization was parallel to the polarization of the fluorescent lights, giving a picture that highlighted the shine as well as fine wrinkles, pores and skin texture.

Brow-Lift Measure of Photo:

To measure the brow height of a photograph, a photograph was obtained using the method of photo capture previously described above. A "canthus line" was then drawn on the photograph from the medial to the lateral canthus on each eye. This canthus line was used as a base ft m which the brow height was measured. The eyebrow was isolated from the image by applying valley detection, edge detection and thresholding graphical operations on the image. Within one experiment, the parameters for valley and edge detection and thresholding were constant so that the same portions of the eyebrow from each image series was the same. To accurately isolate the eyebrow, these parameters were changed to account for differences in photographic exposure between experiments and skin and brow colors between panelists. From these methods, a binary mask was created which was then further manipulated in order to ensure only the eyebrows were isolated in the picture. For overall height change measurements, the center of mass of each eyebrow was then determined from its binary mask. The parameters for the binary operations and center of mass determination were always kept constant. The height of each brow was the normal from its center of mass to its corresponding canthus line. This method measured overall height change but did not capture the magnitude of change for severe arching or angling where portions were raised and portions were lowered. For such cases, instead of measuring the brow's center of mass, the heights of the brow normal to the canthus line at its left and right edges and at its center were determined from the binary mask.

Redness Reduction Photo Measure:

Photographs are obtained of the panelist using the photographic setup previously described. Comparisons of redness are only done on photographs taken within the same experiment because the exposure, and light and face positioning are only constant within a single experiment. After the series of photographs in the experiment are taken, the cross-polarized pictures are overlaid such that the area to be evaluated for redness reduction remains as fixed as is possible between each image. Using graphical manipulation software, the L*a*b* channels in the CIELAB colorspace are created for each image in the series. The L* value represents the degree of illumination, while a* and b* define the chromaticity. Specifically, a* represents the degree of redness (+ values) or greenness (− values). The intensity of the red color square on the color card in the baseline photograph's a* channel is then used to normalize the subsequent images by adjusting the intensity of the subsequent image a* channels until the a* values within the red color square on the color cards in those images equals the baseline value. The area of evaluation is then cropped out of the photographs. Redness reduction is then determined by subtracting the a* values for the area in the 'before' photographs from the a* values in the 'after' photographs. A negative value from this subtraction indicates a reduction in redness while a positive value indicates an increase.

Example 4: Stress Testing Methods

The mechanical durability of the materials was evaluated by creating an artificial brow lift by applying one of the following methods of pre-tensioning the skin during product application. These methods of pre-tensioning were used to stress the skin surface and pull the brow into a lifted position:

"brow orthogonal push," in which a stress was applied that originated at the eyebrow and is vectored anteriorly away from the eyebrow at an angle that was between 80° and 100° relative to the line of the eyebrow, "corner hairline diagonal pull," in which a stress was applied that originated at the most anterior and lateral point on the panelist's hairline and was vectored anteriorly away from and at an angle between 10° and 80° relative to the line of the eyebrow, "corner hairline orthogonal pull," in which a stress was applied that originated at the most anterior and lateral point on the panelist's hairline and was vectored anteriorly away from and at an angle between 80° and 100° relative to the line of the eyebrow, "lateral hairline orthogonal push" in which a stress was applied that originated at the most lateral point of the hairline that was at or above the level of the eyes and was vectored anteriorly away from at an angle between 80° and 100° relative to the line of the eyebrow.

While the brow was held lifted by one of these stresses, the product was applied to the area of skin over which the tension was being applied. Once the film cured, the stress was removed and the mechanical durability of the film's ability to hold the tensions in the skin was evaluated. This evaluation was achieved by measuring the degree of brow lift using the methods described before and after product application. Durability of the effect was measured by allowing time, normal and exaggerated facial expressions and environmental stresses such as water, sweat, heat, sebum production and surface contact to interact with the film. The amount of lift was tracked at regular intervals to determine how quickly the film's ability to hold the mechanical benefit lasted. A film was determined to be mechanically durable if it could withstand the stresses previously mentioned and maintain the brow lift at the level originally achieved immediately after application.

Example 5. Formulations

Examples of formulations illustrating the two-step application method are provided below. The reactive reinforcing component first step (e.g., the treatment) includes formulations 60-140-1, 60-140-1B, 60-140-HP2, SK 87/2, 60-140-LX2, SK 87/1, 48-196, 48-199, 60-211, 60-200-1N, 60-208, 66-166-F, 66-167-E, 66-166-C, 66-169-3, 66-170, 79-23, 79-24b, 79-45, 79-46, 79-41, 88-30-1, 83-16, 79-55a, 79-55b, 79-55c, 79-55d, 79-55e, 79-55f, 79-55g, 83-54, 79-55h, 81-18, 81-19, 81-20, 81-21, 79-74, 80-23, 79-88, 79-88-3A, 79-74-RD, 79-90-B, 88-70, 88-72, 88-75-2, 88-75-3, 88-80, 88-85-1, 88-85-2, 88-83-V2, 88-83-V3 and 83-54 shown below.

Components of the formulations are commercially available. The following table provides the generic name for any trade name used throughout this application.

| Tradename | International Nomenclature Cosmetic Ingredient (INCI) name |
|---|---|
| Aerogel VM2270 | Silica Silylate |
| Aerosil 8200 ™ or Aerosil R8200 ™ | Fumed silica modified with hexamethyldisilazane |
| Andisil C1000 ™ | Silicon dioxide + Dimethylpolysiloxane |
| Andisil C1300 ™ | Silicon dioxide + Dimethylpolysiloxane |
| Andisil CE-4 ™ | Vinyl Dimethicone |
| Andisil MV 2,000 ™ or MV2000 | Vinyl Dimethicone |
| Andisil VS 1,000 ™ | Vinyl Dimethicone |
| Andisil VS 10,000 ™ | Vinyl Dimethicone |
| Andisil VS 165,000 ™ or Andisil VS165K | Vinyl Dimethicone |
| Andisil VS 20,000 ™ | Vinyl Dimethicone |
| Andisil VS 250 ™ | Vinyl Dimethicone |
| Andisil VS 500 ™ or VS500 | Vinyl Dimethicone |
| Andisil VS 65,000 ™ or VS65,000 | Vinyl Dimethicone |
| Andisil XL-11 ™ | Hydrogen Dimethicone, SiH Functional |
| Andisil XL-1B ™ or XL-1B | Hydrogen Dimethicone, SiH Functional |
| Aquadispersable Rutile Titanium Dioxide ™ | Titanium dioxide |
| Barium Sulfate HL | Barium Sulfate |
| Beaver UV/Fluorescent Pigment | AROMATIC HETEROCYCLE |
| Cabosperse 1030K | CAB-O-SPERSE ® 1030K is an aqueous dispersion of CAB-O-SIL ® L-90, a very low surface area, fumed silica. It is electrostatically stabilized with Potassium Hydroxide and has an alkaline pH. |
| Carbopol Ultrez 21 | Acrylates/C10-30 Alkyl Acrylate Crosspolymer |
| Cetiol OE | Dicapryl Ether |
| Chronosphere Optical Brite or Chronosphere Opticals/Opticals Brite | Silica and polyurethane-40/silica and polyurethane-40 and green 5 |
| cremaphor EL | PEG-35 Castor Oil |
| Crodamol STS | PPG 3 Benzyl Ether Myristate |
| DC 200 Fluid (1 cSt) | Dimethicone |
| DC 2-1184 fluid (DOW CORNING ® 2-1184 FLUID) | Trisiloxane (and) Dimethicone |
| DC 556 | Phenyl Trimethicone |
| DMF5 CS | dimethicone |
| DMS-V41 | Poly(Dimethylsiloxane), Vinyl Terminated |
| Dow 245 Fluid (Dow CORNING 245 Fluid) | Cyclopentasiloxane |
| Dow 246 Fluid (Dow CORNING 246 Fluid) | Cyclohexasiloxane |
| Dow 9011 Elastomer Blend (Dow Corning 9011 Elastomer Blend) | Cyclopentasiloxane (and) PEG-12 Dimethicone Crosspolymer |
| Dow Corning 9011 Silicone Elastomer Blend ™ or Dow Elastomer Blend 9011 | Cyclopentasiloxane (and) PEG-12 Dimethicone Crosspolymer |
| Dow 9045 Elastomer Blend or Dow Corning 9045 Silicone Elastomer Blend ™ | Cyclopentasiloxane (and) Dimethicone Crosspolymer |
| Dow Corning 200 Fluid 0.65 cSt ™ | Hexamethyldisiloxane |
| Dow Corning 245 Fluid ™ | Decamethylcyclopentasiloxane |
| Dow Corning 5329 | PEG-12 Dimethicone |
| Dow Elastomer Blend 9041 or DOW CORNING ® 9041 SILICONE ELASTOMER BLEND | Dimethicone (and) Dimethicone Crosspolymer |
| dowanol DPM | Dipropylene Glycol Methyl Ether |
| Dri-Flow Elite BN or DRY-FLO Elite BN | Aluminum Starch Octenylsuccinate (and) Boron Nitride |
| Flo-Beads SE-3207B ™ | Ethylene-methyl methacrylate copolymer |
| Dow Corning FZ-3196 | Caprylyl Methicone |
| Ganzpearl GMP-0830 ™ | Acrylates Crosspolymer |

-continued

| Tradename | International Nomenclature Cosmetic Ingredient (INCI) name |
|---|---|
| Granhydrogel O ™ | Water (and) Glyceryl Polyacrylate (and) 1,3-Butylene Glycol (and) PVM/MA (and) Propylparaben (and) Methylparaben |
| Granpowder Nylon ™ | Nylon-12 |
| Gransil EP-LS ™ | Polysilicone-11 (and) Laureth-12 |
| Gransurf 90 | Cetyl PEG/PPG-10/1 Dimethicone |
| Iris | C12-17 Alkanes |
| Iron Oxide Tint or Iron Oxide Tint Mixture | Iron Oxides |
| Isododecane | mixture of highly branched C12 isoparaffins, mainly the 2,2,4,6,6-pentamethylheptane isomer (typically c.a. 85%). |
| Jeechem BUGL ™ or Jeen BUGL | Bulylene Glycol |
| Jeecide cap 5 | Phenoxyethanol, Caprylyl Glycol, Potassium Sorbate, Aqua, Hexylene Glycol |
| Jeensilc CPS-312 ™ | Cyclomethicone |
| Kaolin USP BC2747 | Kaolin |
| KF6013 | PEG-9 Dimethicone |
| KTZ Xian Vistas ™ | Titanium Dioxide (And) Mica (And) Iron Oxide (C.I. 77491); chemical name: Mica (and) Titanium Dioxide (and) Ferrous Oxide |
| Labrafac CC ™ | Caprylic/Capric Triglyceride |
| LILAC ™ (Sonneborn) | C14-22 Alkane |
| MPDiol | Methyl Propanediol |
| Neolone PE ™ | Phenoxyethanol, Methylisothiazolinone |
| Nylon | Nylon 12 |
| Nylon 10-I2 ™ | Nylon 12 (And) Isopropyl Titanium Triisostearate |
| PC 075.3 | Hydrogen Dimethicone |
| Pink tint mix | Iron Oxides |
| Plantacare 818 UP ™ | Coco-Glucoside; Chemical Description is "C8-16 fatty alcohol glucoside" |
| Platinum divinyl complex (for example PT-50175F) | UPAC name "1,3-Diethenyl-1,1,3,3-tetramethyldisiloxane-platinum (1:1)"; Trade name: "Platinum-divinyltetramethyldisiloxane complex"; Synonyms: Platinum(0)-1,3-divinyl-1,1,3,3-tetramethyldisiloxane complex solution; pt(0)-1,3-divinyl-tetrame-disiloxane compl 0.100; 1,3-Divinyl-1,1,3,3-tetramethyl-disiloxane-platinum (0) |
| PMX-1184 or XIAMETER ® PMX-1184 Silicone Fluid | Dimethicone and trisiloxane |
| Polyglycol P425 | PPG-9 |
| prestige pearlescent beige | mixture of titanium and iron oxides of a beige color |
| PS123-KG | Hydrogen Dimethicone |
| RM 2051 or RM 2051 Thickening Agent | Sodium Polyacrylate (and) Dimethicone (and) Cyclopentasiloxane (and) Trideceth-6 (and) PEG/PPG 18/18 |
| Schercemol ™ 318 Ester | Isopropyl Isostearate |
| Sepiplus 400 ™ | Polyacrylate 13 (and) Polyisobutene (and) Polysorbate 20 |
| Shin Etsu KF 6038 | Lauryl PEG-9 Polymethylsiloxyethyl Dimethicone |
| Shin Etsu KSG 820 | Lauryl Dimethicone/Polyglycerin-3 Crosspolymer |
| Silsoft 034 | caprylyl methicone |
| silsoft ETS | ethyl trisiloxane |
| Simulgel EG ™ | Sodium acrylate/acryloyldimethyl taurate copolymer & Isohexadecane & Polysorbate 80 |
| SIMULGEL NS | Hydroxyethylacrylate/sodium acryloyldimethyl taurate copolymer & squalane & polysorbate 60 |
| Soft Bead B or Soft Beads B | Ethylene/Methacrylate Copolymer |
| Solagum AX | *Acacia senegal* gum and xanthan gum |
| SR 1000 Resin | Trimethylsiloxysilicate |
| Tint | Iron Oxides |
| TMF 1.5 | Methyl Trimethicone |
| Tween 20 | Polysorbate 20 |
| UCT-PS448.5 | Polydimethylsiloxane, Vinyldimethyl Terminated |
| USG 102 | Dimethicone/Vinyl Dimethicone Crosspolymer |
| Veegum Pro | Tromethamine Magnesium Aluminum Silicate |

-continued

| Tradename | International Nomenclature Cosmetic Ingredient (INCI) name |
|---|---|
| Veegum Ultra Granules | Magnesium Aluminum Silicate |
| Velvesil 125 ™ | Cyclopentasiloxane (and) C30-45 Alkyl Cetearyl Dimethicone |
| Velvet Veil 310 ™ | Mica (and) Silica |
| Vitamin-A complex | retinol |
| Vitamin-C complex | ascorbic acid |
| Vitamin-E complex | Tocopherol |
| Xirona caribbean blue | Mica, Titanium Dioxide, Silica, Tin Oxide |

Formulation 60-140-1

| Component No. | Component | Percent of Formulation (%) |
|---|---|---|
| 1 | DMS-V41 | 23.80 |
| 2 | Aerosil 8200 | 9.45 |
| 3 | PS123-KG | 12.00 |
| 4 | UCT-PS448.5 | 5.55 |
| 5 | Velvesil 125 | 3.60 |
| 6 | Gransil EP-LS | 3.60 |
| 7 | Soft Beads B | 1.20 |
| 8 | Sepiplus 400 | 1.20 |
| 9 | Water | 27.00 |
| 10 | Granhydrogel O | 6.70 |
| 11 | Granpowder Nylon | 5.90 |

Procedure:

Components 1-4 were hand mixed in a graduated 4-oz until mixture was free of white particulates. Subsequently, components 5-8 were added and the mixture was confirmed as homogenous (Mixture A). In a separate vessel, components 9 and 10 were hand mixed until homogenous (Mixture B). Mixture B was added to Mixture A under strong agitation, provided by a 4-blade, 40 mm propeller at 550 rpm, then component 11 was added and the mixing speed was to 1000 rpm and mix for 5 minutes. The mixture was confirmed as homogenous.

Formulation 60-140-1B

| Component No. | Component | Percent of Formulation (%) |
|---|---|---|
| 1 | DMS-V41 | 22.60 |
| 2 | Aerosil 8200 | 8.94 |
| 3 | PS123-KG | 11.30 |
| 4 | UCT-PS448.5 | 5.30 |
| 5 | Velvesil 125 | 3.42 |
| 6 | Gransil EP-LS | 3.42 |
| 7 | Soft Beads B | 1.20 |
| 8 | Sepiplus 400 | 1.20 |
| 9 | Water | 25.66 |
| 10 | Granhydrogel O | 6.36 |
| 11 | Granpowder Nylon | 5.60 |
| 12 | Cetiol OE | 5.00 |

Procedure:

Components 1-4 were hand mixed in a graduated 4-oz and the mixture was confirmed as free of white particulates. Subsequently, components 5-8 were added and the mixture was confirmed homogenous (Mixture A). In a separate vessel, components 9 and 10 were hand mixed until homogenous (Mixture B). Mixture B to was added Mixture A under strong agitation, provided by a 4-blade, 40 mm propeller at 550 rpm, then components 11 and 12 were added and the mixing speed was increased to 1000 rpm and mix for 5 minutes. The mixture was confirmed as homogenous.

Formulation 60-140-HP2

| Component No. | Component | Percent of Formulation (%) |
|---|---|---|
| 1 | UCT-PS448.5 | 32.97 |
| 2 | Aerosil 8200 | 12.82 |
| 3 | PS123-KG | 14.65 |
| 4 | Velvesil 125 | 4.40 |
| 5 | Gransil EP-LS | 4.40 |
| 6 | Soft Beads B | 1.47 |
| 7 | Sepiplus 400 | 1.47 |
| 8 | Granhydrogel O | 20.63 |
| 9 | Granpowder Nylon | 7.20 |

Procedure:

Components 1-3 were hand mixed in a graduated 4-oz and the mixture was confirmed as free of white particulates. Subsequently, components 4-7 were added the mixture was confirmed homogenous (Mixture A). In a separate vessel, component 8 was mixed until homogenous (Mixture B). Mixture B to was added Mixture A under strong agitation, provided by a 4-blade, 40 mm propeller at 550 rpm, then component 9 was added and the mixing speed was increased to 1000 rpm and mix for 5 minutes. The mixture was confirmed as homogeneous.

Formulation SK 87/2

| Component No. | Component | Percent of Formulation (%) |
|---|---|---|
| 1 | DMS V41 | 35.00 |
| 2 | Aerosil 8200 | 11.60 |
| 3 | PS123-KG | 5.20 |
| 4 | Velvesil 125 | 11.20 |
| 5 | Gransil EP-LS | 8.70 |
| 6 | Water | 6.70 |
| 7 | Polyvinyl alcohol | 2.00 |
| 8 | Granhydrogel O | 8.70 |
| 9 | Granpowder Nylon | 6.10 |
| 10 | Silsoft 034 | 4.80 |

Procedure:

Components 1-3 were hand mixed in a graduated 4-oz and the mixture was confirmed as free of white particulates. Subsequently, components 4 and 5 were added and the mixture was confirmed as homogenous (Mixture A). In a separate vessel, components 6 and 7 were hand mixed until homogenous (Mixture B). Mixture B was added to Mixture A under strong agitation, provided by a 4-blade, 40 mm propeller at 550 rpm, then components 8-10 were added and the mixing speed was increased to 1000 rpm and mix for 5 minutes. The mixture was confirmed as homogeneous.

Formulation 60-140-LX2

| Component No. | Component | Percent of Formulation (%) |
|---|---|---|
| 1 | DMS V41 | 27.51 |
| 2 | Aerosil 8200 | 10.87 |
| 3 | PS123-KG | 3.47 |
| 4 | UCT-PS448.5 | 13.41 |
| 5 | Velvesil 125 | 4.16 |
| 6 | Gransil EP-LS | 4.16 |
| 7 | Soft Bead B | 1.39 |
| 8 | Sepiplus 400 | 1.39 |
| 9 | Water | 21.45 |
| 10 | Granhydrogel O | 5.38 |
| 11 | Granpowder Nylon | 6.82 |

Procedure:

Components were hand mixed 1-4 in a graduated 4-oz and the mixture was confirmed as free of white particulates. Subsequently, components 5-8 were added and mixture was confirmed as homogenous (Mixture A). In a separate vessel, components 9 and 10 were hand mixed until homogenous (Mixture B). Mixture B was added to Mixture A under strong agitation, provided by a 4-blade, 40 mm propeller at 550 rpm, then component 11 was added and the mixing speed was increased to 1000 rpm and mixed for 5 minutes. The mixture was confirmed as homogeneous.

Formulation SK 87/1

| Component No. | Component | Percent of Formulation (%) |
| --- | --- | --- |
| 1 | DMS V41 | 36.90 |
| 2 | Aerosil 8200 | 12.30 |
| 3 | PS123-KG | 5.50 |
| 4 | Velvesil 125 | 11.60 |
| 5 | Gransil EP-LS | 9.10 |
| 6 | Water | 7.10 |
| 7 | Polyvinyl alcohol | 2.00 |
| 8 | Granhydrogel O | 9.10 |
| 9 | Granpowder Nylon | 6.40 |

Procedure:

Components 1-3 were hand mixed in a graduated 4-oz and the mixture was confirmed as free of white particulates. Subsequently, components 4 and 5 were added and the mixture was confirmed as homogenous (Mixture A). In a separate vessel, components 6 and 7 were hand mixed until homogenous (Mixture B). Mixture B was added to Mixture A under strong agitation, provided by a 4-blade, 40 mm propeller at 550 rpm, then components 8 and 9 were added and the mixing speed was increased to 1000 rpm and mixed for 5 minutes. The mixture was confirmed as homogeneous.

Formulation 48-196

| Component No. | Component | Percent of Formulation (%) |
| --- | --- | --- |
| 1 | Andisil VS10,000 | 24.46 |
| 2 | Andisil VS165K | 3.66 |
| 3 | Aerosil 8200 | 9.72 |
| 4 | Andisil XL-11 | 12.33 |
| 5 | Velvesil 125 | 3.70 |
| 6 | Gransil EP-LS | 3.70 |
| 7 | Soft Beads B | 1.23 |
| 8 | Sepiplus 400 | 1.23 |
| 9 | Water | 27.75 |
| 10 | Granhydrogel O | 6.87 |
| 11 | Neolone PE | 0.21 |
| 12 | Granpowder Nylon | 4.11 |
| 13 | Tint | 1.03 |

Procedure:

Components 1-3 were mixed in a graduated 4-oz with a 4-blade propeller at 1000 RPM until homogenous (Mixture A) and the mixture was confirmed as homogenous. In a separate container components 4-8 were mixed with a 4-blade propeller at 750 RPM until homogenous (Mixture B). In another container, components 9-11 were mixed with a 4-blade propeller at 750 RPM until homogenous (Mixture C). Mixture B was added to Mixture C under strong agitation, provided by a 4-blade, 40 mm propeller at 750 rpm, then Mixture A was added to combined Mixtures B and C drop by drop. Finally, components 12 and 13 were added and the mixing speed increased to 1000 RPM and mix for 10 minutes. The mixture was confirmed as homogeneous.

Formulation 48-199

| Component No. | Component | Percent of Formulation (%) |
| --- | --- | --- |
| 1 | Andisil VS10,000 | 22.11 |
| 2 | Andisil VS165K | 3.31 |
| 3 | Aerosil 8200 | 8.79 |
| 4 | Andisil XL-11 | 11.15 |
| 5 | Velvesil 125 | 3.35 |
| 6 | Gransil EP-LS | 3.35 |
| 7 | Soft Beads B | 1.12 |
| 8 | Sepiplus 400 | 1.12 |
| 9 | Water | 25.09 |
| 10 | Granhydrogel O | 6.21 |
| 11 | Neolone PE | 0.19 |
| 12 | Granpowder Nylon | 4.94 |
| 13 | Silsoft 034 | 9.29 |

Procedure:

Components 1-3 were mixed in a graduated 4-oz with a 4-blade propeller at 1000 RPM until homogenous (Mixture A). In a separate container, components 4-8 were mixed with a 4-blade propeller at 750 RPM until homogenous (Mixture B). In another container, components 9-11 were mixed with a 4-blade propeller at 750 RPM until homogenous (Mixture C). Mixture B to Mixture C was added under strong agitation, provided by a 4-blade, 40 mm propeller at 750 rpm, then Mixture A was added to combined Mixtures B and C drop by drop. Finally, components 12 and 13 were added and the mixing speed was added to 1000 RPM and mixed for 10 minutes. The mixture was confirmed as homogeneous.

Formulation 60-211

| Component No. | Component | Percent of Formulation (%) |
| --- | --- | --- |
| 1 | Andisil C1000 | 33.66 |
| 2 | Andisil C1300 | 6.73 |
| 3 | Andisil XL-11 | 9.62 |
| 4 | Velvesil 125 | 3.46 |
| 5 | Gransil EP-LS | 3.46 |
| 6 | Soft Beads B | 1.15 |
| 7 | Sepiplus 400 | 1.15 |
| 8 | Water | 25.97 |
| 9 | Granhydrogel O | 6.42 |
| 10 | Jeechem BUGL | 3.85 |
| 11 | Neolone PE | 0.19 |
| 12 | Granpowder Nylon | 3.85 |
| 13 | Tint | 0.49 |

Procedure:

Components 1-7 were mixed in a graduated 4-oz with a 4-blade propeller at 2000 RPM until homogenous (Mixture A). In a separate container, components 8-11 were mixed with a 4-blade propeller at 750 RPM until homogenous (Mixture B). Mixture B was slowly added to Mixture A under strong agitation provided by a 4-blade propeller at 2000 RPM. Components 12 and 13 were added and the mixing speed was increased to 2000 RPM for 5 minutes. The mixture was confirmed as homogeneous.

Formulation 60-200-1N

| Component No. | Component | Percent of Formulation (%) |
| --- | --- | --- |
| 1 | Andisil C1000 | 33.88 |
| 2 | Andisil C1300 | 7.65 |
| 3 | Andisil XL-11 | 18.03 |
| 4 | SR 1000 Resin | 10.93 |

| Component No. | Component | Percent of Formulation (%) |
|---|---|---|
| 5 | Iris | 2.19 |
| 6 | Dri-Flow Elite BN | 10.93 |
| 7 | Barium Sulfate HL | 4.37 |
| 8 | Gransil EP-LS | 8.74 |
| 9 | Sepiplus 400 | 2.19 |
| 10 | Neolone PE | 0.55 |
| 11 | Tint | 0.54 |

Procedure:

Components 1-5 were mixed in a graduated 4-oz with a 4-blade propeller at 2000 RPM until homogenous (Mixture A). Components 6-9 were then added and mixed with a 4-blade propeller at 2000 RPM until homogenous. Components 10 and 11 were added and the mixing speed was mixed at 2000 RPM until homogeneous.

Formulation 60-208

| Component No. | Component | Percent of Formulation (%) |
|---|---|---|
| 1 | Andisil C1000 | 30.05 |
| 2 | Andisil C1300 | 6.56 |
| 3 | Andisil XL-11 | 22.95 |
| 4 | SR 1000 Resin | 10.93 |
| 5 | Iris | 2.19 |
| 6 | Dri-Flow Elite BN | 10.93 |
| 7 | Barium Sulfate HL | 4.37 |
| 8 | Gransil EP-LS | 8.74 |
| 9 | Sepiplus 400 | 2.19 |
| 10 | Neolone PE | 0.55 |
| 11 | Tint | 0.54 |

Procedure:

Components 1-5 were mixed in a graduated 4-oz with a 4-blade propeller at 2000 RPM until homogenous (Mixture A). Components 6-9 were then added and mixed with a 4-blade propeller at 2000 RPM until homogenous. Components 10 and 11 were added and the mixing speed was mixed at 2000 RPM until homogeneous.

Formulation 66-166-F

| Component No. | Component | Percent of Formulation (%) |
|---|---|---|
| 1 | Aerosil 8200 ™ | 8.43% |
| 2 | Andisil VS 10,000 ™ | 21.22% |
| 3 | Andisil VS 165,000 ™ | 3.17% |
| 4 | Andisil XL11 ™ | 10.34% |
| 5 | Velvesil 125 ™ | 3.10% |
| 6 | Gransil EP-LS ™ | 3.10% |
| 7 | Flo-Beads SE-3207B ™ | 1.03% |
| 8 | Sepiplus 400 ™ | 1.03% |
| 9 | Water | 23.28% |
| 10 | Granhydrogel O ™ | 5.75% |
| 11 | Neolone PE ™ | 0.17% |
| 12 | Granpowder Nylon ™ | 4.23% |
| 13 | Ganzpearl GMP-0830 ™ | 0.31% |
| 14 | Velvet Veil 310 ™ | 0.21% |
| 15 | Aquadispersable Rutile Titanium Dioxide ™ | 0.21% |
| 16 | Yellow Iron Oxide | 0.09% |
| 17 | Red Iron Oxide | 0.04% |
| 18 | Black Iron Oxide | 0.01% |
| 19 | Dow Corning 200 Fluid 0.65 cSt ™ | 14.29% |

Procedure:

Components 1-3 were mixed together as siloxane phase A. Into siloxane phase B, components 4-8 were mixed. Components 9-11 were combined as the water phase. The water phase was slowly added to siloxane phase B and mixed until homogenous. Into this new phase, phase A was added very slowly drop by drop. Once all of siloxane phase A was added, components 12-19 were added to the formula and mix until homogenous.

Formulation 66-167-E

| Component No. | Component | Percent of Formulation(%) |
|---|---|---|
| 1 | Aerosil 8200 ™ | 8.36% |
| 2 | Andisil VS 10,000 ™ | 21.05% |
| 3 | Andisil VS 165,000 ™ | 3.15% |
| 4 | Andisil XL11 ™ | 10.25% |
| 5 | Velvesil 125 ™ | 3.08% |
| 6 | Gransil EP-LS ™ | 3.08% |
| 7 | Flo-Beads SE-3207B ™ | 1.02% |
| 8 | Sepiplus 400 ™ | 1.02% |
| 9 | Water | 23.09% |
| 10 | Granhydrogel O ™ | 5.70% |
| 11 | Neolone PE ™ | 0.17% |
| 12 | Granpowder Nylon ™ | 4.20% |
| 13 | Ganzpearl GMP-0830 ™ | 0.31% |
| 14 | Velvet Veil 310 ™ | 0.20% |
| 15 | Aquadispersable Rutile Titanium Dioxide ™ | 0.20% |
| 16 | Yellow Iron Oxide | 0.09% |
| 17 | Red Iron Oxide | 0.04% |
| 18 | Black Iron Oxide | 0.01% |
| 19 | LILAC ™ (Sonneborn) | 2% |
| 20 | Cetyl Dimethicone | 5% |
| 21 | Granhydrogel O ™ | 8% |

Procedure:

Components 1-3 were mixed together as siloxane phase A. Into siloxane phase B components 4-8 were added. Components 9-11 were combined as the water phase. The water phase was slowly added to siloxane phase B and mixed until homogenous. Into this new phase, phase A was added very slowly drop by drop. Once all of siloxane phase A was added, components 12-21 were added to the formula and mixed until homogenous.

Formulation 66-166-C

| Component No. | Component | Percent of Formulation (%) |
|---|---|---|
| 1 | Aerosil 8200 ™ | 8.43% |
| 2 | Andisil VS 10,000 ™ | 21.22% |
| 3 | Andisil VS 165,000 ™ | 3.17% |
| 4 | Andisil XL11 ™ | 10.34% |
| 5 | Velvesil 125 ™ | 3.10% |
| 6 | Gransil EP-LS ™ | 3.10% |
| 7 | Flo-Beads SE-3207B ™ | 1.03% |
| 8 | Sepiplus 400 ™ | 1.03% |
| 9 | Water | 23.28% |
| 10 | Granhydrogel O ™ | 5.75% |
| 11 | Neolone PE ™ | 0.17% |
| 12 | Granpowder Nylon ™ | 4.23% |
| 13 | Ganzpearl GMP-0830 ™ | 0.31% |
| 14 | Velvet Veil 310 ™ | 0.21% |
| 15 | Aquadispersable Rutile Titanium Dioxide ™ | 0.21% |
| 16 | Yellow Iron Oxide | 0.09% |
| 17 | Red Iron Oxide | 0.04% |
| 18 | Black iron Oxide | 0.01% |
| 19 | Granhydrogel O ™ | 14.29% |

Procedure:

Components 1-3 were mixed together as siloxane phase A. Into siloxane phase B components 4-8 were added. Components 9-11 were combined as the water phase. The water phase was slowly added to siloxane phase B and mixed until homogenous. Into this new phase, phase A was very slowly added drop by drop. Once all of siloxane phase A was added, components 12-19 was added to the formula and mixed until homogenous.

Formulation 66-169-3

| Component No. | Component | Percent of Formulation (%) |
|---|---|---|
| 1 | Ganzpearl GMP-0830 ™ | 0.16% |
| 2 | Velvet Veil 310 ™ | 0.10% |
| 3 | Aquadispersable Rutile Titanium Dioxide ™ | 0.10% |
| 4 | Yellow Iron Oxide | 0.04% |
| 5 | Red Iron Oxide | 0.02% |
| 6 | Black Iron Oxide | 0.01% |
| 7 | Gransil EP-LS ™ | 0.76% |
| 8 | Andisil XL-11 ™ | 8.61% |
| 9 | Gransil EP-LS ™ | 2.34% |
| 10 | Andisil C1000 ™ | 33.51% |
| 11 | Andisil C1300 ™ | 6.67% |
| 12 | Andisil XL-11 ™ | 1.59% |
| 13 | Velvesil 125 ™ | 3.48% |
| 14 | Flo-Beads SE-3207B ™ | 1.15% |
| 15 | Sepiplus 400 ™ | 1.27% |
| 16 | Water | 25.18% |
| 17 | Granhydrogel O ™ | 6.22% |
| 18 | Jeechem BUGL ™ | 3.75% |
| 19 | Neolone PE ™ | 0.21% |
| 20 | Granpowder Nylon ™ | 3.83% |
| 21 | KTZ Xian Vistas ™ | 1.00% |

Procedure:

Components 1-8 were mixed together and homogenized at 26,000 RPM for 10 minutes. After 10 minutes, component 9 was added and homogenized again for 10 minutes at 26,000 RPM. To this homogenized mixture, components 10-15 were added and mixed with an overhead stirrer at 2,000 RPM until homogenous in appearance (this is the siloxane phase). In a separate container, components 16-19 were mixed until homogenous to form the water phase. The water phase was added to the siloxane phase very slowly, with continuous stirring at 2.000 RPM. Once the water phase was completely mixed in, components 20 and 21 were added to the formula and mixed at 2,000 RPM until homogenous.

Formulation 66-170

| Component No. | Component | Percent of Formulation (%) |
|---|---|---|
| 1 | Andisil C1300 ™ | 8.92% |
| 2 | Andisil C1000 ™ | 44.21% |
| 3 | Andisil XL-11 ™ | 12.67% |
| 4 | Sepiplus 400 ™ | 1.30% |
| 5 | Ganzpearl GMP-0830 ™ | 0.18% |
| 6 | Velvet Veil 310 ™ | 0.12% |
| 7 | Aquadispersable Rutile Titanium Dioxide ™ | 0.12% |
| 8 | Yellow Iron Oxide | 0.05% |
| 9 | Red Iron Oxide | 0.02% |
| 10 | Black Iron Oxide | 0.01% |
| 11 | Dow Corning 9011 Silicone Elastomer Blend ™ | 3.25% |
| 12 | Dow Corning 9045 Silicone Elastomer Blend ™ | 3.25% |
| 13 | Dow Corning 245 Fluid ™ | 2.62% |
| 14 | Jeensilc CPS-312 ™ | 0.65% |
| 15 | Water | 9.49% |
| 16 | Plantacare 818 UP ™ | 0.16% |
| 17 | Propylene Glycol | 6.60% |
| 18 | Glycerin | 1.29% |
| 19 | Jeechem BUGL ™ | 3.22% |
| 20 | Sodium Chloride | 0.32% |
| 21 | Nylon 10-I2 ™ | 1.53% |

Procedure:

Components 1-10 were mixed together to create the siloxane phase A. Next, components 11-14 were mixed to create siloxane phase B. A water phase was created by mixing components 15-20. The water phase was slowly added into siloxane phase B while mixing at 2,000 RPM to create phase C. Finally, phase C was mixed into siloxane phase A until homogenous.

Formulation 79-23

| Component No. | Component | Percent of Formulation (%) |
|---|---|---|
| 1 | Andisil VS 500 ™ | 0.72 |
| 2 | Andisil MV 2000 ™ | 1.02 |
| 3 | Andisil VS 65,000 ™ | 17.20 |
| 4 | Andisil XL-1B ™ | 22.52 |
| 5 | Aerosil R8200 ™ | 11.77 |
| 6 | Ganzpearl GMP-0830 ™ | 0.19 |
| 7 | Velvet Veil 310 ™ | 0.13 |
| 8 | Aquadispersabie Rutile Titanium Dioxide ™ | 0.13 |
| 9 | Yellow Iron Oxide | 0.05 |
| 10 | Red Iron Oxide | 0.03 |
| 11 | Black Iron Oxide | 0.01 |
| 12 | Gransil EP-LS ™ | 3.59 |
| 13 | Velvesil 125 ™ | 3.58 |
| 14 | Flo-Beads SE-3207B ™ | 1.02 |
| 15 | Sepiplus 400 ™ | 1.10 |
| 16 | Water | 23.72 |
| 17 | Granhydrogel O ™ | 6.99 |
| 18 | Jeechem BUGL ™ | 3.50 |
| 19 | Sodium Chloride | 0.35 |
| 20 | Neolone PE ™ | 0.35 |
| 21 | Granpowder Nylon ™ | 2.05 |

Procedure:

Components 1-5 were combined and mixed (Mixture A) in a dual asymmetric centrifugal mixer at 2500 RPM while confirming that the mixture was free of white particulates. Components 6-15 were mixed into Mixture A and mixed in a dual asymmetric centrifugal mixer. Mixture A was confirmed as homogenous. In a separate vessel, components 16 and 20 were mixed with a 4-blade, 40 mm propeller at 550 rpm until homogenous (Mixture B). Mixture B was added to Mixture A dropwise while mixing with a 4-blade 40 mm propeller at 2000 rpm and the mixture was confirmed as homogenous. Component 21 was added to the product of Mixture A and Mixture B and mixed with 4-blade 40 mm propeller at 1000 rpm until homogenous.

Formulation 79-24b

| Component No. | Component | Percent of Formulation (%) |
|---|---|---|
| 1 | Andisil VS 500 ™ | 0.72 |
| 2 | Andisil MV 2000 ™ | 1.07 |
| 3 | Andisil VS 65,000 ™ | 17.91 |
| 4 | Andisil XL-1B ™ | 23.15 |
| 5 | Aerosil R8200 ™ | 12.12 |
| 6 | Ganzpearl GMP-0830 ™ | 0.19 |
| 7 | Velvet Veil 310 ™ | 0.13 |

-continued

| Component No. | Component | Percent of Formulation (%) |
|---|---|---|
| 8 | Iron Oxide Tint | 0.22 |
| 9 | Gransil EP-LS ™ | 3.70 |
| 10 | Velvesil 125 ™ | 3.70 |
| 11 | Flo-Beads SE-3207B ™ | 1.06 |
| 12 | Sepiplus 400 ™ | 1.11 |
| 13 | Water | 22.31 |
| 14 | Granhydrogel O ™ | 6.56 |
| 15 | Jeechem BUGL ™ | 3.28 |
| 16 | Sodium Chloride | 0.33 |
| 17 | Neolone PE ™ | 0.33 |
| 18 | Granpowder Nylon ™ | 2.12 |

Procedure:

Components 4, 8 and 9 were combined and homogenized until smooth at 20000 RPM. Components 1-3, 6-7, 10-12 were added and mixed with a dual asymmetric centrifugal mixer at 2500 RPM for 6 minutes until particulates were no longer visible (Mixture A). In a separate vessel, components 13-17 were mixed with a 4-blade, 40 mm propeller at 550 rpm until homogenous (Mixture B). Mixture B was added to Mixture A dropwise while mixing with a 4-blade 40 mm propeller at 2000 rpm and the mixture was confirmed as homogenous. Component 18 was added to the product of Mixture A and Mixture B and mixed with 4-blade 40 mm propeller at 1000 rpm until homogenous.

Formulation 79-45

A 2:1 blend of Formulations 60-211 and 79-24b was mixed together with a 4-blade 40 mm propeller at 2000 rpm for 2 minutes.

Formulation 79-46

A 1:2 blend of Formulations 60-211 and 79-24b was mixed together with a 4-blade 40 mm propeller at 2000 rpm for 2 minutes.

Formulation 79-41

A 1:5 blend of Formulations 60-211 and 79-24b was mixed together with a 4-blade 40 mm propeller at 2000 rpm for 2 minutes.

Formulation 88-30-1

| Component No. | Component | Percent of Formulation (%) |
|---|---|---|
| 1 | VS500 | 0.68 |
| 2 | MV2000 | 1.02 |
| 3 | VS65,000 | 17.00 |
| 4 | XL-1B | 21.96 |
| 5 | Aerosil R 8200 | 11.51 |
| 6 | Dow 246 Fluid | 10.43 |
| 7 | Crodamol STS | 1.15 |
| 8 | 83-49 | 12.00 |
| 9 | 83-50 | 3.39 |
| 10 | Cabosperse 1030K | 20.87 |

Procedure:

Ingredients 1 through 7 were mixed using a propeller blade at 275 RPM to prepare phase A. In a separate vessel components 8 through 10 were mixed, using a propeller blade at 275 RPM, to prepare phase B. Phase B was mixed into phase A at 275 RPM until the emulsion is uniform. An amount of 0.01% iron oxides was added to the final formulation to impart color. Formulation 83-49 and 83-50 are emulsions of VS 165,000 vinyl siloxane and XL-11 hydride functionalized siloxane, respectively, containing 65% siloxanes, 8% oleth-10 surfactant, and the balance water.

Formulation 83-16

| Component No. | Component | Percent of Formulation (%) |
|---|---|---|
| 1 | Gransil EP-LS ™ | 3.5 |
| 2 | Andisil XL-11 ™ | 9.76 |
| 3 | Andisil VS 1,000 ™ | 25.53 |
| 4 | Andisil VS 165,000 ™ | 5.12 |
| 5 | Aerosil R8200 ™ | 10.23 |
| 6 | Velvesil 125 ™ | 3.51 |
| 7 | Flo-Beads SE-3207B ™ | 1.17 |
| 8 | Sepiplus 400 ™ | 1.22 |
| 9 | Granpowder Nylon ™ | 3.9 |
| 10 | Water | 25.47 |
| 11 | Granhydrogel O ™ | 6.32 |
| 12 | Jeechem BUGL ™ | 3.97 |
| 13 | Neolone PE ™ | 0.22 |
| 14 | Iron Oxide Tint Mixture | 0.08 |

Procedure:

Components 1 and 2 were combined and homogenized until smooth at 20000 RPM (Mixture A). Components 3 to 9 were added and mixed with a dual asymmetric centrifugal mixer at 2500 RPM for 6 minutes until particulates were no longer visible (Mixture B). Mixture A and Mixture B were combined and centrifuge mixed for 6 minutes at 2500 RPM (Mixture A+B). In a separate vessel, components 10 to 13 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 14 was added to the product of Mixture A+B and Mixture C and mixed with 4-blade 40 mm propeller at 1000 rpm until homogenous.

Formulation 79-55a

| Component No. | Component | Percent of Formulation (%) |
|---|---|---|
| 1 | Gransil EP-LS ™ | 3.50 |
| 2 | Andisil XL-11 ™ | 8.17 |
| 3 | Andisil VS 1,000 ™ | 32.59 |
| 4 | Andisil VS 165,000 ™ | 6.52 |
| 5 | Andisil XL-11 ™ | 3.04 |
| 6 | Aerosil R8200 ™ | 13.04 |
| 7 | Sepiplus 400 ™ | 1.14 |
| 8 | Water | 21.76 |
| 9 | Granhydrogel O ™ | 6.40 |
| 10 | Jeechem BUGL ™ | 3.20 |
| 11 | Sodium Chloride | 0.32 |
| 12 | Neolone PE ™ | 0.32 |
| 13 | Iron Oxide Tint Mixture | 0.01 |

Procedure:

Components 1 and 2 were combined and homogenized until smooth at 20000 RPM (Mixture A). Components 3 to 7 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 8 to 12 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 13 was added to the product of Mixture A+B and Mixture C and mixed with 4-blade 40 mm propeller at 1000 rpm until homogenous.

Formulation 79-55b

| Component No. | Component | Percent of Formulation (%) |
|---|---|---|
| 1 | Gransil EP-LS ™ | 3.50 |
| 2 | Andisil XL-11 ™ | 8.17 |
| 3 | Andisil VS 10,000 ™ | 30.33 |
| 4 | Andisil VS 165,000 ™ | 7.10 |
| 5 | Andisil XL-11 ™ | 5.49 |
| 6 | Aerosil R8200 ™ | 12.26 |
| 7 | Sepiplus 400 ™ | 1.14 |
| 8 | Water | 21.76 |
| 9 | Granhydrogel O ™ | 6.40 |
| 10 | Jeechem BUGL ™ | 3.20 |
| 11 | Sodium Chloride | 0.32 |
| 12 | Neolone PE ™ | 0.32 |
| 13 | Iron Oxide Tint Mixture | 0.01 |

Procedure:

Components 1 and 2 were combined and homogenized until smooth at 20000 RPM (Mixture A). Components 3 to 7 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 8 to 12 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 13 was added to the product of Mixture A+B and Mixture C and mixed with 4-blade 40 mm propeller at 1000 rpm until homogenous.

Formulation 79-55c

| Component No. | Component | Percent of Formulation (%) |
|---|---|---|
| 1 | Gransil EP-LS ™ | 3.50 |
| 2 | Andisil XL-1B ™ | 8.17 |
| 3 | Andisil VS 500 ™ | 0.84 |
| 4 | Andisil MV 2,000 ™ | 1.29 |
| 5 | Andisil VS 65,000 ™ | 21.04 |
| 6 | Andisil XL-1B ™ | 17.82 |
| 7 | Aerosil R8200 ™ | 14.20 |
| 8 | Sepiplus 400 ™ | 1.14 |
| 9 | Water | 21.76 |
| 10 | Granhydrogel O ™ | 6.40 |
| 11 | Jeechem BUGL ™ | 3.20 |
| 12 | Sodium Chloride | 0.32 |
| 13 | Neolone PE ™ | 0.32 |
| 14 | Iron Oxide Tint Mixture | 0.01 |

Procedure:

Components 1 and 2 were combined and homogenized until smooth at 20000RPM (Mixture A). Components 3 to 8 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 9 to 13 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 14 was added to the product of Mixture A+B and Mixture C and mixed with 4-blade 40 mm propeller at 1000 rpm until homogenous.

Formulation 79-55d

| Component No. | Component | Percent of Formulation (%) |
|---|---|---|
| 1 | Gransil EP-LS ™ | 3.50 |
| 2 | Andisil XL-1B ™ | 8.17 |
| 3 | Andisil VS 250 ™ | 1.29 |
| 4 | Andisil MV 2,000 ™ | 1.94 |
| 5 | Andisil VS 20,000 ™ | 24.52 |
| 6 | Andisil CE-4 ™ | 1.94 |
| 7 | Andisil XL-1B ™ | 0.33 |
| 8 | Andisil XL-11 ™ | 10.97 |
| 9 | Aerosil R8200 ™ | 14.20 |
| 10 | Sepiplus 400 ™ | 1.14 |
| 11 | Water | 21.76 |
| 12 | Granhydrogel O ™ | 6.40 |
| 13 | Jeechem BUGL ™ | 3.20 |
| 14 | Sodium Chloride | 0.32 |
| 15 | Neolone PE ™ | 0.32 |
| 16 | Iron Oxide Tint Mixture | 0.01 |

Procedure:

Components 1 and 2 were combined and homogenized until smooth at 20000RPM (Mixture A). Components 3 to 10 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 11 to 15 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 16 was added to the product of Mixture A+B and Mixture C and mixed with 4-blade 40 mm propeller at 1000 rpm until homogenous.

Formulation 79-55e

| Component No. | Component | Percent of Formulation (%) |
|---|---|---|
| 1 | Gransil EP-LS ™ | 3.50 |
| 2 | Andisil XL-1B ™ | 8.17 |
| 3 | Andisil VS 250 ™ | 1.29 |
| 4 | Andisil MV 2,000 ™ | 1.94 |
| 5 | Andisil VS 65,000 ™ | 22.91 |
| 6 | Andisil XL-1B ™ | 6.78 |
| 7 | Andisil XL-11 ™ | 8.07 |
| 8 | Aerosil R8200 ™ | 14.20 |
| 9 | Sepiplus 400 ™ | 1.14 |
| 10 | Water | 21.76 |
| 11 | Granhydrogel O ™ | 6.40 |
| 12 | Jeechem BUGL ™ | 3.20 |
| 13 | Sodium Chloride | 0.32 |
| 14 | Neolone PE ™ | 0.32 |
| 15 | Iron Oxide Tint Mixture | 0.01 |

Procedure:

Components 1 and 2 were combined and homogenized until smooth at 20000RPM (Mixture A). Components 3 to 9 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 10 to 14 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 15 was added to the product of Mixture A+B and Mixture C and mixed with 4-blade 40 mm propeller at 1000 rpm until homogenous.

Formulation 79-55f

| Component No. | Component | Percent of Formulation (%) |
|---|---|---|
| 1 | Gransil EP-LS ™ | 3.50 |
| 2 | Andisil XL-1B ™ | 8.17 |
| 3 | Andisil VS 250 ™ | 1.34 |
| 4 | Andisil VS 65,000 ™ | 23.74 |
| 5 | Andisil XL-1B ™ | 7.03 |
| 6 | Andisil XL-11 ™ | 8.36 |
| 7 | Aerosil R8200 ™ | 14.71 |
| 8 | Sepiplus 400 ™ | 1.14 |
| 9 | Water | 21.76 |
| 10 | Granhydrogel O ™ | 6.40 |
| 11 | Jeechem BUGL ™ | 3.20 |
| 12 | Sodium Chloride | 0.32 |
| 13 | Neolone PE ™ | 0.32 |
| 14 | Iron Oxide Tint Mixture | 0.01 |

Procedure:

Components 1 and 2 were combined and homogenized until smooth at 20000 RPM (Mixture A). Components 3 to 8 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 9 to 13 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 14 was added to the product of Mixture A+B and Mixture C and mixed with 4-blade 40 mm propeller at 1000 rpm until homogenous.

Formulation 79-55g

| Component No. | Component | Percent of Formulation (%) |
|---|---|---|
| 1 | Gransil EP-LS ™ | 3.50 |
| 2 | Andisil XL-1B ™ | 8.17 |
| 3 | Andisil VS 250 ™ | 1.29 |
| 4 | Andisil MV 2,000 ™ | 1.94 |
| 5 | Andisil VS 20,000 ™ | 22.91 |
| 6 | Andisil XL-1B ™ | 6.78 |
| 7 | Andisil XL-11 ™ | 8.07 |
| 8 | Aerosil R8200 ™ | 14.20 |
| 9 | Sepiplus 400 ™ | 1.14 |
| 10 | Water | 21.76 |
| 11 | Granhydrogel O ™ | 6.40 |
| 12 | Jeechem BUGL ™ | 3.20 |
| 13 | Sodium Chloride | 0.32 |
| 14 | Neolone PE ™ | 0.32 |
| 15 | Iron Oxide Tint Mixture | 0.01 |

Procedure:

Components 1 and 2 were combined and homogenized until smooth at 20000 RPM (Mixture A). Components 3 to 9 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 10 to 14 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 15 was added to the product of Mixture A+B and Mixture C and mixed with 4-blade 40 mm propeller at 1000 rpm until homogenous.

Formulation 83-54

| Component No. | Component | Percent of Formulation (%) |
|---|---|---|
| 1 | Andisil VS 10,000 ™ | 27.58 |
| 2 | Andisil VS 165,000 ™ | 6.46 |
| 5 | Andisil XL-11 ™ | 13.50 |
| 6 | Aerosil R8200 ™ | 17.50 |
| 7 | Labrafac CC ™ | 3.00 |
| 7 | Sepiplus 400 ™ | 1.44 |
| 8 | Water | 29.29 |
| 9 | Plantacare 818UP ™ | 0.50 |
| 11 | Sodium Chloride | 0.36 |
| 12 | Neolone PE ™ | 0.36 |
| 13 | Iron Oxide Tint Mixture | 0.01 |

Procedure:

Components 1 to 7 were added and mixed with a dual asymmetric centrifugal mixer at 2500 RPM for 6 minutes until particulates are no longer visible (Mixture A). In a separate vessel, components 8 to 12 were mixed with a 4-blade, 40 mm propeller at 550 rpm until homogenous (Mixture B). Mixture B was added to Mixture A dropwise while mixing with a 4-blade 40 mm propeller at 400 rpm and the mixture was confirmed as homogenous. Component 13 was added to the product of Mixture A and Mixture B and mixed with 4-blade 40 mm propeller at 1000 rpm until homogenous.

Formulation 79-55h

| Component No. | Component | Percent of Formulation (%) |
|---|---|---|
| 1 | Gransil EP-LS ™ | 3.50 |
| 2 | Andisil XL-1B ™ | 8.15 |
| 3 | Andisil VS 250 ™ | 1.25 |
| 4 | Andisil MV 2,000 ™ | 1.85 |
| 5 | Andisil VS 20,000 ™ | 24.40 |
| 6 | Andisil CE-4 ™ | 1.85 |
| 7 | Andisil XL-1B ™ | 0.30 |
| 8 | Andisil XL-11 ™ | 10.80 |
| 9 | Aerosil R8200 ™ | 14.20 |
| 10 | Sepiplus 400 ™ | 1.14 |
| 11 | Water | 21.50 |
| 12 | Granhydrogel O ™ | 6.30 |
| 13 | Jeechem BUGL ™ | 3.15 |
| 14 | Sodium Chloride | 0.30 |
| 15 | Neolone PE ™ | 0.30 |
| 16 | Beaver UV/Fluorescent Pigment | 1.00 |

Procedure:

Components 1 and 2 were combined and homogenized until smooth at 20000 RPM (Mixture A). Components 3 to 10 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 11 to 15 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 15 was added to the product of Mixture A+B and Mixture C and mixed with 4-blade 40 mm propeller at 1000 rpm until homogenous.

Formulation 81-18

| Component No. | Component | Percent of Formulation (%) |
|---|---|---|
| 1 | Dow 9011 Elastomer Blend | 10.45 |
| 2 | Dow 9045 Elastomer Blend | 10.45 |
| 3 | Dow 245 Fluid | 8.4 |
| 4 | Jeensilc CPS-312 | 2.09 |
| 5 | PT-50175F | 1.00 |
| 6 | Water | 30.33 |
| 7 | Plantacare 818 UP | 0.55 |
| 8 | Neolone PE | 0.21 |
| 9 | Propylene Glycol | 20.87 |
| 10 | Glycerin | 4.16 |
| 11 | Jeechem BUGL | 10.44 |
| 12 | Sodium Chloride | 1.05 |

Procedure:

Components 1-5 were mixed in a glass beaker at 2000 rpm with 4-blade 40 mm propeller for 2 minutes until mixture was homogeneous (Mixture A). Separately, components 6-12 were mixed until homogenous (Mixture B). Mixture B was added to Mixture A under strong agitation provided by a 4-blade, 40 mm propeller at 2000 rpm until homogeneous. The final formulation was further homogenized for 2 minutes.

Formulation 81-19

| Component No. | Component | Percent of Formulation (%) |
|---|---|---|
| 1 | Dow 9011 Elastomer Blend | 10.45 |
| 2 | Dow 9045 Elastomer Blend | 10.45 |
| 3 | Dow 245 Fluid | 8.4 |
| 4 | Jeensilc CPS-312 | 2.09 |
| 5 | PT-50175F | 1.00 |
| 6 | Water | 29.83 |
| 7 | Plantacare 818 UP | 0.55 |
| 8 | Neolone PE | 0.21 |
| 9 | Propylene Glycol | 20.87 |
| 10 | Glycerin | 4.16 |
| 11 | Jeechem BUGL | 10.44 |
| 12 | Sodium Chloride | 1.05 |
| 13 | Nylon 10-12 | 0.5 |

Procedure:

Components 1-5 were mixed in a glass beaker at 2000 rpm with 4-blade 40 mm propeller for 2 minutes until mixture was homogeneous (Mixture A). Separately, components 6-12 were mixed until homogenous (Mixture B). Mixture B was added to Mixture A under strong agitation provided by a 4-blade, 40 mm propeller at 2000 rpm until homogeneous. Component 13 was then added and the resulting mixture was homogenized for 2 minutes.

Formulation 81-20

| Component No. | Component | Percent of Formulation (%) |
|---|---|---|
| 1 | Dow 9011 Elastomer Blend | 10.45 |
| 2 | Dow 9045 Elastomer Blend | 10.45 |
| 3 | Dow 245 Fluid | 8.4 |
| 4 | Jeensilc CPS-312 | 2.09 |
| 5 | PT-50175F | 1.00 |
| 6 | Water | 29.33 |
| 7 | Plantacare 818 UP | 0.55 |
| 8 | Neolone PE | 0.21 |
| 9 | Propylene Glycol | 20.87 |
| 10 | Glycerin | 4.16 |
| 11 | Jeechem BUGL | 10.44 |
| 12 | Sodium Chloride | 1.05 |
| 13 | Nylon 10-12 | 1.0 |

Procedure:

Components 1-5 were mixed in a glass beaker at 2000 rpm with 4-blade 40 mm propeller for 2 minutes until mixture was homogeneous (Mixture A). Separately, components 6-12 were mixed until homogenous (Mixture B). Mixture B was added to Mixture A under strong agitation provided by a 4-blade, 40 mm propeller at 2000 rpm until homogeneous. Component 13 was then added and the resulting mixture was homogenized for 2 minutes.

Formulation 81-21

| Component No. | Component | Percent of Formulation (%) |
|---|---|---|
| 1 | Dow 9011 Elastomer Blend | 10.45 |
| 2 | Dow 9045 Elastomer Blend | 10.45 |
| 3 | Dow 245 Fluid | 8.4 |
| 4 | Jeensilc CPS-312 | 2.09 |
| 5 | PT-50175F | 1.00 |
| 6 | Water | 27.33 |
| 7 | Plantacare 818 UP | 0.55 |
| 8 | Neolone PE | 0.21 |
| 9 | Propylene Glycol | 20.87 |
| 10 | Glycerin | 4.16 |
| 11 | Jeechem BUGL | 10.44 |
| 12 | Sodium Chloride | 1.05 |
| 13 | Nylon 10-12 | 3.0 |

Procedure:

Components 1-5 were mixed in a glass beaker at 2000 rpm with 4-blade 40 mm propeller for 2 minutes until mixture was homogeneous (Mixture A). Separately, components 6-12 were mixed until homogenous (Mixture B). Mixture B was added to Mixture A under strong agitation provided by a 4-blade, 40 mm propeller at 2000 rpm until homogeneous. Component 13 was then added and the resulting mixture was homogenized for 2 minutes.

Formulation 79-74

| Component No. | Component | Percent of Formulation (%) |
|---|---|---|
| 1 | Andisil VS 10,000 ™ | 27.58 |
| 2 | Andisil VS 165,000 ™ | 6.46 |
| 5 | Andisil XL-11 ™ | 13.50 |
| 6 | Aerosil R8200 ™ | 17.50 |
| 7 | Schercemol ™ 318 Ester | 3.00 |
| 7 | Sepiplus 400 ™ | 1.44 |
| 8 | Water | 29.29 |
| 9 | Plantacare 818UP ™ | 0.50 |
| 11 | Sodium Chloride | 0.36 |
| 12 | Neolone PE ™ | 0.36 |
| 13 | Iron Oxide Tint Mixture | 0.01 |

Procedure:

Components 1 to 7 were added and mixed with a dual asymmetric centrifugal mixer at 2500 RPM for 6 minutes until particulates are no longer visible (Mixture A). In a separate vessel, components 8 to 12 were mixed with a 4-blade, 40 mm propeller at 550 rpm until homogenous (Mixture B). Mixture B was added to Mixture A dropwise while mixing with a 4-blade 40 mm propeller at 400 rpm and the mixture was confirmed as homogenous. Component 13 was added to the product of Mixture A and Mixture B and mixed with 4-blade 40 mm propeller at 1000 rpm until homogenous.

Pigment Dispersion Formulation 80-23

| Component No. | Component | Percent of Formulation (%) |
|---|---|---|
| 1 | Dow 9011 Elastomer Blend | 10 |
| 2 | Dow 9045 Elastomer Blend | 10 |
| 3 | Dow 245 Fluid | 10 |
| 4 | Water | 27 |
| 5 | Plantacare 818 UP | 0.5 |
| 6 | Neolone PE | 0.5 |
| 7 | Propylene Glycol | 20 |
| 8 | Glycerin | 4 |
| 9 | Jeechem BUGL | 10 |
| 10 | Sodium Chloride | 1 |
| 11 | Nylon | 4.5 |
| 12 | Tint | 2.5 |

Procedure:

Components 1-3 were mixed in a glass beaker at 2000 rpm with 4-blade 40 mm propeller for 2 minutes until homogenous (Mixture A). Separately, components 5-10 were mixed until homogenous (Mixture B). Mixture was added B to Mixture A under strong agitation, provided by a 4-blade, 40 mm propeller at 2000 rpm until homogeneous. Components 11 and 12 were then added and mix at 200 rpm and until homogeneous. The final mixture was then homogenized for 2 minutes.

Formulation 79-88

| Component No. | Component | Percent of Formulation (%) |
|---|---|---|
| 1 | Andisil VS 10,000 ™ | 27.59 |
| 2 | Andisil VS 165,000 ™ | 6.46 |
| 3 | Andisil XL-11 ™ | 13.50 |
| 4 | Aerosil R8200 ™ | 17.50 |
| 5 | Labrafac CC ™ | 3.00 |
| 6 | Sepiplus 400 ™ | 1.44 |
| 7 | Water | 29.29 |
| 8 | Plantacare 818UP ™ | 0.50 |
| 9 | Sodium Chloride | 0.36 |
| 10 | Neolone PE ™ | 0.36 |

Procedure:

Components 1 to 4 were combined and mixed with KitchenAid mixer for 5 hours. Subsequently the mixture was vacuumed overnight. Components 5 and 6 were then added and the mixture was homogenized in a dual asymmetric centrifugal mixer at 2500RPM. In a separate vessel, components 7 to 10 were mixed with a 4-blade, 40 mm propeller at 550 rpm until homogenous (Mixture B). Mixture B was added to Mixture A dropwise while mixing with a 4-blade 40 mm propeller at 500 rpm and the mixture was confirmed as homogenous.

Formulation 79-88-3A

| Component No. | Component | Percent of Formulation (%) |
|---|---|---|
| 1 | Andisil VS 10,000 ™ | 27.59 |
| 2 | Andisil VS 165,000 ™ | 6.46 |
| 3 | Andisil XL-11 ™ | 13.50 |
| 4 | Aerosil R8200 ™ | 17.50 |
| 5 | Labrafac CC ™ | 3.00 |
| 6 | Simulgel EG ™ | 1.44 |
| 7 | Water | 29.29 |
| 8 | Plantacare 818UP ™ | 0.50 |
| 9 | Sodium Chloride | 0.36 |
| 10 | Neolone PE ™ | 0.36 |

Procedure:

Components 1 to 4 were combined and mixed with KitchenAid mixer for 5 hours. Subsequently the mixture was vacuumed overnight. Components 5 and 6 were then added and the mixture was homogenized in a dual asymmetric centrifugal mixer at 2500RPM. In a separate vessel, components 7 to 10 were mixed with a 4-blade, 40 mm propeller at 550 rpm until homogenous (Mixture B). Mixture B was added to Mixture A dropwise while mixing with a 4-blade 40 mm propeller at 500 rpm and the mixture was confirmed as homogenous.

Formulation 79-74-RD

| Component No. | Component | Percent of Formulation (%) |
|---|---|---|
| 1 | Andisil VS 500 ™ | 0.52 |
| 2 | Andisil MV 2000 ™ | 0.80 |
| 3 | Andisil VS 65,000 ™ | 13.04 |
| 4 | Andisil XL-1B ™ | 16.84 |
| 5 | Aerosil R8200 ™ | 8.80 |
| 6 | Water | 50.00 |
| 7 | Veegum Pro | 4.00 |
| 8 | Solagum AX | 1.00 |
| 9 | Dow Corning 5329 | 5.00 |

Procedure:

Components 1 to 5 were combined and mixed under vacuum (Mixture A). In a separate vessel, components 6 to 7 were mixed with a 4-blade, 40 mm propeller at 550 rpm until the mixture was homogenous and the particulates were fully wetted (Mixture B). Component 8 was added to Mixture B and mixed in with a 4-blade 40 mm propeller at 500 rpm until the mixture thickened and became homogenous. Component 9 was added to Mixture B and mixed in with a 4-blade 40 mm propeller at 500 rpm for 10 minutes. Mixture A was added slowly to Mixture B under continuous mixing at 500 rpm. The product was homogenized for 5 minutes at 10,000 rpm.

Formulation 79-90-B

| Component No. | Component | Percent of Formulation (%) |
|---|---|---|
| 1 | Andisil VS 500 ™ | 0.68 |
| 2 | Andisil MV 2000 ™ | 1.04 |
| 3 | Andisil VS 65,000 ™ | 16.95 |
| 4 | Andisil XL-1B ™ | 21.89 |
| 5 | Aerosil R8200 ™ | 11.44 |
| 6 | Water | 40.00 |
| 7 | Veegum Pro | 4.00 |
| 8 | Solagum AX | 1.00 |
| 9 | Dow Corning 5329 | 3.00 |

Procedure:

Components 1 to 5 were combined and mixed under vacuum (Mixture A). In a separate vessel, components 6 to 7 were mixed with a 4-blade, 40 mm propeller at 550 rpm until the mixture was homogenous and the particulates were fully wetted (Mixture B). Component 8 was added to Mixture B and mixed in with a 4-blade 40 mm propeller at 500 rpm until the mixture thickened and became homogenous. Component 9 was added to Mixture B and mixed in with a 4-blade 40 mm propeller at 500 rpm for 10 minutes. Mixture A was added slowly to Mixture B under continuous mixing at 500 rpm. The product was homogenized for 5 minutes at 10,000 rpm.

Formulation 88-70

| Component No. | Component | Percent of Formulation (%) |
| --- | --- | --- |
| 1 | Andisil VS10,000 | 28.7% |
| 2 | Andisil VS165,000 | 6.7% |
| 3 | Andisil XL-11 | 14.0% |
| 5 | Aerosil R8200 | 18.2% |
| 6 | KF6013 | 2.1% |
| 7 | TMF 1.5 | 2.3% |
| 8 | USG 102 | 2.3% |
| 9 | DI water | 22.3% |
| 10 | Glycerin | 1.1% |
| 11 | Jeen BUGL | 1.2% |
| 12 | Jeecide Cap-5 | 1.0% |

Procedure:

Components 1-8 (part A) and components 9-11 (part B). Part B was introduced to part A while mixing part A with a flat propeller blade at 500 RPM. The resulting solution was mixed until a uniform emulsion formed. Component 12 was subsequently added to the emulsion.

Formulation 88-72

| Component No. | Component | Percent of Formulation (%) |
| --- | --- | --- |
| 1 | Andisil VS10,000 | 28.60% |
| 2 | Andisil VS165,000 | 6.69% |
| 3 | Andisil XL-11 | 13.99% |
| 5 | Aerosil R8200 | 18.16% |
| 6 | KF6013 | 2.08% |
| 7 | TMF 1.5 | 2.25% |
| 8 | USG 102 | 2.35% |
| 9 | Pink tint mix | 0.02% |
| 10 | DI water | 22.25% |
| 11 | Glycerin | 1.16% |
| 12 | Jeen BUGL | 1.24% |
| 13 | Veegum Ultra Granules | 0.11% |
| 14 | Kaolin USP BC2747 | 0.10% |
| 15 | Jeecide Cap-5 | 1.00% |

Procedure:

Components 1-9 (Phase A) were mixed separately from components 10-14 (Phase B). Phase B was added to Phase A while mixing at 500 RPM using a 4 paddle mixing blade, followed by homogenization using a Silverson homogenizer for 1 hour at 3000 to 5000 RPM. Subsequently, component 15 was added using mixing blade at 200 rpm.

Formulation 88-75-2

| Component No. | Component | Percent of Formulation (%) |
| --- | --- | --- |
| 1 | Andisil VS10,000 | 21.39% |
| 2 | Andisil VS165,000 | 5.00% |
| 3 | Andisil XL-11 | 10.47% |
| 4 | Aerosil R8200 | 13.58% |
| 5 | RM2051 | 1.95% |
| 6 | DC 556 | 3.12% |
| 7 | FZ3196 | 3.11% |
| 8 | Squalane | 1.85% |
| 9 | USG 102 | 6.90% |
| 10 | Jeechem BUGL | 1.85% |
| 11 | DI water | 29.03% |
| 12 | Polyglycol P425 | 1.22% |
| 13 | Jeecide Cap-5 | 0.52% |

Procedure:

Components 1-4 (Phase A) were mixed. Separately, components 5-9 were also mixed (Phase B) until a uniform dispersion was formed. Components 10-12 (Phase C) were also mixed separately. Phase C was slowly introduced into Phase B, while mixing at 700 RPM with 4 blade propeller rod to create a uniform emulsion (Phase D). Phase D was slowly introduced into Phase A at 700 RPM until uniform, and the resulting formulation was mixed for 5 minutes. Component 13 was added and mixed for 2 minutes.

Formulation 88-75-3

| Component No. | Component | Percent of Formulation (%) |
| --- | --- | --- |
| 1 | Andisil VS10,000 | 18.64% |
| 2 | Andisil VS165,000 | 4.36% |
| 3 | Andisil XL-11 | 9.12% |
| 4 | Aerosil R8200 | 11.84% |
| 5 | RM2051 | 2.21% |
| 6 | DC 556 | 3.53% |
| 7 | FZ3196 | 3.52% |
| 8 | Squalane | 2.10% |
| 9 | USG 102 | 7.81% |
| 10 | Jeechem BUGL | 2.10% |
| 11 | DI water | 32.85% |
| 12 | Polyglycol P425 | 1.38% |
| 13 | Jeecide Cap-5 | 0.54% |

Procedure:

Components 1-4 (Phase A) were mixed. Components 5-9 (Phase B) were mixed separately from Phase A until a uniform dispersion was formed. Components 10-12 (Phase C) were also mixed separately from Phase A and Phase B. Phase C was slowly introduced into Phase B, while mixing at 700 RPM with 4 blade propeller rod to create a uniform emulsion (Phase D). Phase D was Slowly introduced to Phase A at 700 RPM until uniform, and mixed for 5 minutes. Component 13 was then introduced to the resulting formulation and mixed for 2 minutes, followed by homogenization at 5000 RPM for 15 minutes.

Formulation 88-80

| Component No. | Component | Percent of Formulation (%) |
| --- | --- | --- |
| 1 | Andisil VS10,000 | 12.72% |
| 2 | Andisil VS165,000 | 2.98% |
| 3 | Andisil XL-11 | 6.23% |
| 4 | Aerosil R8200 | 8.08% |
| 5 | RM2051 | 2.79% |
| 6 | DC 556 | 4.45% |
| 7 | FZ3196 | 4.44% |
| 8 | Squalane | 2.64% |
| 9 | USG 102 | 9.85% |
| 10 | Jeechem BUGL | 2.64% |
| 11 | DI water | 41.44% |
| 12 | Polyglycol P425 | 1.74% |
| 13 | Jeecide Cap-5 | 0.005% |

Procedure:

Components 1-4 (Phase A) were mixed. Components 5-9 (Phase B) were mixed separately from Phase A until a uniform dispersion was formed. Components 10-12 (Phase C) were also mixed separately from Phase A and Phase B. Phase C was slowly introduced into Phase B, while mixing at 700 RPM with 4 blade propeller rod to create a uniform emulsion (Phase D). Component 13 was added to Phase D and mixed for 2 minutes. The resulting emulsion was lowly introduced into Phase A at 700 RPM until uniform, and mixed for 5 minutes, followed by homogenization at 9000 RPM for 7 minutes.

Formulation 88-85-1

| Component No. | Component | Percent of Formulation (%) |
|---|---|---|
| 1 | RM 2051 | 3.28% |
| 2 | FZ 3196 | 4.92% |
| 3 | USG 102 | 12.11% |
| 4 | water | 48.83% |
| 5 | Jeecide CAP-5 | 0.87% |
| 6 | Andisil VS10,000 | 12.72% |
| 7 | Andisil VS165,000 | 2.98% |
| 8 | Andisil XL-11 | 6.23% |
| 9 | Aerosil R8200 | 8.08% |

Procedure:

Components 1-3 (Phase A) were mixed. Component 4 was added while mixing Phase A, until a white emulsion formed. Components 6-9 (Phase B) were mixed and Phase B was subsequently added to the emulsion and mixed for 5 minutes at 1300 RPM. The resulting formulation was homogenized (Silverson) for 5 minutes and component 5 was added, followed by mixing for 2 minutes at 700 RPM with a propeller blade.

Formulation 88-85-2

| Component No. | Component | Percent of Formulation (%) |
|---|---|---|
| 1 | RM 2051 | 2.62% |
| 2 | FZ 3196 | 3.93% |
| 3 | USG 102 | 9.68% |
| 4 | water | 39.03% |
| 5 | Jeecide CAP-5 | 0.78% |
| 6 | Andisil VS10,000 | 18.6% |
| 7 | Andisil VS165,000 | 4.4% |
| 8 | Andisil XL-11 | 9.1% |
| 9 | Aerosil R8200 | 11.8% |

Procedure:

Components 1-3 (Phase A) were mixed. Component 4 was added while mixing phase A until a white emulsion formed. Components, 6-9 (Phase B) were mixed separately and subsequently added to the emulsion while mixing at 1300 RPM for 5 minutes. The mixture was homogenized (Silverson) for 5 minutes. Component 5 was added and the resulting formulation was mixed for 2 minutes at 700 RPM with a propeller blade.

Formulation 88-83-V2

| Component No. | Component | Percent of Formulation (%) |
|---|---|---|
| 1 | RM 2051 | 3.3% |
| 2 | FZ 3196 | 3.3% |
| 3 | DC 2-1184 fluid | 10.0% |
| 4 | USG 102 | 3.3% |
| 5 | water | 46.3% |
| 6 | Jeecide CAP-5 | 0.3% |
| 7 | Andisil VS10,000 | 14.1% |
| 8 | Andisil VS165,000 | 3.3% |
| 9 | Andisil XL-11 | 6.9% |
| 10 | Aerosil R8200 | 9.0% |

Procedure:

Components 1-4 were mixed (Phase A), followed by addition of component 5, until a white emulsion formed. Component 6 was added to the emulsion and mixed for 5 minutes (emulsion base). Components 7-10 (Phase B) were mixed separately and added to the emulsion base at 1300 RPM, followed by mixing for 5 minutes and homogenization (Silverson) for 10 minutes.

Formulation 88-83-V3

| Component No. | Component | Percent of Formulation (%) |
|---|---|---|
| 1 | RM 2051 | 3.3% |
| 2 | DC 2-1184 fluid | 13.3% |
| 3 | water | 49.7% |
| 4 | Jeecide CAP-5 | 0.3% |
| 5 | Andisil VS10,000 | 14.1% |
| 6 | Andisil VS165,000 | 3.3% |
| 7 | Andisil XL-11 | 6.9% |
| 8 | Aerosil R8200 | 9.0% |

Procedure:

Components 1 and 2 were mixed (Phase A), followed by addition of component 3, until a white emulsion formed. Component 4 was added to the emulsion and mixed for 5 minutes (emulsion base). Components 5-8 (Phase B) were mixed separately and added to the emulsion base at 1300 RPM, followed by mixing for 5 minutes and homogenization (Silverson) for 10 minutes.

Formulation 83-54

Reactive Constituent and Reinforcing Constituent Composition (Vinyl, Hydride, Fumed Silica)

| | | weight percent | ranges lower | ranges upper |
|---|---|---|---|---|
| Tradename | Description | | | |
| Andisil VS10,000 | 0.05 mmol/g vinyl, 10,000 cSt | 42.40% | 30 | 50 |
| Andisil VS165,000 | 0.015 mmol/g vinyl, 165,000 cSt | 9.92% | 5 | 15 |
| Andisil XL-11 | 4.35 mmol/g, 45 cSt | 20.75% | 10 | 30 |
| Aerosil R8200 | Silica Silylate | 26.93% | 20 | 34 |
| | total | 100.00% | | |
| Reactive Reinforcing Component | | | | |
| RM 2051 Thickening Agent | Sodium Polyacrylate (and) Dimethicone (and) Cyclopentasiloxane (and) Trideceth-6 (and) PEG/PPG-18/18 Dimethicone | 3.63% | 3.00% | 5.00% |

-continued

|  | Description | weight percent | ranges lower | ranges upper |
|---|---|---|---|---|
| Gransurf 90 | Cetyl PEG/PPG-10/1 Dimethicone | 0.50% | 0.20% | 2.00% |
| PMX-1184 | dimethicone and trisiloxane | 13.63% | 10.00% | 40.00% |
| Water | N/A | 46.00% | 20.00% | 60.00% |
| Vitamin-C complex | Ascorbic Acid | 0.08% | 0.05% | 0.50% |
| Jeecide CAP-5 | Phenoxyethanol, Caprylyl Glycol, Potassium Sorbate, Aqua, Hexylene Glycol | 0.33% |  | 1.00% |
| Tween 20 | Polysorbate 20 | 0.33% |  | 5.00% |
| Vitamin-A complex | Vitamin A Palmitate 1.7 MIU/g | 0.40% |  | 5.00% |
| Vitamin-E complex | Vitamin E Acetate | 0.10% |  | 5.00% |
| Reactive constituent and Reinforcing constituent composition (Vinyl, hydride, fumed silica) from above | N/A | 35.00% | 30.00% | 60.00% |
|  | total | 100.00% |  |  |

Procedure:

Formulation 83-54 was prepared by a procedure similar to 88-83-V3.

Andisil VS10,000, Andisil VS165,000, Andisil XL-11 were obtained from Anderson and Associates. Aerosil R8200 was obtained from Evonik, and the four components were mixed by Crisil. RM 2051 Thickening Agent and PMX-1184 were obtained from Dow. Gransurf 90 was obtained from Grant. Vitamin-C complex and Vitamin A comples were obtained from DSM. Jeecide CAP-5 was obtained from Jeen. Tween 20 was obtained from Croda. Vitamin-E complex was obtained from TRI-K.

The cross-linking component second step includes formulations 60-148-99, 60-144-San 86-114, and 86-141c shown below.

Formulation 60-148-99

| Component No. | Component | Percent of Formulation (%) |
|---|---|---|
| 1 | Water | 28.60 |
| 2 | Plantacare 818UP | 0.49 |
| 3 | Propylene Glycol | 19.72 |
| 4 | Glycerin | 3.94 |
| 5 | Jeechem BUGL | 9.86 |
| 6 | Sodium Chloride | 0.99 |
| 7 | Dow Elastomer Blend 9011 | 9.86 |
| 8 | Dow Elastomer Blend 9041 | 9.86 |
| 9 | Dow 245 Fluid | 7.89 |
| 10 | Jeensilc CPS-312 | 1.97 |
| 11 | Nylon 10-12 | 4.64 |
| 12 | Chronosphere Optical Brite | 0.18 |
| 13 | Platinum divinyl complex PC 075.3 | 1.00 |

Procedure:

Components 1-6 were combined and mixed at 750 RPM for two minutes with a 4-blade 40 mm propeller until homogenous to create an aqueous phase. In a separate container components 7-10 were mixed at 750 RPM for two minutes with a 4-blade 40 mm propeller until homogenous to create a Silicon Mixture A. To the aqueous phase, components 11 and 12 were added and mixed at 750 RPM with a 4-blade 40 mm propeller. The mixing speed was increased to 1000 RPM and the mixture was mixed until homogenous and thickened. Component 13 was added and stirred at 1000 RPM for 1 minute, then homogenized at 25,000 RPM for 5 minutes.

Formulation 60-144-San

| Component No. | Component | Percent of Formulation (%) |
|---|---|---|
| 1 | Water | 67.47 |
| 2 | Carbopol Ultrez 21 | 1.01 |
| 3 | Denatured Ethanol 190 Proof | 29.35 |
| 4 | Glycerin | 2.02 |
| 5 | 2% Sodium Hydroxide | 0.20 |
| 6 | Platinum divinyl complex 3% PC 075.3 | 1.99 |

Procedure:

Components 1 and 2 were gently blended with a 4-blade 40 mm propeller blade at 250 RPM until the Carbopol was completely wetted and the mixture was free of white particulates. Components 3 and 4 were added under moderate agitation provided by a 4-blade 40 mm propeller at 500 RPM. Component 5 was added dropwise under moderate agitation provided by a 4-blade 40 mm propeller at 550 RPM until the mixture was homogenous and thickened. Component 6 was added under moderate agitation provided by a 4-blade 40 mm propeller at 550 RPM, followed by mixing at 1000 RPM for 5 minutes until the mixture was homogeneous.

Formulation 86-114 and 86-141c

| Tradename | Description | weight percent | Supplier | lower | upper |
|---|---|---|---|---|---|
| Platinum Divinyl Complex 2% PT-50175F (CAS# 68478-92-2, 2627-95-4, 68083-19-2) | Karstedt's catalyst in stabilizing vinyl-dimethicone | 1.00% | Umicore | 0.50% | 2.50% |
|  |  | 1.00% total |  |  |  |

| 86-114 | Crosslinking Component # 1 | | | lower | upper |
|---|---|---|---|---|---|
| Dow 9011 Elastomer Blend | Cyclopentasiloxane (and) PEG-12 Dimethicone Crosspolymer | 10.00% | Dow Corning | 5.00% | 20.00% |
| Dow 9045 Elastomer Blend | Cyclopentasiloxane and Dimethicone Crosspolymer | 10.00% | Dow Corning | 5.00% | 20.00% |
| PMX -0245 | Cyclopentasiloxane | 10.00% | Dow Corning | 5.00% | 25.00% |
| Water | | 28.50% | NA | — | 90.00% |
| Sodium Chloride | Sodium Chloride | 1.00% | Spectrum | — | 5.00% |
| Plantacare 818 UP | Coco-Glucoside | 0.50% | Cognis | — | 4.00% |
| Tween 20 | Polysorbate 20 | 0.00% | Cognis | — | 2.00% |
| Propylene Glycol | Propylene Glycol | 20.00% | Ruger Chemical Co | — | 40.00% |
| Lipo Polyglycol ® 200 | PEG-4 | 0.00% | Lipo Chemicals Inc | — | 40.00% |
| Glycerin | Glycerin | 4.00% | Ruger Chemical Co | — | 10.00% |
| Jeechem BUGL | 1,3-Butylene Glycol | 10.00% | Jeen | — | 50.00% |
| Nylon 10-12 | Nylon 12 and Isopropyl Titabium Triisostearate | 4.50% | KOBO | — | 15.00% |
| Jeecide CAP-5 | Phenoxyethanol, Caprylyl Glycol, Potassium Sorbate, Aqua, Hexylene Glycol | 0.50% | Jeen | — | 2.00% |
| PT-50175F | Platinum Divinyldisiloxane | 1.00% | Umicore | 0.50% | 2.50% |
| | total | 100.00% | total | | |

| 86-141c | Crosslinking Component #2 | | | lower | upper |
|---|---|---|---|---|---|
| KSG-240 | Dimethicone/PEG-10/15 Crosspolymer | 10.00% | Shin Etsu | 3.00% | 20.00% |
| DC 9045 | Cyclopentasiloxane and Dimethicone Crosspolymer | 7.50% | Dow Corning | | 25.00% |
| KF-995 | Cyclopentasiloxane | 11.50% | Shin Etsu | | 25.00% |
| KF-6028 | PEG-9 Polydimethylsiloxyethyl Dimethicone | 1.00% | Shin Etsu | | 4.00% |
| Water | | 28.25% | NA | | 90.00% |
| Sodium Chloride | Sodium Chloride | 1.00% | Spectrum | | 5.00% |
| Plantacare 818 UP | Coco-Glucoside | 0.50% | Cognis | | 4.00% |
| Tween 20 | Polysorbate 20 | 0.00% | Cognis | | 2.00% |
| Propylene Glycol | Propylene Glycol | 20.00% | Ruger Chemical Co | | 40.00% |
| Lipo Polyglycol ® 200 | PEG-4 | 0.00% | Lipo Chemicals Inc | | 40.00% |
| Glycerin | Glycerin | 4.00% | Ruger Chemical Co | | 10.00% |
| Jeechem BUGL | 1,3-Butylene Glycol | 10.00% | Jeen | | 50.00% |
| Nylon 10-12 | Nylon 12 and Isopropyl Titabium Triisostearate | 4.50% | KOBO | | 15.00% |
| Jeecide CAP-5 | Phenoxyethanol, Caprylyl Glycol, Potassium Sorbate, Aqua, Hexylene Glycol | 0.50% | Jeen | | 2.00% |
| PT-50175F | Platinum Divinyldisiloxane | 1.25% | Umicore | | 2.50% |
| | | 100.00% | total | | |

Procedure for 86-114:

Components 1-3 were combined and mixed at 750 RPM for two minutes with until homogenous to create an silicone phase. In a separate container components 4-11 and 13 were mixed at 750 RPM for 15 minutes with a until homogenous to create a water phase. The water phase was added slowly to the silicone phase and mixed at 750 RPM. The mixing speed was increased to 2000 RPM and the mixture was mixed until homogenous and thickened. Component 12 was added and stirred at 1000 RPM for 5 minutes. Component 14 was added and stirred at 1000 RPM for 5 minutes.

Procedure for 86-141c:

Components 1-4 were combined and mixed at 750 RPM for two minutes with until homogenous to create an silicone phase. In a separate container components 5-12 and 14 were mixed at 750 RPM for 15 minutes with a until homogenous to create a water phase. The water phase was added slowly to the silicone phase and mixed at 750 RPM. The mixing speed was increased to 2000 RPM and the mixture was mixed until homogenous and thickened. Component 13 was added and stirred at 1000 RPM for 5 minutes. Component 15 was added and stirred at 1000 RPM for 5 minutes.

Example 6: A 2 Day Double Blinded Study, Evaluating 2 Different Formulations to Achieve a Cosmetic Benefit on Aged Skin Purpose:

The goal of the study was to identify the lead candidates, of 2 different formulation candidates, to advance to a subsequent confirmatory clinical study. Selection criteria was based on the immediately visualizable improvements in the appearance of fine lines, evenness in skin tone, skin texture and pores, as well as the duration of the effect over a six hour period. An additional goal was to determine the ease of application of each formulation for a typical user when self-applying.

Background:

This trial was an early stage development project focused on bringing polysiloxane based reactive systems to topical human use studies. Currently, the performance evaluation studies have been restricted to supervised, limited-use applications. The systems evaluated consisted of vinyl terminated polysiloxanes, silicon hydride functionalized polysiloxanes, fumed silica particles, and a platinum catalyst. In these studies, the polysiloxane systems were applied to the skin surface and cured by the addition of the platinum catalyst.

Test Material Composition:

The formulation compositions under consideration generally consisted of the following ingredients:
vinyl terminated polysiloxane,
hydride functional polysiloxane,
fumed silica particles,
platinum catalyst, and
Commercially available cosmetic ingredients.

The polysiloxanes under consideration all exceeded a molecular weight of 600 Daltons. The percent compositions of the polysiloxanes evaluated are summarized in the table below. These represent the upper concentration ranges of the siloxane and fumed silica materials present in the total formulation. For example, the addition of cosmetic ingredients at a level of 50% would lead to a dilution of each ingredient by a factor of 2, such that composition number 1 was a 35% vinyl terminated polysiloxane, 15% hydride functional polysiloxane, 0% fumed silica, and 50% commercially available cosmetic ingredients. The platinum catalyst in the final formulation was always present at concentrations less than 500 ppm. The two treatments tested were formulations 60-140-1 and 60-140-LX2 and the cross-linking component used was 60-148-99.

Subject Enrollment:

Number of subjects: Approximately 25 subjects were screened in order to enroll a total of 20 subjects to ensure that at least 15 subjects completed the study.

Informed Consent and Release Form: Two copies of a statement of informed consent were given to each subject before the start of this study. The subject was given the opportunity to have her questions answered to her satisfaction. However, if further questions existed, the subject was given sufficient time on the first visit to clarify open questions and concerns regarding the study and/or the informed consent with the investigator prior to signing.

Subject Identification: Subjects were assigned a three-digit number which, when used in conjunction with the clinical study number, uniquely identified every subject in the study. This number remained with the subject throughout the study.

Eligibility Criteria:

The Fitzpatrick skin classification is based on the unprotected appearance response of the skin to the first 30 to 45 minutes of sun exposure after a winter season without sun exposure. The categories of skin types are as follows:
I Always burns easily; never tan s
II Always burns easily; tan s minimally
III Burns moderately, tan s gradually
IV Burns minimally; always tan s well
V Rarely burns; tan s profusely
VI Never burns; deeply pigmented Inclusion:
1. 30-65 years old
2. Female
3. Fitzpatrick skin types I-IV
4. Shows some visible sign of aging on the face including but not limited to: large pores, fine lines and wrinkles, or poor skin tone/texture
5. Willingness to cooperate and participate by following study requirements for the duration of the study and to report any adverse symptoms immediately
6. Little or no erythema due to sun exposure at the treatment site at the time of treatment
7. Able to refrain from using topical skin care products not included in the study on the treatment areas during the course of the study.

Exclusion:
1. Fitzpatrick skin types V-VI
2. Individuals with a known history of allergy or sensitivity to the cosmetic study cream ingredients
3. Individuals with known atopic skin diseases or neurodermatitis
4. Women known to be pregnant, nursing, or planning to become pregnant within 6 months
5. Individuals known to be treated for cancer or have a history of cancer
6. Individuals with observable sunburn, suntan, scars, uneven tone/pigmentation, or other dermal conditions on the test areas that might influence the test results
7. Any active dermatologic condition(s) that might interfere with clinical assessments (e.g., tattoos, eczema, psoriasis, rosacea, acne, etc)

Study Procedure:

Table 2 below outlines the procedures performed each visit of the study:

TABLE 2

| Order of Events on Each Day: | Day 1 time 0 | Day 1 time 6+ hrs | Day 8 time 0 | Day 8 time 6+ hrs |
|---|---|---|---|---|
| Informed consent. qualify | x | | | |
| Cosmetic product application history taken | x | | | |
| Sensitivity to formulations test on arm | x | | | |
| Panelist's face cleaned | x | | x | |

TABLE 2-continued

| Order of Events on Each Day: | Day 1 time 0 | Day 1 time 6+ hrs | Day 8 time 0 | Day 8 time 6+ hrs |
|---|---|---|---|---|
| Baseline photograph taken | x | | x | |
| Formulations applied | x | | x | |
| After application photograph taken | x | | x | |
| After application live evaluation taken | x | | x | |
| After duration photograph taken | | x | | x |
| After duration live evaluations taken | | x | | x |
| Test articles removed | | x | | x |
| Moisturizer applied | | x | | x |

Preparation:

Prior to any panelist's arrival, the 2 formulations were randomized such that the investigator and photographer are not aware of the identity of each formulation.

Photography:

Panelists were photographed under two different lighting conditions (parallel polarized lighting and cross polarized lighting) and at two different camera angles relative to the plane of the face (90°, 45°). Panelists were positioned in a facial positing system to reduce dorsal-ventral rotation and to position the face in approximately the same location relative to the camera each time. Refer to "Photo set up capture" example in "Image analyses measures" section Visit 1:
1. Upon arrival, individuals were evaluated against the exclusion/inclusion criteria and were recruited for the study if they met the requirements
2. After recruitment, subjects were given a brief description of the study and an informed consent form and signed (along with a witness) after all questions about the study had been adequately answered
3. After signing all the paperwork, subjects were assigned the next available subject number
4. The two formulations that were tested on that subject according to the randomization scheme were then be applied by the investigator in a small area on the subject's arm and allowed to remain for 5 minutes to determine any sensitivity to the products
5. If the panelist was not sensitive to the product then they had their face cleaned with a gentle facial cleanser
6. After washing the face, a baseline photograph was taken of the subject's whole face
7. After the baseline photograph, the subject was asked to apply the test materials to the entire upper half of her face (below eyes to hairline, avoiding area below cheek bones), using the finger to apply, under supervision
8. The panelist was then photographed after 2-5 min to obtain the after application photograph
9. The panelist was then asked to complete a questionnaire about the test products applied
10. The investigator completed a live-evaluation of the panelist for efficacy against baseline
11. The panelist was then be allowed to leave for 6-8 hours and given the following instructions:
    a. Do not rub or scratch the face
    b. Do not shower or get the face wet
    c. Do not apply additional products to the face
    d. If any adverse event occurs in the area of application, the panelist should call the investigator and come in for evaluation and removal of the film.
12. Once the panelist returned they were photographed and the panelist and investigator completed evaluation forms
13. If an expert live assessor was scheduled for that evening then the panelist was instructed to wait until the assessment period at which point the assessors graded the appearance of the panelist against their baseline photograph
14. After assessment the panelist was then given an assessment form to leave their impressions and comments on each product
15. After assessment was finished the panelist was then instructed on the removal of the product using makeup remover and did so
16. A commercial skin care moisturizer with SPF15 was then applied to the panelist's face as a moisturizer
17. The panelist was then dismissed Visit 2:
1. Upon arrival, the panelist had their face cleaned with a gentle facial cleanser
2. After washing the face, a baseline photograph was be taken of the subject's whole face
3. After the baseline photograph, the subject was instructed on the method of application (see below) for each formulation and allowed to apply each formulation to the entire upper half of their face according to the randomization scheme in Appendix A (switching the side of application compared to the previous visit)
4. The procedure then continued as in Visit 1 step 7

Photographic Analysis:

After the study concluded, the "baseline", "after application", and "after 6-8 hour" photographs were compiled into a blinded deck and submitted to an expert assessor to grade the extent of wrinkling in each photograph using the Griffiths scale exampled below:
- 0-1: No damage
- 2-3: Mild damage
- 4-5: Moderate damage
- 6-7: Moderate to severe damage
- 8-9: Severe damage The deck was assembled such that the timepoint for the picture being evaluated was not known. This was done to eliminate any bias for an expected result from the evaluation. Because the Griffiths score is an absolute one, differences from baseline were calculated afterwards in the data analysis.

Results:

Evaluation Forms: From the Investigator Evaluation Forms a scale of −2, −1, 0, +1, +2 (for Strong Reduction/Lift, Some Reduction/Lift, No Reduction/Lift, Some Increase/Drop and Strong Increase/Drop), was created for all of the different parameters evaluated. For each formulation, the average value on this scale was determined across the panelists along with the standard deviation to give an indication of performance for each attribute being evaluated.

From the Assessor Evaluation Forms the same scale of −2, −1, 0, +1, +2 were applied to obtain the same statistical data in regards to the evaluations it contained. From these average values and standard deviations, confidence in the ability of each individual formula to affect the parameter being investigated was determined.

Panelist Evaluation Forms were on a scale of −1, 0, +1 for each attribute being evaluated. The average value on this scale was determined per panelist both after application and after duration to give an indication of short and long term performance. The trending of this result was evaluated against the assessor and investigator evaluation results for correlation.

Comments on all three forms were tracked and examined for any similarities. Because the expert assessor did not have an evaluation for each week, only the investigator and panelist forms were compared across the week for consistency in efficacy for each formulation despite the side of the face to which it was applied.

Photographic Analysis:

For the post-clinical photographic analysis, each picture was assigned a Griffiths score by the evaluator. The average change in this score from the corresponding baseline picture for each formulation gave an indication of its efficacy at smoothening the appearance of fine lines and wrinkles as well as creating a more youthful look. These results were compared to the live assessments for correlation.

Week 2 Results Overview: As Table 3 below shows, 60-140-LX2 was far less durable compared to 60-140-1.

TABLE 3

| Formula | % Didn't Fail | n = |
|---|---|---|
| 60-140-LX2 | 65.38% | 26 |
| 60-140-1 | 86.84% | 38 |

Figure 3:
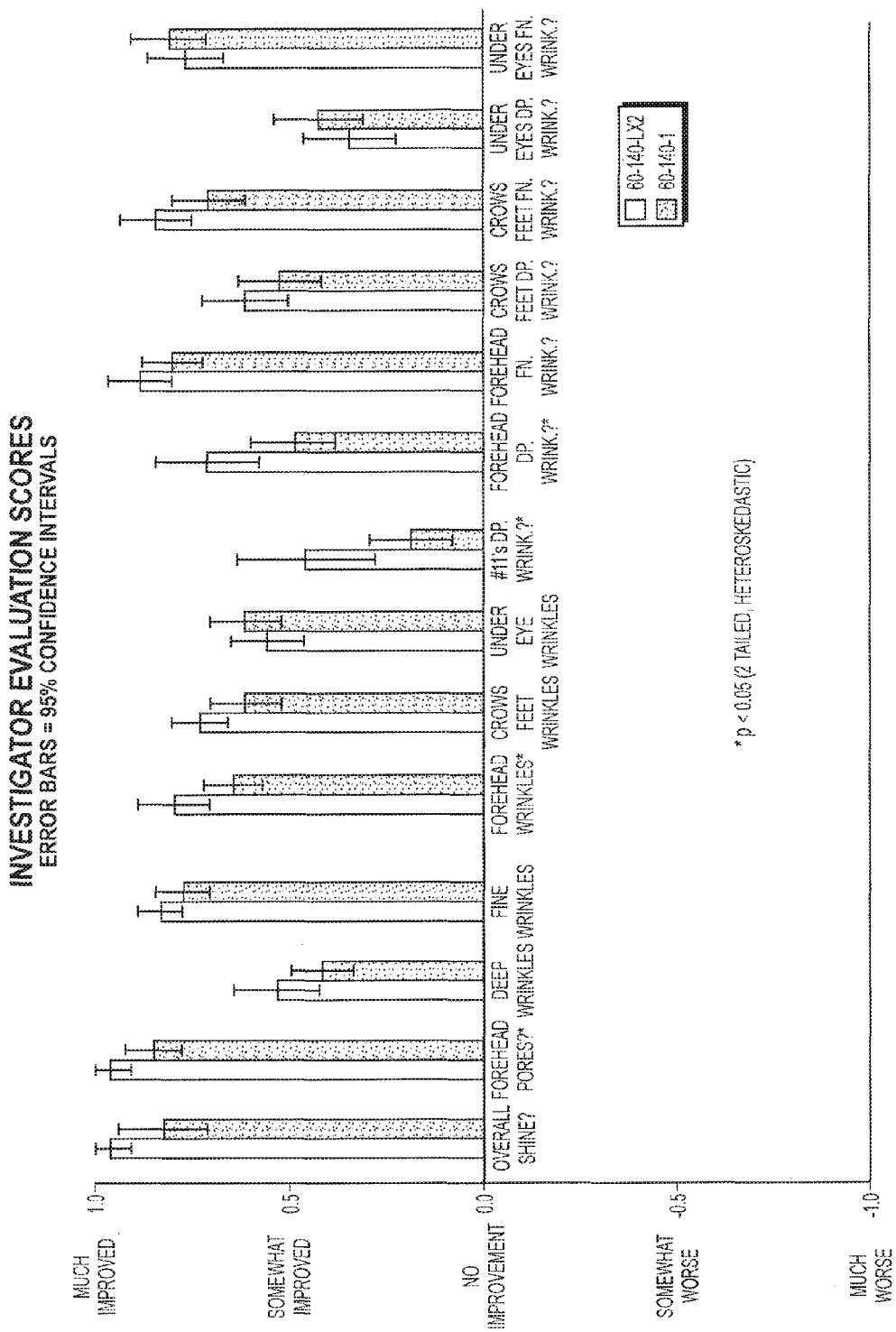
FIG. 3 is a chart illustrating the investigator's assessment of two formulations by attribute in a randomized double blind clinical trial. The formulations are provided in Example 5. The attributes scored included extent of shine reduction, pore reduction, deep wrinkle reduction and fine wrinkle reduction. For all attributes the applications of these two films provided an improvement for the 22 subjects evaluated. These four attributes were further detailed by treatment site. These sites are forehead, crow's feet, undereye, and the nose bridge ('number 11's'). Improvements were observed for each targeted treatment area.

The Investigator assessment of the panelists revealed two significant differences between the performance of the two formulations (see FIG. 3). Formulation 60-140-LX2 showed a significantly greater overall improvement in the appearance of Forehead wrinkles. Conversely 60-140-1 showed a significantly greater improvement in the appearance of Under Eye wrinkles. This is significant in that it confirmed the hypothesis that a softer formulation should be applied to the thinner skin under the eyes to achieve a positive result. Alternatively, because the skin is thicker on the forehead, a stiffer film may be needed to produce a stronger wrinkle reduction. Mattification, reduction of Fine Wrinkles and Pore Reduction were the top three overall performers according to the investigator assessments.

Figure 4:
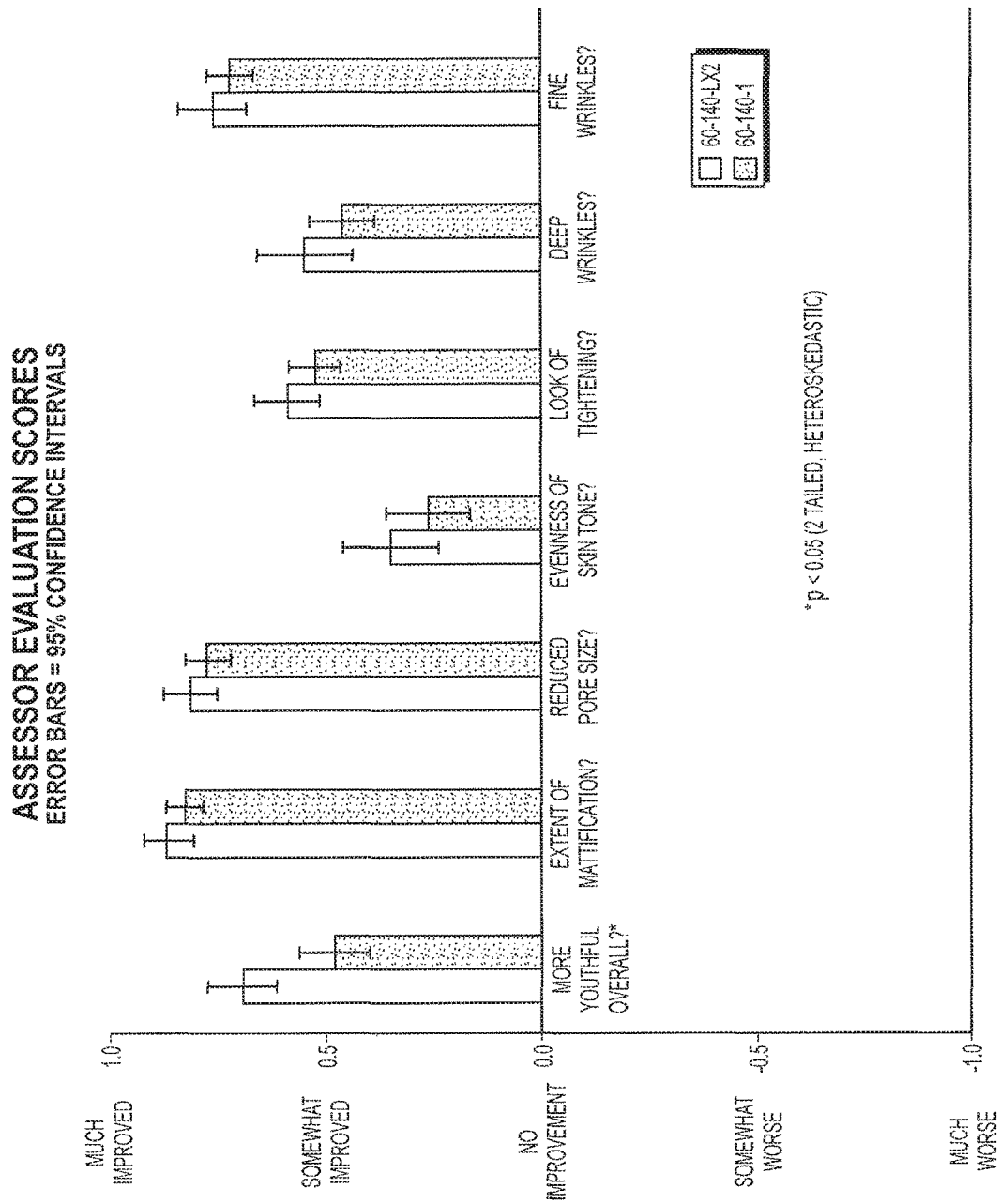
FIG. 4 is a chart illustrating the assessor's assessment of two formulations described in Example 5 by attribute in a randomized double blind clinical trial. The assessor's assessments show an improvement in each of the beauty attributes scored following application of the formulations.

The assessors were able to distinguish differences in three attributes between the two formulations (see FIG. 4). Formulation 60-140-LX2 showed a significant increase in More Youthful Appearance and Natural Feel vs. 60-140-1, while formulation 60-140-1 showed a significantly greater Look of Tightening vs. 60-140-LX2. All other attributes showed no significant difference between the two formulas. The top three attributes for greatest overall change observed show that no matter what the formula mattification, reduced pores and improved fine wrinkles consistently showed the largest noticeable improvement vs. baseline.

Figure 5:
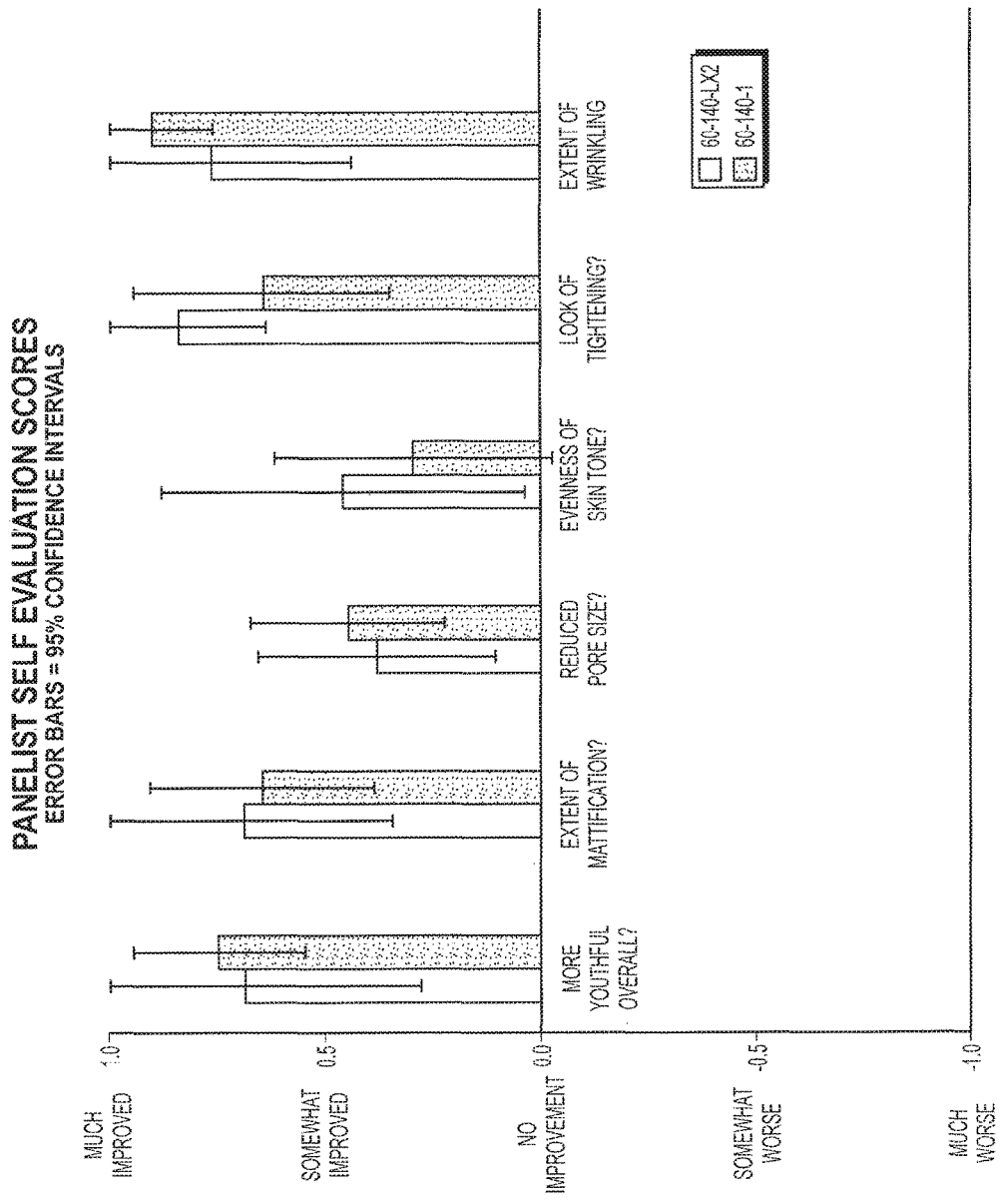
FIG. 5 is a chart illustrating the panelist's assessment of two formulations described in Example 5, by attribute, in a randomized double blind clinical trial. The attributes evaluated were youthful appearance, mattification (or shine reduction), pore size, even skin tone, tightened skin appearance, and wrinkling. For each attribute, the panelists, on average experienced an improvement in each benefit following treatment with the formulations.

Panelist data showed no significant differences between the two formulas tested (see FIG. 5). The top average scorer for 60-140-LX2 was the Look of Tightening attribute. The difference between 60-140-LX2 and 60-140-1 for this attribute was not significant (p~0.24), but it was the most significantly different attribute of those examined below. The sample size was very small for this study so the difference may not have been significantly detectable without further testing. One hypothesis for why this attribute stands above More Youthful Appearance, Extent of Wrinkling and Mattification is that the panelist's may have perceived the feeling of Tightness greatest in 60-140-LX2 thus rating that formula higher than 60-140-1. Discounting this result, the top three performing attributes are More Youthful overall, Reduced Wrinkling and Mattification. Pore size did not stand out among the panelists although for both the assessors and investigators, this attribute was always highly ranked. It may be that the panelists do not remember their baseline pore size.

Figure 6:
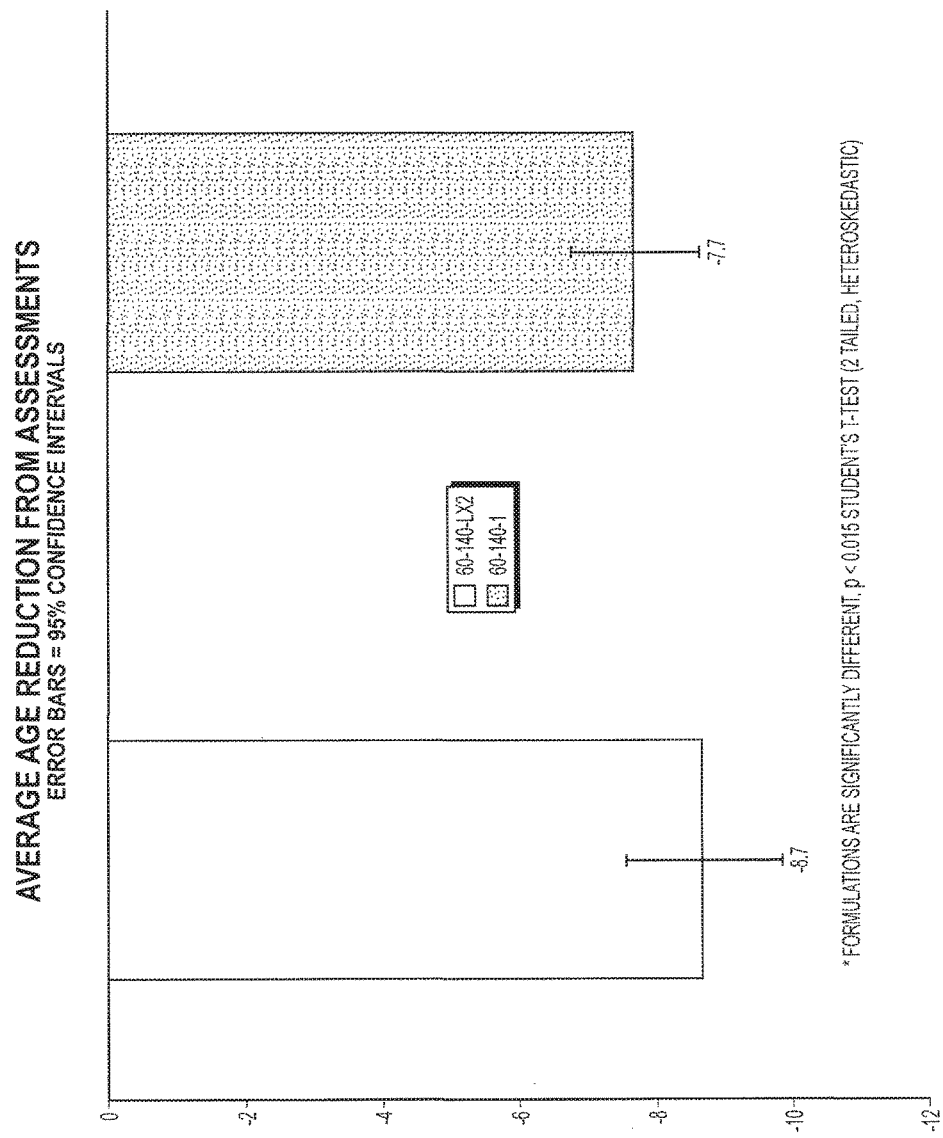
FIG. 6 is a chart illustrating the average age reduction of the panelists as determined by the assessors. Overall age reductions of 8.7 years and 7.7 years age were observed for formulation 60-140-LX2 and for formulation 60-140-1, respectively.

Finally, assessors were asked to estimate the Panelist's age at each assessment. The difference between this age and their real age was then calculated and it was found that 60-140-LX2 had a more significant effect on the age estimate by −8.7 years compared to −7.7 years with 60-140-1. (see FIG. 6).

The Panelist's were also assessed on the Griffith's scale, using before and after pictures. FIG. 7 illustrates the average Griffith's score result from the blinded evaluation of the panelist's photographs. For the two examples, the average Griffith's score was reduced by 2.15 and by 1.25 points, following application of formula 60-140-LX2 and 60-140-1, respectively. This result is consistent with FIGS. 4 and 5, where panelists appeared younger following formulation application.

Study Investigator's Evaluation:

A significant improvement was observed in the reduced appearances of wrinkles, pores and shine. The treatments using two formulations selected from the first week (60-140-LX2 and 60-140-1) on the panelist's upper half face reduced appearance of fine wrinkles of the panelists according to the study investigator evaluations. 60-140-LX2 reduced the appearance of fine wrinkles by 100% while 60-140-1 reduced them by 96% (Table 4). These formulations also reduced deep wrinkles but to a lesser extent (75% and 67% respectively) compared to fine wrinkles.

TABLE 4

| Wrinkle Reduction | Target | A Reduction Seen | No Reduction or Worsened | Out of |
|---|---|---|---|---|
| 60-140-LX2 | Deep Wrinkles | 75.49% | 24.51% | 102 |
|  | Fine Wrinkles | 100.00% | 0.00% | 78 |
| 60-140-1 | Deep Wrinkles | 67.11% | 32.89% | 152 |
|  | Fine Wrinkles | 95.76% | 4.24% | 118 |

Among different types of wrinkles, wrinkles on the forehead (94% and 93%) and crow's feet (96% and 87%) areas were shown to be reduced the most by 60-140-LX2 and 60-140-1 formulations. Under eye wrinkles were also shown to be moderately reduced (81% and 79%) along with the forehead frowning wrinkles (The deep #11's wrinkles), which were only marginally reduced (58% and 31%) (Table 5).

TABLE 5

| Wrinkle Reduction | Target | A Reduction Seen | No Reduction or Worsened | Out of |
|---|---|---|---|---|
| 60-140-LX2 | Forehead Wrinkles | 94.23% | 5.77% | 52 |
|  | #11's Dp. Wrink.? | 58.33% | 41.67% | 24 |
|  | Crows Feet Wrinkle | 96.15% | 3.85% | 52 |
|  | Under Eye Wrinkles | 80.77% | 19.23% | 52 |
| 60-140-1 | Forehead Wrinkles | 92.50% | 7.50% | 80 |
|  | #11's Dp. Wrink.? | 31.25% | 68.75% | 32 |
|  | Crows Feet Wrinkle | 87.18% | 12.82% | 78 |
|  | Under Eye Wrinkles | 78.75% | 21.25% | 80 |

The pores on the forehead appeared to reduce by 100% for both treatments and pores in the cheek also appeared to reduce by 50% and 67% upon treatment using 60-140-LX2 and 60-140-1 (Table 6).

TABLE 6

| Pores | Target | A Reduction Seen | No Reduction or Worsened | Out of |
|---|---|---|---|---|
| 60-140-LX2 | Forehead Pores? | 100.00% | 0.00% | 26 |
|  | Cheek Pores | 50.00% | 50.00% | 8 |
| 60-140-1 | Forehead Pores? | 100.00% | 0.00% | 40 |
|  | Cheek Pores | 66.67% | 33.33% | 6 |

Both formulations reduced the appearance of shine on the panelists' treated skin (Table 6).

TABLE 7

| Shine? | A Reduction Seen | No Reduction or Worsened | Out of |
|---|---|---|---|
| 60-140-LX2 | 100.00% | 0.00% | 26 |
| 60-140-1 | 95.00% | 5.00% | 40 |

Overall the aesthetic performance of these two formulations was comparable in terms of reduction in wrinkles, pores and shine. However, the mechanical performance showed the difference in terms of film intactness and failure where the stiffer film showed failure modes like peeling and cracking (see Tables 8 and 9)

TABLE 8

| Formula | % Didn't Fail | Out of |
|---|---|---|
| 60-140-LX2 | 65.38% | 26 |
| 60-140-1 | 86.84% | 38 |

TABLE 9

| Other Issues | Cracking | Peeling | Whitening | Out of |
|---|---|---|---|---|
| 60-140-LX2 | 26.92% | 11.54% | 34.62% | 26 |
| 60-140-1 | 2.63% | 2.63% | 44.74% | 38 |

Formulation 60-140-1 showed greater film durability after formed on the skin surface and only about 13% showed film failure as determined by film cracking and peeling. 60-140-LX2, however, showed greater film failure (35%) indicating poor durability of the film when formed on the skin which resulted in more cases of film cracking (27%) and peeling (12%). In summary, 60-140-1 was able to provide an "all day" durable film and was a desirable skin care treatment for improving the skin appearance by reducing wrinkles, pores and shine.

Assessors' Evaluation:

The assessors' evaluation showed reduction of wrinkles, pores and shine in the panelists' applied skin. Wrinkle reduction by the treatment of 60-140-LX2 and 60-140-1 were comparable (Table 10).

TABLE 10

| Wrinkles | ShortQ | Improved Group | No Change or Worsened | Out of |
|---|---|---|---|---|
| 60-140-LX2 | Overall Wrinkles | 80.22% | 19.78% | 182 |
|  | Deep Wrinkles | 70.73% | 29.27% | 82 |
|  | Fine Wrinkles? | 88.00% | 12.00% | 100 |
| 60-140-1 | Overall Wrinkles | 80.70% | 19.30% | 285 |
|  | Deep Wrinkles | 66.93% | 33.07% | 127 |
|  | Fine Wrinkles? | 91.77% | 8.23% | 158 |

The assessors noticed a great reduction in the pores (Table 11) and an improvement in mattification (Table 12) in the panelists' skin following treatment. The panelists' skin tone was also slightly improved and the skin looked tightened based on the evaluations from the assessors (Table 11).

TABLE 11

|  | Improved Group | No Change or Worsened | Out of |
|---|---|---|---|
| Pore Size |  |  |  |
| 60-140-LX2 | 95.92% | 4.08% | 98 |
| 60-140-1 | 93.13% | 6.88% | 160 |
| Skin Tone |  |  |  |
| 60-140-LX2 | 67.00% | 33.00% | 100 |
| 60-140-1 | 58.23% | 41.77% | 158 |
| Looks Tight |  |  |  |
| 60-140-LX2 | 78.79% | 21.21% | 99 |
| 60-140-1 | 75.00% | 25.00% | 152 |

TABLE 12

| Mattification | Improved Group | No Change or Worsened | Out of |
|---|---|---|---|
| 60-140-LX2 | 99.00% | 1.00% | 100 |
| 60-140-1 | 98.13% | 1.88% | 160 |

While both formulations seemed to give a more youthful look to the skin, 60-140-LX2 showed a greater improvement in creating a youthful look (90%) and having a natural feeling (86%) compared to the 60-140-1 formulation (73% and 79% respectively) (Table 13). Striking observations were also made on the tactile feelings of the treated skin with these formulations.

TABLE 13

| More Youthful? | Improved Group | No Change or Worsened | Out of |
|---|---|---|---|
| 60-140-LX2 | 89.90% | 10.10% | 99 |
| 60-140-1 | 72.50% | 27.50% | 160 |
| Natural Looking | Natural | Artificial or Very Artificial | Out of |
| 60-140-LX2 | 55.00% | 45.00% | 100 |
| 60-140-1 | 55.00% | 45.00% | 160 |
| Natural Feeling | Natural | Artificial or Very Artificial | Out of |
| 60-140-LX2 | 86.00% | 14.00% | 100 |
| 60-140-1 | 78.21% | 21.79% | 156 |

Silky, Smooth and Soft are the top three descriptors that the assessors chose to describe the feeling of the treated skin. (Table 14)

TABLE 14

| | Feeling Desc: | | | | | | | |
|---|---|---|---|---|---|---|---|---|
| | Rough | Rubbery | Silky | Smooth | Soft | Tacky | Dry | Out of |
| 60-140-LX2 | 3.00% | 20.00% | 53.00% | 69.00% | 70.00% | 2.00% | 0.00% | 100 |
| 60-140-1 | 3.13% | 12.50% | 56.25% | 71.25% | 78.13% | 0.63% | 0.63% | 160 |

Example 7: Development of Cleanser to Remove Body Corrective Compositions

It was found that commercially available cleansers were not effective at removing the film formed upon application of the body corrective compositions of the invention. To evaluate the performance of the cleansers, the film was applied to facial skin of volunteers. Following six to eight hours, the cleanser was rubbed onto the film and left on the film for 30 seconds. The subject was then instructed to remove the film with a towelette of a given surface roughness by gentle wiping the swollen film from the skin. The following commercially available products were tested:

Philosophy Purity Made Simple
Shiseido Benefiance Creamy Cleansing foam
Noxema
Estee Lauder Perfectly Clean Splash Away Foaming Cleanser
Makeup forever sens'eyes
Loreal go 360 clean deep
Clinique naturally gentle eye makeup remover
Olay Total Effects 7 in 1 antiaging cleanser
Olay dual action cleanser and pore scrub
Gamier Skin Renew
Lancome Bi-Facil double action make-up remover
Neutrogena deep clean invigorating foaming scrub
Olay regenerist daily regenerating cleanser
CVS pharmacy deep cleansing makeup remover
Neutrogena Ageless essentials Continuous Hydration Cream Cleanser
CVS cleansing and makeup remover
Yes to cucumbers natural glow facial towelettes As none of the aforementioned products were effective at removing the film, a cleanser was prepared to disrupt the mechanical integrity of the film and to facilitate the delivery of the cleanser components into the film. Without being bound by theory, the removal mechanism can be described in four steps with key formula components for each step indicated in parentheses:

1. Film wetting (Silsoft 034, Silsoft ETS, 5CS dimethicone)
2. Penetration of formula components (siloxane emulsifiers, siloxane phase, glycols, Cremaphor EL)
3. Film swelling (Silsoft 034, Silsoft ETS, Isododecane, 5CS dimethicone)
4. Film release from skin (glycols, water)

Silsoft 034, Silsoft ETS, 5CS dimethicone readily wet the surface of the film. The siloxane emulsifiers or the Cremaphor EL incorporate the aqueous phase into the siloxane phase, and may facilitate delivery of the film swelling components into the film. Silsoft 034, isododecane, and Silsoft ETS contribute to swelling the film and mechanical disruption. This enables penetration of the aqueous phase, hydration of the skin and reduction of the film's adhesion to the skin.

Tables 15-17, below, provide compositions that were effective in removing the film:

TABLE 15

| | w/w | gm |
|---|---|---|
| siloxane phase | | |
| Silsoft 034 (caprylyl methicone) | 9.7% | 5 |
| Isododecane | 19.4% | 10 |
| Silsoft ETS (ethyl trisiloxane) | 19.4% | 10 |
| Aerogel VM2270 | 1.5% | 0.763 |
| siloxane emulsifiers | | |
| Shin Etsu KSG 820 | 3.9% | 2 |
| Shin Etsu KF 6038 | 3.9% | 2 |
| aqueous phase | | |
| propylene glycol | 4.9% | 2.5 |
| butylene diglycol | 4.9% | 2.5 |
| glycerol | 1.9% | 1 |
| MPDiol | 7.8% | 4 |
| DI water | 19.4% | 10 |
| neolone PE | 0.5% | 0.27 |
| chronosphere optical brite | 0.6% | 0.3 |
| granpowder nylon | 2.1% | 1.1 |

TABLE 16

| Component No. | Component | Percent of Formulation (%) |
|---|---|---|
| 1 | Glycerin | 3.00% |
| 2 | water | 43.98% |
| 3 | dowanol DPM | 6.00% |
| 5 | cremaphor EL | 6.00% |
| 6 | silsoft ETS | 30.00% |
| 7 | DM5 CS | 10.00% |
| 8 | prestige pearlescent beige | 0.02% |
| 9 | Jeecide cap 5 | 1.00% |

TABLE 17

| Component No. | Component | Percent of Formulation (%) |
|---|---|---|
| 1 | Glycerin | 3.11% |
| 2 | water | 46.23% |
| 3 | dowanol DPM | 6.20% |
| 4 | cremaphor EL | 6.22% |
| 5 | silsoft ETS | 12.43% |
| 6 | DC 200 Fluid (1 cSt) | 15.49% |
| 7 | DM5 CS | 9.30% |
| 8 | Xirona Caribbean blue | 0.02% |
| 9 | Jeecide cap 5 | 1.00% |

Procedure:

Components 1-4 and 9 were mixed until a clear dispersion formed (Phase A). Compounds 5-8 were mixed separately until a uniform solids dispersion was formed. Phase A was subsequently added to Phase B and mixed.

Example 8: Viscosity Measurements

The viscosity of a fluid can be measured by many methods known to one of skill in the art. Specifically, "The rheology handbook: for users of rotational and oscillatory rheometers By Thomas G. Mezger" or ASTM standards such as ASTM D3835-08, ASTM D2857-95, ASTM D2196-10, and ASTM D2983-09 instruct one of skill in the art on how to measure the viscosity of a fluid. Illustrative methods also include the following methods:

Method A

I. Overview

This protocol determines the viscosity (cP) on a Brookfield Viscometer. This protocol can be performed on a wide variety of formulations including but not limited to immediate effects treatment, and perfector.

II. Background

The viscosity of formulation is critical to its performance and its aesthetics. Furthermore a change in viscosity with time or exposure to a stress condition is an important indicator of formulation instability. As such, it is important to be able to reproducibly and accurately evaluate formulation viscosity. The following protocol can be used to determine the viscosity at single shear rate of a formulation whose viscosity is between 50 and 300 Pas.

III. Materials

A full 2 oz to 8 oz jar containing formulation of interest
Brookfield DV-II+ Pro EXTRA Viscometer and RV-6 spindle.
Test requires ~5 minutes per sample IV. Analytical Precautions Clean the viscometer geometry prior to use
Insert the geometry to the appropriate depth in the center of the sample container
Insure the container is stationary during the test V. Protocol 5.1 Preparing Equipment:
1. Turn on the Brookfield DV-II+ Pro EXTRA Viscometer by pressing a switch in the back of the instrument. Select "External Mode" by pressing the up arrow on the instrument control panel.
2. Start the Rheocalc software, a shortcut to which can be found on the desktop
3. Zero the viscometer by clicking the lightning symbol on the dashboard tab (Instrument geometry should NOT be installed)
4. Find RV-6 test geometry and clean with 50%/50% IPA/Mineral Spirits mixture, then wipe dry
5. Insert RV-6 geometry by pulling the instrument geometry holder sleeve up.
6. Pick the test method by clicking Test tab, and opening Hold0.5-RV6-081511.RCP method.

5.2 Preparing Sample:
1. No special sample preparation is required other than doing a visual inspection to ensure the sample appears uniform.

5.3 Perform Viscosity Measurement:
1. Insert the geometry into the 2 to 8 oz of sample under.
   i. Insure that the geometry is inserted to the correct measuring height as indicated by thin section in the rod of the geometry
   ii. Insure that the geometry is centered in the jar
2. Adjust the stand so as to keep the sample and the geometry in the appropriate relative position.
3. Click the small play button in the test tab to start the test
4. Name the data file appropriately and save the file to the appropriate location
5. Allow the test to run to completion, then save your data for later analysis 6. To test another sample:
   i. Slide the sample stand out and remove the sample from the instrument
   ii. Remove the geometry from the instrument and gently wipe down all surfaces with 50% IPA, 50% Mineral Spirit mixture. Dry with a lint free wipe.
   iii. Replace the geometry, return to test tab and start next test
7. After finishing with the last test sample, clean geometry with 50% IPA, 50% Mineral Spirit mixture, then wipe dry and place back in geometry box.

VI. Data Analysis
1. Open datafile (*.DB) and click the export button to obtain an excel file containing the data.
2. Locate the ViscometerPerfectorTemplate_JL-081511-v1-beta1.xlsx Excel template for data analysis
3. Paste the data into the first sheet
4. Record the average viscosity and the standard deviation
5. Save the template as an electronic record with a new name that references the analyzed sample.
1. Repeat analysis for each data set.

Method B

I. Overview

This protocol determines the viscosity (Pas) at 0.5 1/s, Shear Thinning factor (Pa*s^2), and the strain rate of instability. This protocol can be performed on a wide variety of formulations including but not limited to immediate effects treatment, and perfector, along with any other "cream" or "lotion"

II. Background

The viscosity of formulas and its change has been correlated to stability of formulations. As such, it is important to be able to reproducibly and accurately evaluate their viscosity properties to be used as a predictive tool for stability of Immediate Effects active prototypes. The following protocol can be used to determine the viscosity, shear thinning factor, and strain rate of instability.

III. Materials

>1 g Formulation of Interest
Bohlin CVO100 Rheometer mounted with 20 mm Parallel plate geometry
Test requires ~12 minutes per sample IV. Analytical Precautions Clean sides of the geometry are critical for accurate test results
Any deviations must be noted V. Protocol 5.1 Preparing Equipment:
8. Set up the Bohlin Rheometer
   a. Turn on the instrument
   b. Turn on the temperature controller
   c. Start the Bohlin software
   d. Load the viscosity stability test template
   e. Make sure both the geometry and plate are clean
9. Install the geometry
   a. Zero the instrument and you are now ready to being testing,
10. For testing of multiple samples simply raise and clean the geometry first with a dry wipe, then with a 50%/50% IPA/Mineral Spirits mixture, then again with a dry wipe.

5.2 Preparing Sample:
1. No special sample preparation is required other than doing a visual inspection to ensure the sample appears uniform.

VI. Perform the viscosity test
7. Place ~1 g of mixed material onto the bottom plate in a mound centered below the geometry
8. Lower the geometry to the correct gap (250 um)
9. Clean the excess material from the sides of the geometry using the flat end of a spatula
10. Allow the test to run to completion, then save your data for later analysis
11. To continue onto the next test, raise the geometry and remove the sample from the instrument. Gently wipe down all surfaces with 50% ipa/50% mineral spirits mixture. Dry with a lint free wipe.
12. You are now ready to commence the next cure test VII. Data Analysis:
2. Locate the following Excel Template for the data analysis ViscosityStabilityTemplate061411-v2
3. Paste the raw instrument data from the appropriate Bohlin Viscometry Data File file into A:2 of sheet 1 (near the left corner) of the excel document
4. Paste the sample name into A:1 of sheet 1 of the excel document
5. Record the calculated "Viscosity (Pas) at 0.5 l/s" as viscosity
6. Record the calculated "Shear Thinning factor (Pa*s^2)" as the shear thinning factor
7. Record the calculated "Strain Rate of instability" as the Strain Stability (Scale is out of 100)
8. Save the completed template as an electronic record with an appropriate file name
9. Repeat steps 2 to 7 for remaining raw data

EQUIVALENTS

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

The invention claimed is:
1. A formulation for application to the skin, comprising:
a) a reactive reinforcing component comprising
  1) a reactive constituent comprising as ingredients at least one alkenyl functionalized organopolysiloxane and at least one hydride functionalized polysiloxane; and
  2) a reinforcing constituent; and
b) a cross-linking component comprising as ingredients at least one catalyst and a vinyl terminated organopolysiloxane;
wherein the cross-linking component facilitates a reaction to form a film in situ on the skin; wherein the reactive reinforcing component has a viscosity of between about 50,000 and 500,000 cSt at 25° C.;
wherein the at least one alkenyl functionalized organopolysiloxane has a viscosity of between about 100,000 and about 500,000 cSt at 25° C.;
wherein the at least one hydride functionalized polysiloxane has a viscosity of between about 2 and 10,000 cSt at 25° C.;
wherein the at least one alkenyl functionalized organopolysiloxane or the vinyl terminated organopolysiloxane, or both, has formula (IIa):

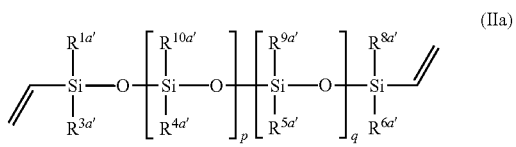

wherein $R^{1a'}$, $R^{3a'}$, $R^{4a'}$, $R^{5a'}$, $R^{6a'}$, $R^{8a'}$, $R^{9a'}$ and $R^{10a'}$ are each independently selected from hydrogen, $C_{1-20}$ alkyl, $C_{2-20}$ alkenyl, $C_{5-10}$ aryl, hydroxyl and $C_{1-20}$ alkoxyl, and p and q are each independently an integer from between 10 and about 6000; and wherein the at least one alkenyl functionalized organopolysiloxane comprises a vinyl group, and wherein the reactive reinforcing component has a vinyl to functional hydride molar ratio of between about 1:10 and about 1:100.

2. The formulation of claim 1, wherein the reactive reinforcing component and the cross-linking component are prevented from coming into contact prior to use.

3. The formulation of claim 1, wherein the at least one alkenyl functionalized organopolysiloxane has a viscosity of between about 110,000 about 450,000 cSt at 25° C.

4. The formulation of claim 1, wherein the at least one alkenyl functionalized organopolysiloxane is selected from the group consisting of vinyl terminated polydimethylsiloxane; vinyl terminated diphenyl siloxane-dimethylsiloxane copolymers; vinyl terminated polyphenylmethylsiloxane, vinylphenylmethyl terminated vinylphenylsiloxane-phenylmethylsiloxane copolymer; vinyl terminated trifluoropropylmethylsiloxane-dimethylsiloxane copolymer; vinyl terminated diethyl siloxane-dimethylsiloxane copolymer; vinylmethylsiloxane-dimethylsiloxane copolymer, trimethylsiloxy terminated; vinylmethylsiloxane-dimethylsiloxane copolymers, silanol terminated; vinylmethylsiloxane-dimethylsiloxane copolymers, vinyl terminated; vinyl gums; vinylmethylsiloxane homopolymers; vinyl T-structure polymers; monovinyl terminated polydimethylsiloxanes; vinylmethylsiloxane terpolymers; vinylmethoxysilane homopolymers and combinations thereof.

5. The formulation of claim 1, wherein the at least one alkenyl functionalized organopolysiloxane is vinyl terminated.

6. The formulation of claim 1, wherein the at least one alkenyl functionalized organopolysiloxane is polydimethylsiloxane.

7. The formulation of claim 1, wherein the at least one alkenyl functionalized organopolysiloxane has a weight percent of vinyl of between about 0.01 and about 0.1.

8. The formulation of claim 1, wherein the at least one alkenyl functionalized organopolysiloxane has a vinyl equivalent per kilogram of between about 0.001 and about 0.05.

9. The formulation of claim 1, wherein the vinyl terminated organopolysiloxane is less than about 50% by weight of the cross-linking component.

10. The formulation of claim 1, wherein the vinyl terminated organopolysiloxane is selected from the group consisting of vinyl terminated polydimethylsiloxane; vinyl terminated diphenyl siloxane-dimethylsiloxane copolymers; vinyl terminated polyphenylmethylsiloxane, vinylphenylmethyl terminated vinylphenylsiloxane-phenylmethylsiloxane copolymer; vinyl terminated trifluoropropylmethylsiloxane-dimethylsiloxane copolymer; vinyl terminated diethyl siloxane-dimethylsiloxane copolymer; vinylmethylsiloxane-dimethylsiloxane copolymers, vinyl terminated; monovinyl terminated polydimethylsiloxanes; and combinations thereof.

11. The formulation of claim 1, wherein the vinyl terminated organopolysiloxane is vinyl terminated polydimethylsiloxane.

12. The formulation of claim 1, wherein the at least one hydride functionalized polysiloxane has a percent SiH content of between about 5 and about 75%.

13. The formulation of claim 1, wherein the at least one hydride functionalized polysiloxane has a SiH content of between about 0.5 and about 10 mmol/g.

14. The formulation of claim 1, wherein the at least one hydride functionalized polysiloxane is selected from the group consisting of hydride terminated polydimethylsiloxane; polyphenyl-(dimethylhydrosiloxy)siloxane, hydride terminated; methylhydrosiloxane-phenylmethylsiloxane copolymer, hydride terminated; methylhydrosiloxane-dimethylsiloxane copolymers, trimethylsiloxy terminated; polymethylhydrosiloxanes, trimethylsiloxy terminated; polyethylhydrosiloxane, triethylsiloxane, methylhydrosiloxane-phenyloctylmethylsiloxane copolymer; methylhydrosiloxane-phenyloctylmethylsiloxane terpolymer and combinations thereof.

15. The formulation of claim 1, wherein the at least one hydride functionalized polysiloxane is alkyl terminated.

16. The formulation of claim 1, wherein the at least one hydride functionalized polysiloxane is methylhydrosiloxane-dimethylsiloxane copolymers, trimethylsiloxy terminated.

17. The formulation of claim 1, wherein the at least one hydride functionalized polysiloxane has at least 2 Si—H units.

18. The formulation of claim 1, wherein the at least one hydride functionalized polysiloxane has at least 3 Si—H units.

19. The formulation of claim 1, wherein the reinforcing constituent has a surface area of between about 100 and about 300 m$^2$/g.

20. The formulation of claim 1, wherein the reinforcing constituent has an average particle size of between about 1 and about 20 μm.

21. The formulation of claim 1, wherein the reinforcing constituent is selected from the group consisting of optionally surface treated mica, zinc oxide, titanium dioxide, aluminum oxide, clay and silica.

22. The formulation of claim 1, wherein the reinforcing constituent is silica.

23. The formulation of claim 22, wherein the silica is fumed silica.

24. The formulation of claim 23, wherein the fumed silica is surface treated with hexamethyldisilazane.

25. The formulation of claim 1, wherein the reactive reinforcing component further comprises one or more of feel modifiers, spreadability enhancers, adhesion modifiers, diluents, tack modifiers, optics modifiers, particles, volatile siloxanes, emulsifiers, emollients, surfactants, thickeners, solvents, film formers, humectants, preservatives and pigments.

26. The formulation of claim 1, wherein the reactive constituent and reinforcing constituent comprise between about 20 and about 90% of the reactive reinforcing component.

27. The formulation of claim 1, wherein the reinforcing constituent is between about 2 and about 11% of the reactive reinforcing component.

28. The formulation of claim 1, wherein the reactive constituent comprises between about 18 and about 50% of the reactive reinforcing component.

29. The formulation of claim 1, wherein the at least one catalyst comprises a metal catalyst.

30. The formulation of claim 29, wherein the metal catalyst is a platinum catalyst.

31. The formulation of claim 30, wherein the platinum catalyst is selected from the group consisting of platinum carbonyl cyclovinylmethylsiloxane complexes, platinum divinyltetramethyldisiloxane complexes, platinum cyclovinylmethylsiloxane complexes, platinum octanaldehyde/octanol complexes and combinations thereof.

32. The formulation of claim 1, wherein the at least one catalyst comprises between about 0.005 and about 0.04% of the cross-linking component.

33. The formulation of claim 1, wherein the cross-linking component further comprises one or more of feel modifiers, spreadability enhancers, adhesion modifiers, diluents, tack modifiers, optics modifiers, particles, volatile siloxanes, emulsifiers, emollients, surfactants, thickeners, solvents, film formers, humectants, preservatives and pigments.

34. The formulation of claim 1, further comprising a cosmetic agent or a therapeutic agent.

35. A film prepared by a process comprising the steps of:
a) applying the reactive reinforcing component of the formulation of claim 1 to the skin of a subject; and
b) applying the cross-linking component of the formulation of any of claim 1 to the reactive reinforcing component,
wherein the cross-linking component catalyzes an in situ cross-linking reaction, such that a film is formed on the skin.

36. The film of claim 35, wherein the film is body corrective, body shaping, and/or body lifting.

37. The film of claim 35, wherein the film is formed within 5 minutes.

38. The film of claim 35, wherein the film has a leather adhesive force of greater than about 20 N/mm.

39. The film of claim 35, wherein the film has a Young's Modulus of between about 0.01 and about 1 MPa.

40. The film of claim 35, wherein the fracture strain of the film is at least about 150%.

41. The film of claim 35, wherein the film has a hysteresis of less than about 5%.

42. The film of claim 35, wherein the film has an adhesion of between about 20 N/mm and about 80 N/mm.

43. The film of claim 35, wherein the film is less than about 100 microns thick.

44. The film of claim 35, wherein the film shrinks by less than about 1 to about 15%.

45. The film of claim 35, wherein the film upon application to the skin of the subject has the appearance of natural skin of said subject.

46. The film of claim 35, wherein the film upon application to the body provides elasticity and recoil approaching that of youthful skin.

47. A method for correcting skin imperfections on a subject's skin comprising applying to the subject's skin the formulation of claim 1,
wherein the cross-linking component catalyzes an in situ cross-linking reaction, such that a film is formed on the skin, thereby correcting the skin imperfections.

48. A method for protecting a subject's skin comprising applying to the subject's skin the formulation of claim 1, wherein the cross-linking component catalyzes an in situ cross-linking reaction, such that a film is formed on the skin, thereby protecting the skin.

49. The method of claim 48, wherein the film protects the skin from damage by sun, wind, rain or environmental toxins.

50. A method of shaping a subject's body, comprising applying to the subject's body the formulation of claim 1,
wherein the cross-linking component catalyzes an in situ cross-linking reaction, such that a film is formed on the body, thereby shaping the body.

51. The method of claim 50, wherein the film shapes the body by providing support to soft body tissues.

52. The method of claim 51, wherein the film prevents sagging of soft body tissues.

53. The method of claim 51, wherein the soft body tissue includes the abdomen, the buttocks, the thighs, the neck, the brow, the jowls, the breasts, the skin under the arms, and the skin surrounding the eyes.

54. A method for delivering an agent to a subject, comprising applying to the subject's skin the formulation of claim 1 further comprising one or more agents,
wherein the cross-linking component catalyzes an in situ cross-linking reaction, such that a film is formed on the skin, thereby delivering the agent to the subject.

55. The method of claim 54, wherein the agent is a cosmetic or a therapeutic agent.

56. The formulation of claim 1, comprising at least one function modulating component.

57. The formulation of claim 1, comprising at least one treatment specific component.

58. The formulation of claim 1, further comprising a finishing formulation applied to the film after formation of the film.

59. The film of claim 35, further comprising a finishing formulation applied to the film after formation of the film.

60. The method of claim 47, wherein the method further comprises applying a finishing formulation to the film after formation of the film.

61. The formulation of claim 1, further comprising a pigment dispersion formulation.

62. The formulation of claim 61, wherein the pigment dispersion formulation is applied prior to or after the application of the reactive reinforcing component to the skin.

63. The formulation of claim 61, wherein the pigment dispersion formulation is applied prior to or after the application of the cross-linking component to the skin.

64. The formulation of claim 61, wherein the pigment dispersion formulation is applied in between the application of the reactive reinforcing component and the cross-linking component to the skin.

65. The film of claim 35, further comprising applying a pigment dispersion formulation.

66. The film of claim 65, wherein the pigment dispersion formulation is applied before or after the application of the reactive reinforcing component to the skin.

67. The film of claim 65, wherein the pigment dispersion formulation is applied before or after the application of the cross-linking component.

68. The film of claim 65, wherein the pigment dispersion formulation is applied after the application of the reactive reinforcing component but before the application of the cross-linking component to the skin.

69. The method of claim 47, further comprising the step of applying a pigment dispersion formulation.

70. The method of claim 69, wherein the pigment dispersion formulation is applied before or after the application of the reactive reinforcing component to the skin.

71. The method of claim 69, wherein the pigment dispersion formulation is applied before or after the application of the cross-linking component.

72. The method of claim 69, wherein the pigment dispersion formulation is applied after the application of the reactive reinforcing component but before the application of the cross-linking component to the skin.

73. The formulation of claim 1, wherein the reactive reinforcing component and the cross-linking component are prevented from coming into contact prior to application to the skin.

* * * * *

UNITED STATES PATENT AND TRADEMARK OFFICE
CERTIFICATE OF CORRECTION

PATENT NO. : 9,724,363 B2  
APPLICATION NO. : 14/833565  
DATED : August 8, 2017  
INVENTOR(S) : Betty Yu et al.

It is certified that error appears in the above-identified patent and that said Letters Patent is hereby corrected as shown below:

At Column 80, Claim number 3, Line number 24, after "110,000" please insert -- and --.

Signed and Sealed this  
Twenty-eighth Day of November, 2017

Joseph Matal  
*Performing the Functions and Duties of the*  
*Under Secretary of Commerce for Intellectual Property and*  
*Director of the United States Patent and Trademark Office*